(12) United States Patent
Bibbo et al.

(10) Patent No.: US 6,981,794 B2
(45) Date of Patent: Jan. 3, 2006

(54) METHODS FOR MIXING SOLUTIONS

(75) Inventors: Kenneth L. Bibbo, Freehold, NJ (US); Gregory P. Elgan, Providence, UT (US); Michael Goodwin, Logan, UT (US); Bradley Buchanan, Rose, CA (US); Jim Austin, Cleburne, TX (US)

(73) Assignee: Hynetics LLC, Logan, UT (US)

( * ) Notice: Subject to any disclaimer, the term of this patent is extended or adjusted under 35 U.S.C. 154(b) by 142 days.

(21) Appl. No.: 10/402,338

(22) Filed: Mar. 28, 2003

(65) Prior Publication Data
US 2005/0073908 A1 Apr. 7, 2005

Related U.S. Application Data
(60) Provisional application No. 60/372,162, filed on Apr. 12, 2002.

(51) Int. Cl.
*B01F 11/00* (2006.01)

(52) U.S. Cl. .................. 366/149; 366/314; 366/316; 366/332

(58) Field of Classification Search ............... 366/332, 366/333, 334, 335, 276, 275, 278, 277, 255, 366/258, 257, 260, 314, 316, 149; 604/408, 604/416; 383/217; 206/219
See application file for complete search history.

(56) References Cited

U.S. PATENT DOCUMENTS

| | | | |
|---|---|---|---|
| 1,035,540 A | | 8/1912 | Creech |
| 1,776,405 A | | 9/1930 | Wilsey |
| 2,107,851 A | * | 2/1938 | Boehm .................. 426/250 |
| 2,336,438 A | * | 12/1943 | Evans .................... 366/108 |
| 2,419,330 A | * | 4/1947 | Anderson ................ 425/397 |
| 2,499,203 A | | 2/1950 | Warren |
| 2,513,577 A | | 7/1950 | Malme |
| 2,552,970 A | | 5/1951 | Horsley et al. |
| 2,615,692 A | | 10/1952 | Muller |
| 2,661,938 A | | 12/1953 | Kuentzel |
| 2,662,520 A | * | 12/1953 | McMahon .................. 435/1.3 |
| 2,797,903 A | | 7/1957 | Urban |
| 2,877,994 A | | 3/1959 | Jones |
| 3,010,303 A | | 11/1961 | Bochan |
| 3,096,081 A | * | 7/1963 | Helm et al. ................ 425/397 |
| 3,132,848 A | | 5/1964 | Garlinghouse |
| 3,467,363 A | | 9/1969 | Reichel |
| 3,647,397 A | | 3/1972 | Coleman |
| 3,945,618 A | | 3/1976 | Shoh |
| 3,962,892 A | | 6/1976 | Garlinghouse |
| 4,038,150 A | | 7/1977 | Dorn et al. |
| 4,053,142 A | | 10/1977 | Johannes |
| 4,072,030 A | | 2/1978 | Garlinghouse |
| 4,112,518 A | | 9/1978 | Garlinghouse |

(Continued)

FOREIGN PATENT DOCUMENTS

| | | |
|---|---|---|
| DE | 328484 | 10/1920 |
| DE | 1 027 185 | 11/1952 |
| GB | 2 145 634 A | 4/1985 |
| WO | WO 03/028869 A2 | 4/2003 |

OTHER PUBLICATIONS

LevTech, Inc., *Business Plan*, pp. 1, 8, 9, 11, 12, 13, and 25, Sep. 5, 2000.

Brochure by Graber & Pfenninger GmbH, *Vibrating Mixer Laboratory Type, Mixing, Liquids by Vibration*, publication date believed to be at least as early as Jun. 2001.

*Primary Examiner*—Tony G. Soohoo
(74) *Attorney, Agent, or Firm*—Workman Nydegger

(57) ABSTRACT

A method for mixing a solution includes positioning a collapsible container within a chamber of a substantially rigid tank. The collapsible container bounds a compartment. A mixer is disposed within the compartment of the container. Two or more components are fed into the compartment of the container. At least one of the components is a liquid. The mixer is raised and lowered within the compartment of the container so as to mix the components.

28 Claims, 40 Drawing Sheets

U.S. PATENT DOCUMENTS

| | | | |
|---|---|---|---|
| 4,114,522 A | 9/1978 | Nagamine | |
| 4,177,575 A | 12/1979 | Brooks | |
| 4,185,072 A | 1/1980 | Puderbaugh et al. | |
| 4,198,166 A | 4/1980 | Tuns | |
| 4,242,001 A | 12/1980 | Meintker et al. | |
| 4,243,080 A | 1/1981 | Choksi et al. | |
| 4,250,694 A * | 2/1981 | Rochman | 53/572 |
| 4,423,945 A | 1/1984 | Preston et al. | |
| 4,436,458 A | 3/1984 | Wisdom et al. | |
| 4,479,098 A | 10/1984 | Watson | |
| 4,498,785 A | 2/1985 | de Bruyne | |
| 4,511,254 A | 4/1985 | North et al. | |
| 4,515,482 A | 5/1985 | Schadewald | |
| 4,548,509 A | 10/1985 | Parrott et al. | |
| 4,562,413 A | 12/1985 | Mishiro et al. | |
| 4,687,962 A | 8/1987 | Elbert | |
| 4,732,487 A | 3/1988 | Pollard | |
| 4,787,751 A | 11/1988 | Bakels | |
| 4,946,434 A | 8/1990 | Plaisted et al. | |
| 4,964,333 A | 10/1990 | Bravo | |
| 4,966,468 A | 10/1990 | Brüning | |
| 4,973,168 A | 11/1990 | Chan | |
| 4,983,045 A | 1/1991 | Taniguchi | |
| 5,032,027 A | 7/1991 | Berliner, III | |
| 5,033,321 A | 7/1991 | Gerson | |
| 5,088,830 A | 2/1992 | Mühlbauer | |
| 5,160,333 A | 11/1992 | Wells | |
| 5,193,977 A | 3/1993 | Dame | |
| 5,257,983 A | 11/1993 | Garyantes et al. | |
| 5,304,130 A | 4/1994 | Button et al. | |
| 5,350,080 A | 9/1994 | Brown et al. | |
| 5,362,642 A | 11/1994 | Kern | |
| 5,385,564 A | 1/1995 | Slater et al. | |
| 5,431,201 A | 7/1995 | Torchia et al. | |
| 5,499,871 A | 3/1996 | Ulrich et al. | |
| 5,555,796 A | 9/1996 | Kortschot et al. | |
| 5,564,829 A | 10/1996 | Lafond | |
| 5,620,250 A | 4/1997 | Chilcoat et al. | |
| 5,727,878 A | 3/1998 | Sullivan, Jr. | |
| 5,795,330 A | 8/1998 | Tofighi et al. | |
| 5,868,495 A | 2/1999 | Hidalgo | |
| 5,941,635 A | 8/1999 | Stewart | |
| 5,941,867 A | 8/1999 | Kao | |
| 6,029,563 A | 2/2000 | Nakagawa et al. | |
| 6,045,254 A | 4/2000 | Inbar et al. | |
| 6,071,005 A | 6/2000 | Ekambaram et al. | |
| 6,076,457 A | 6/2000 | Vallot | |
| 6,089,143 A | 7/2000 | Figueroa | |
| 6,095,676 A | 8/2000 | Kuan | |
| 6,113,257 A | 9/2000 | Sharon et al. | |
| 6,120,174 A | 9/2000 | Hoag et al. | |
| 6,142,661 A | 11/2000 | Lafond | |
| 6,176,607 B1 | 1/2001 | Hajianpour | |
| 6,190,913 B1 | 2/2001 | Singh | |
| 6,213,007 B1 | 4/2001 | Lande | |
| 6,245,555 B1 | 6/2001 | Curtis | |
| 6,267,498 B1 * | 7/2001 | Lafond et al. | 366/204 |
| 6,279,463 B1 | 8/2001 | Kajiwara | |
| 6,302,574 B1 | 10/2001 | Chan | |
| 6,364,520 B1 | 4/2002 | Steele | |
| 6,416,212 B1 * | 7/2002 | Rogers et al. | 366/117 |
| 6,416,215 B1 * | 7/2002 | Terentiev | 366/273 |
| 6,447,158 B1 | 9/2002 | Farkas | |
| 6,453,683 B1 * | 9/2002 | Wisniewski et al. | 62/75 |
| 6,491,422 B1 | 12/2002 | Rütten et al. | |
| 6,494,613 B2 | 12/2002 | Terentiev | |
| 6,634,783 B2 * | 10/2003 | Baron | 366/204 |
| 6,670,171 B2 * | 12/2003 | Carll | 435/289.1 |
| 6,709,862 B2 | 3/2004 | Curtis | |
| 6,758,593 B1 | 7/2004 | Terentiev | |
| 2001/0039369 A1 | 11/2001 | Terentiev | |
| 2002/0031047 A1 | 3/2002 | Fromm | |
| 2002/0082173 A1 | 6/2002 | Terentiev | |
| 2002/0145940 A1 | 10/2002 | Terentiev | |
| 2004/0027912 A1 * | 2/2004 | Bibbo et al. | 366/149 |
| 2004/0047232 A1 | 3/2004 | Terentiev | |
| 2004/0062140 A1 * | 4/2004 | Cadogan et al. | 366/144 |
| 2004/0159616 A1 | 8/2004 | Cohee et al. | |
| 2004/0190372 A1 | 9/2004 | Goodwin et al. | |
| 2004/0218468 A1 | 11/2004 | Terentiev | |

* cited by examiner

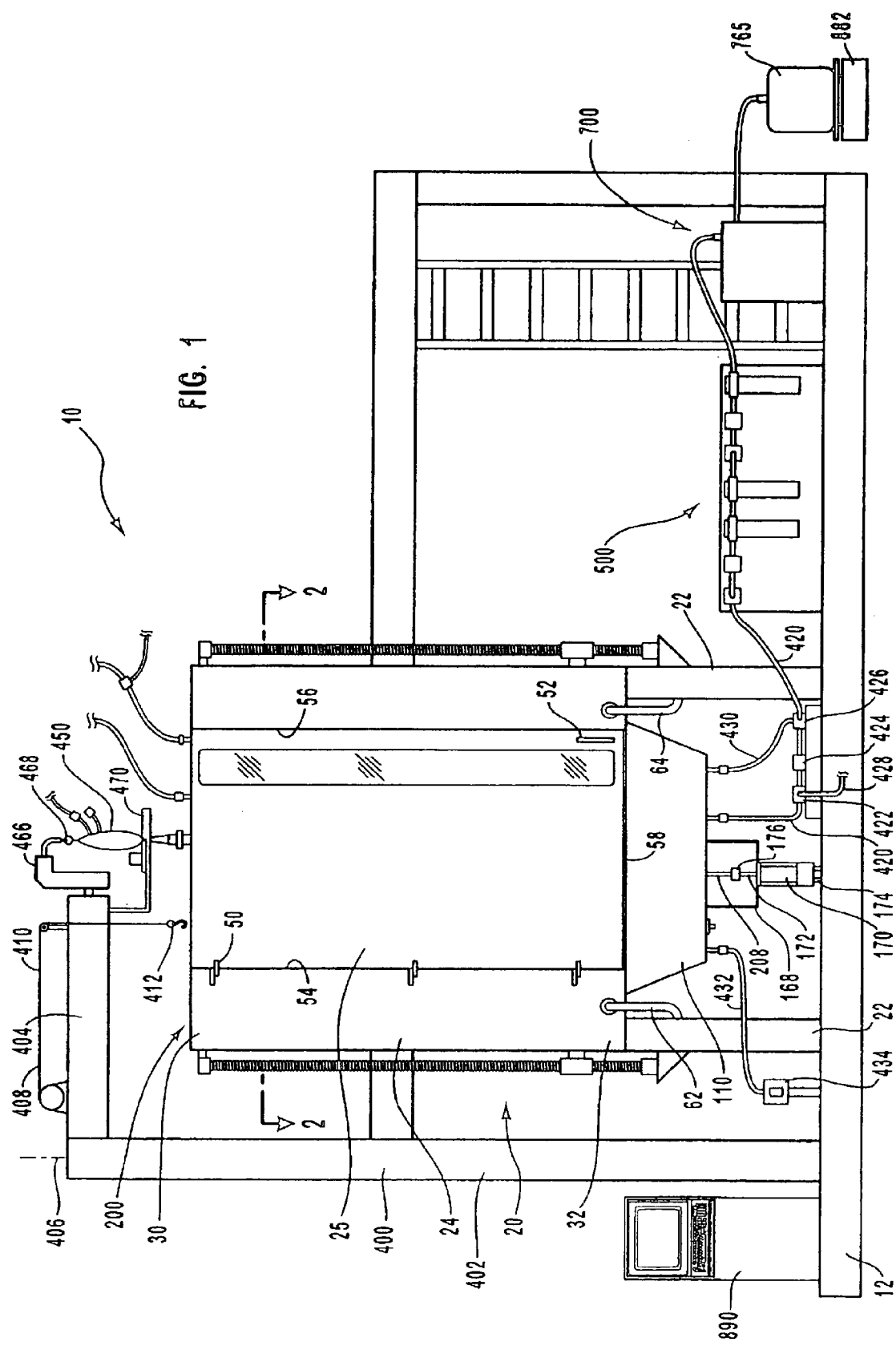

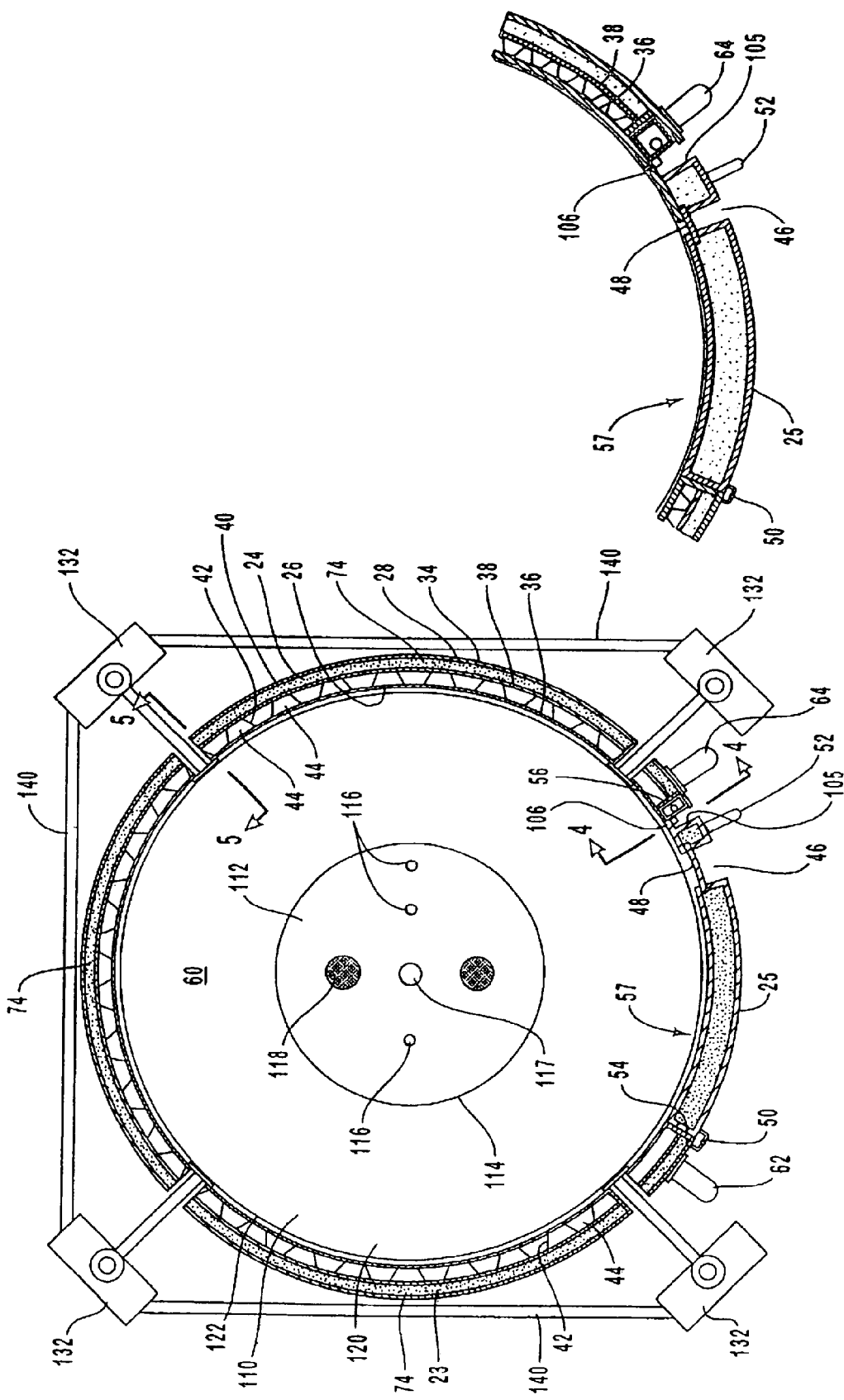

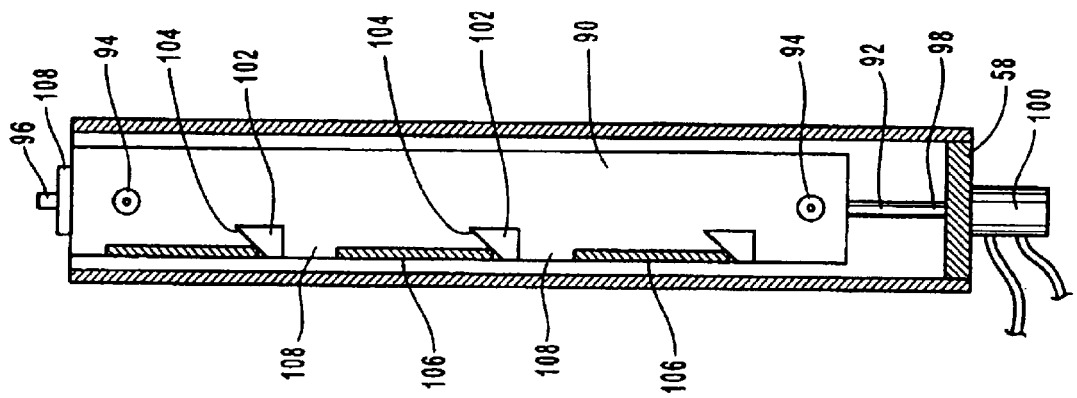
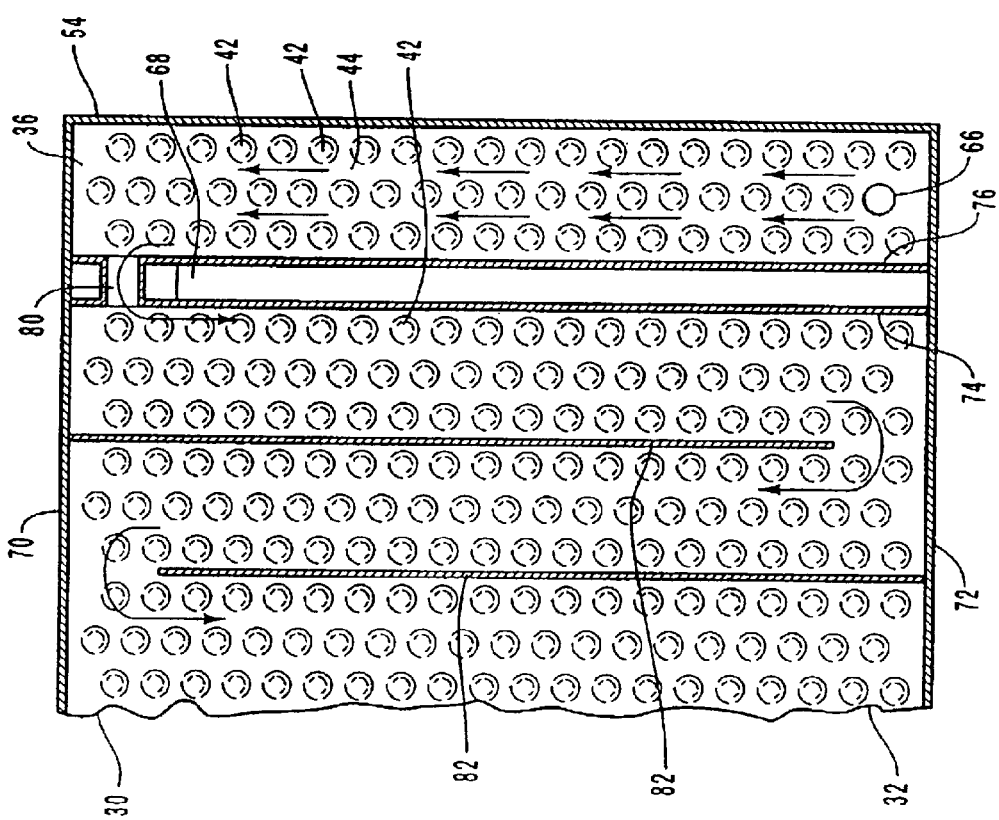

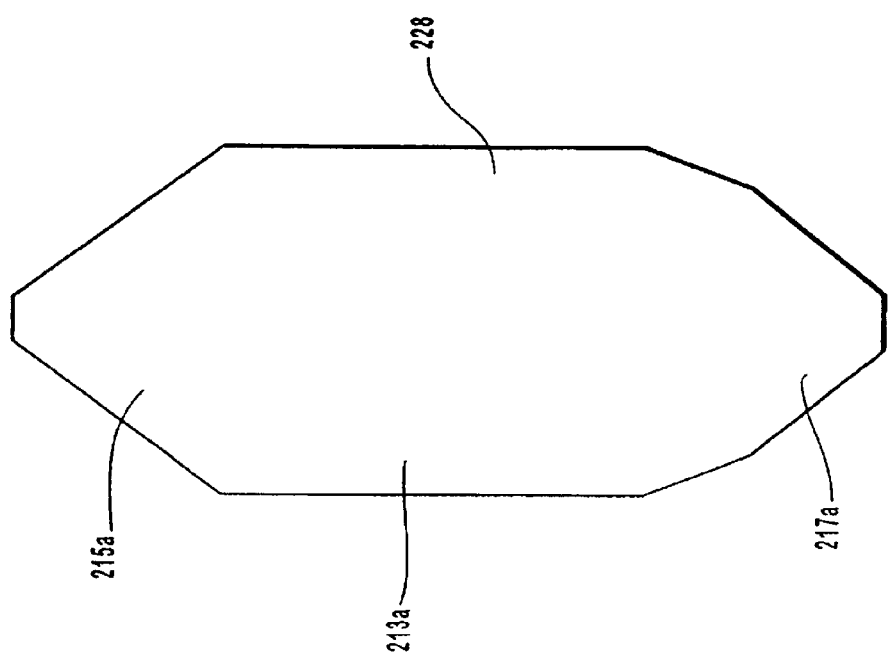

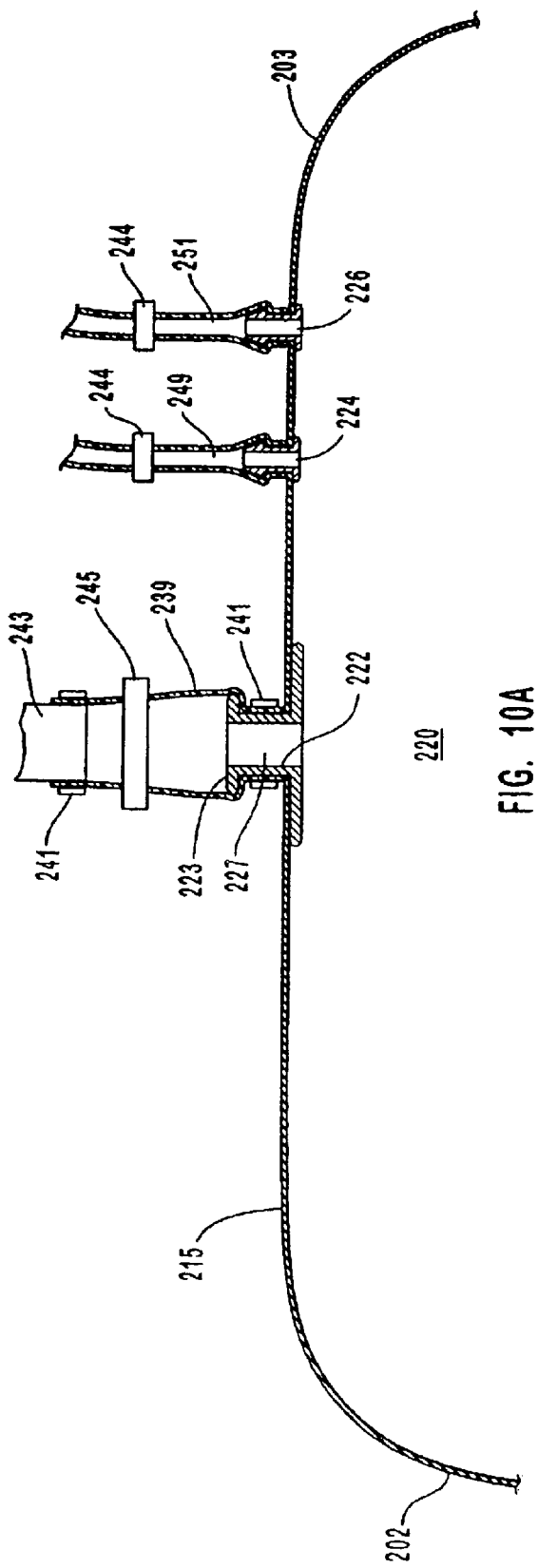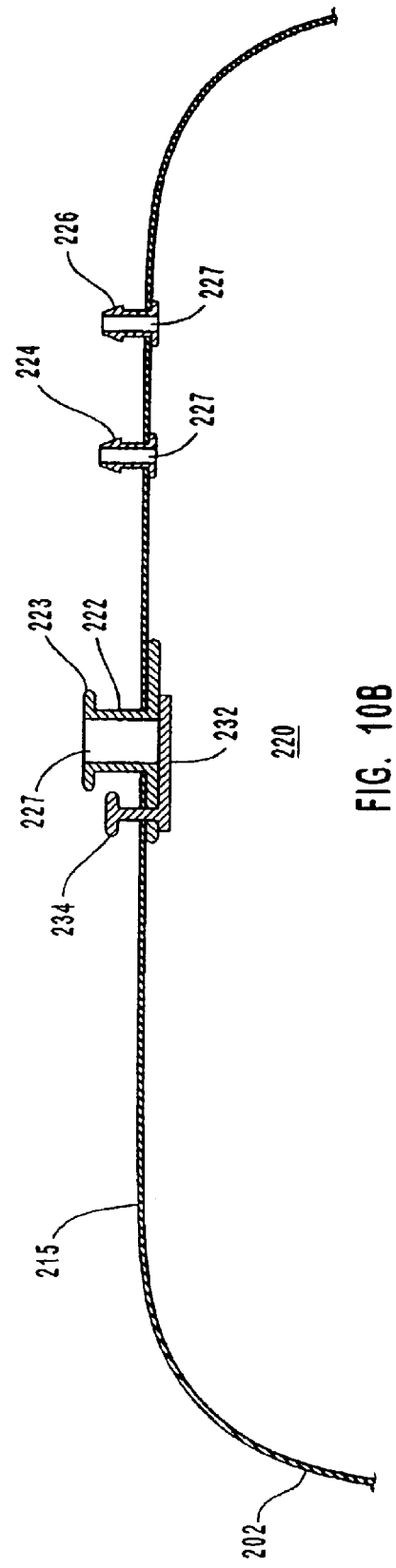

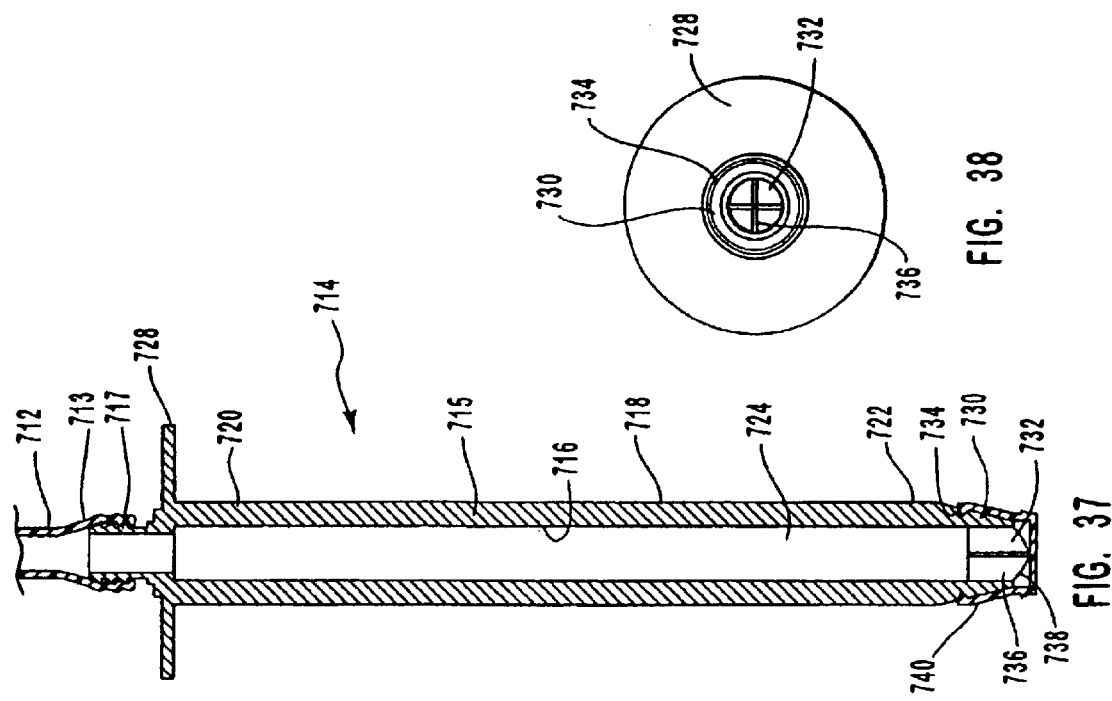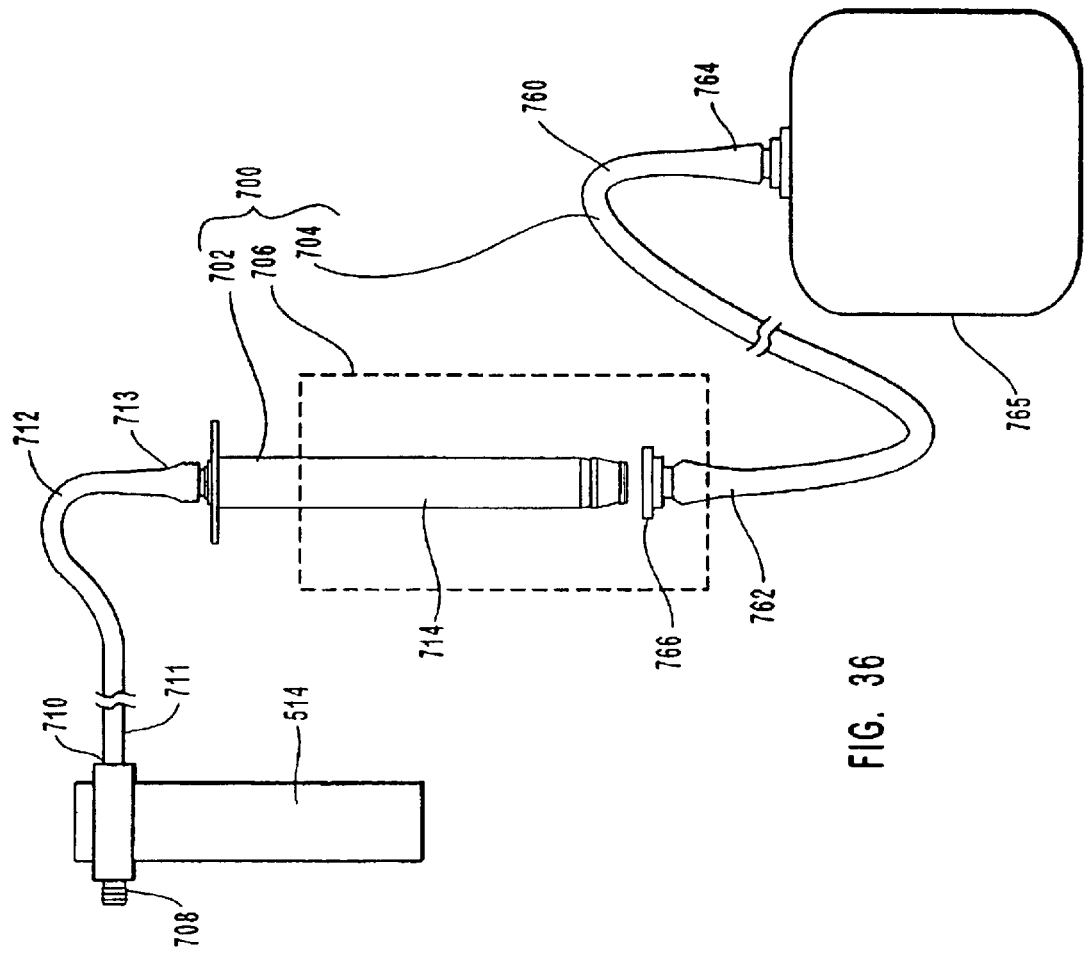

METHODS FOR MIXING SOLUTIONS

CROSS-REFERENCE TO RELATED APPLICATIONS

This application claims priority to U.S. Provisional Patent Application Ser. No. 60/372,162, filed Apr. 12, 2002, which application is incorporated herein by specific reference.

BACKGROUND OF THE INVENTION

1. The Field of the Invention

The present invention relates to methods for mixing solutions.

2. The Relevant Technology

Culture media, buffers, reagents and other biological materials (hereinafter "base materials") are used extensively by biotech companies in research and development, creating vaccines, producing and purifying proteins, and developing other biologicals. To be safe and effective for their intended use, these base materials must be pure and sterile. As such, base materials are typically made by specialized manufacturers or end-users that have made large investments in sophisticated equipment and facilities. Such equipment and facilities are operated under highly controlled procedures that are regulated by the Food and Drug Administration (FDA) and other related agencies.

For example, most of the base materials are hydrated in large stainless steel tanks where purified water is combined with a precise amount of a desired base material in its powdered form. Some supplements may be added in liquid form as well. A special mixer is then used to mix the components into the desired end solution. Once the solution is prepared, the solution is filtered and may be directly used or dispensed and sealed into sterile containers for shipment or storage. The entire system is typically operated in some form of clean room.

Between the production of different batches of materials, the mixing tanks, mixers, and all other reusable components that contact the solution must be carefully cleaned to avoid any cross contamination. The cleaning of the structural components is labor intensive, time consuming, and costly. For example, depending on the structural component and the material being produced, cleaning can require the use of chemical cleaners such as sodium hydroxide and may require steam sterilization as well. The use of chemical cleaners has the additional challenge of being relatively dangerous to use and cleaning agents can be difficult and/or expensive to dispose of once used.

Due to the huge expense in creating, operating, and maintaining the elaborate systems used in the manufacture of base materials, biotech companies frequently purchase the base materials in their final solution form. There are, however, certain drawbacks to this strategy. For example, the base materials in the solution form are primarily water. As such, these materials can be difficult and expensive to transport.

Furthermore, although the powdered base materials can be stored for an extended period of time under relatively ambient conditions, the final liquid solutions must typically be stored under refrigerated conditions and have a significantly shorter shelf life. Due to the required refrigeration, storage of significant amounts of the base materials in their solution form can be expensive.

Accordingly, what is needed are systems and components of such systems that enable an end user to hydrate its own base materials into solution form based on its immediate needs but which do not require the highly regulated and labor intensive cleaning and sterilization processes used by typical manufactures. Such systems would enable the end user to minimize the storage of large amounts of base material in solution form while enabling it to maximize the use of powdered base materials which are more efficient to transport and store. Manufacturers could also use such systems to simplify their manufacturing processes.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 1 is an elevated front view of one embodiment of a fluid preparation system;

FIG. 2 is a cross sectional top view of the tank assembly taken along section lines 2—2 of FIG. 1;

FIG. 2A is an enlarged section view of the tank assembly shown in FIG. 2;

FIG. 3 is a partially cut away side view of the side wall of the tank assembly shown in FIG. 1 illustrating fluid channels therein;

FIG. 4 is a cross sectional side view of the tank assembly taken along section lines 4—4 of FIG. 2;

FIG. 9 is an elevated side view of a panel of the mixing bag shown in FIG. 8;

FIG. 10A is a cross sectional side view of the top end of the mixing bag shown in FIG. 8;

FIG. 10B is a cross sectional side view of an alternative embodiment of the top end of the mixing bag shown in FIG. 8;

FIG. 36 is an elevated side view of a delivery assembly and a collector assembly operable with a sterilizer;

FIG. 37 is a cross sectional side view of a fill tube of the delivery assembly shown in FIG. 36;

FIG. 38 is an end view of the fill tube shown in FIG. 37;

DETAILED DESCRIPTION OF THE PREFERRED EMBODIMENTS

Figures 5A, 5B:
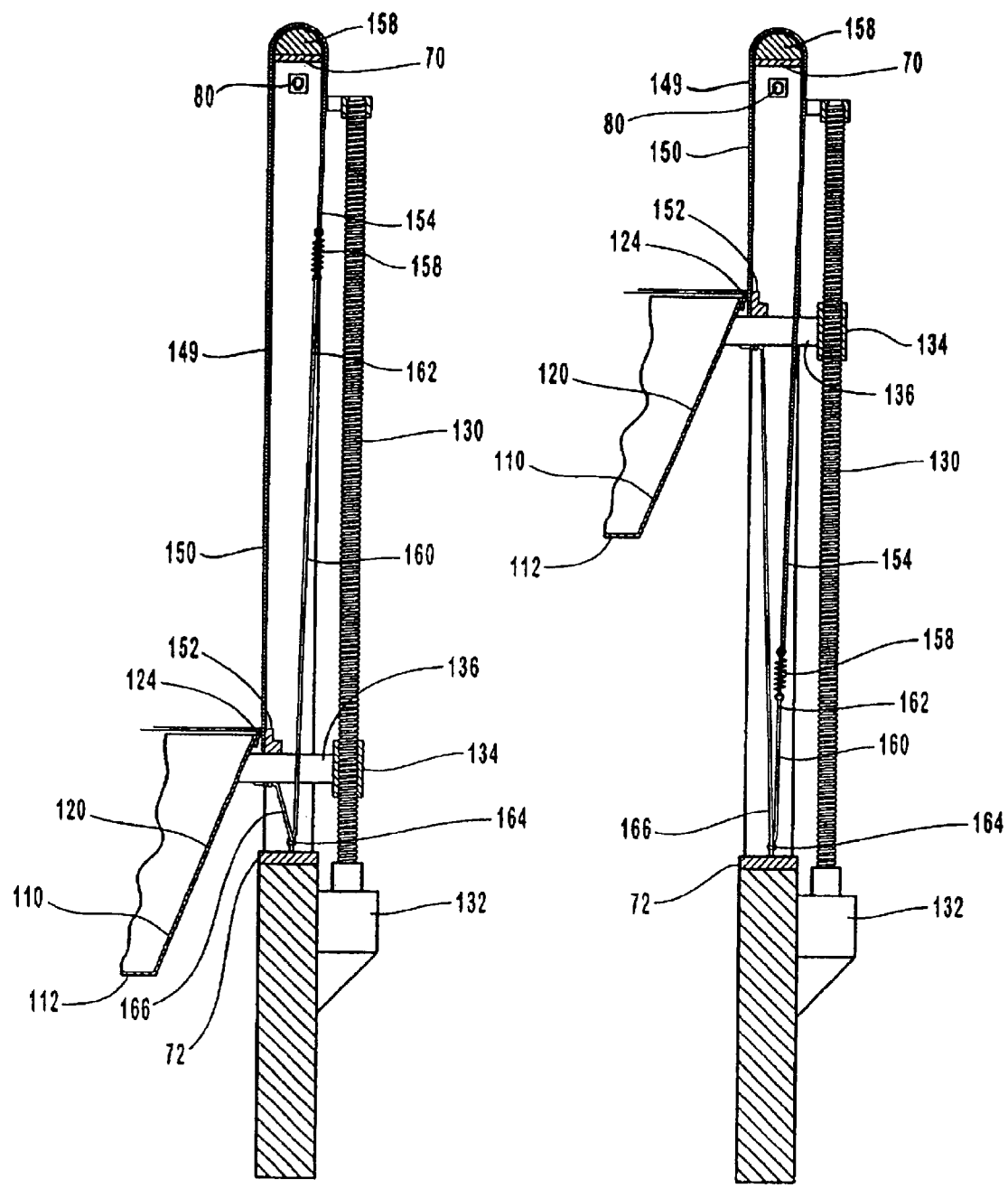
FIG. 5A is a cross sectional side view of the tank assembly taken along section lines 5—5 of FIG. 2.
FIG. 5B is the same cross sectional side view shown in FIG. 5A with the floor therein being raised.

Depicted in FIG. 1 is one embodiment of a fluid preparation system 10 incorporating features of the present invention. Fluid preparation system 10 is used for mixing two or more components, at least one of the components being liquid, so as to produce a homogeneous solution. Although each of the components can be liquid, in one typical embodiment one component is a substantially dry material such a powder, grain, granule or other form of solid while the other component is a liquid such as water. Fluid preparation system 10 can be used in producing any form of solution including those which are sterile and those which are non-sterile. In one common embodiment, fluid preparation system 10 is used in the manufacture of culture media, buffers, reagents and other biological materials that may or may not be sterile.

In one embodiment fluid preparation system 10 is designed so that structural components of the system that are directly in contact with the solution are disposable. Accordingly, as fluid preparation system 10 is shifted between the manufacture of different batches or types of solutions, the contaminated components are simply replaced with new components. Depending on the component and the intended solution, the new component can be sterile or non-sterile. As a result, multiple different solutions can be manufactured relatively quickly without the down time and added expense of sterilization or cleaning of the system. In other embodiments, however, select or all of the components of the system can be designed for sterilization and reuse.

In general, though not required or exclusive, fluid preparation system 10 comprises a tank assembly 20 mounted on a platform 12, a mixing assembly 200 at least partially disposed within tank assembly 20, a filtration system 500 in fluid communication with mixing assembly 200, and a dispensing system 700 in fluid communication with filtration system 500.

In the embodiment depicted in FIG. 1, fluid preparation system 10 includes movable platform 12 on which all or some of the components of fluid preparation system 10 are mounted. If desired, some or all of the system components can be mounted on platform 12 at a manufacturing facility prior to shipping and final assembly at an end user location. Fluid preparation system 10 can thus be formed as a modular unit that is relatively easily moved between different facilities. Alternatively, the various components can be mounted on and/or about platform 12 at the end user location. In another embodiment, it is appreciated that platform 12 is not required and that fluid preparation system 10 can be permanently or otherwise assembled at an end user facility.

I. Tank Assembly.

A. Side Wall.

Tank assembly 20 comprises a plurality of legs 22 upstanding from platform 12 and supporting an annular side wall 24. As shown in FIGS. 1 and 2, side wall 24 has an interior surface 26 and an exterior surface 28 each extending between an upper end 30 and an opposing lower end 32. Interior surface 26 at least partially bounds a chamber 60. Side wall 24 has a tubular configuration so that upper end 30 and lower end 32 are open.

Side wall 24 comprises a body portion 23 having a substantially C-shaped transverse cross section. Body portion 23 terminates at substantially opposingly facing end plates 54 and 56 with a doorway 57 formed therebetween. Although not required, to increase the hoop strength of body portion 23, a support brace 58 rigidly extends between end plates 54 and 56 at lower end 32.

Body portion 23 comprises an outer wall 34, a concentrically disposed inner wall 36 and a central wall 38 concentrically disposed between outer wall 34 and inner wall 36. Each of walls 34, 36, and 38 connect with each of end plates 54 and 56. Disposed between outer wall 34 and central wall 38 is an insulation layer 40. In one embodiment, insulation layer 40 comprises a chloride free, ceramic fiber capable of withstanding temperatures up to 1,300° C. Other conventional types of insulation can also be used. Extending between central wall 38 and inner wall 36 are a plurality of spaced apart spacers 42. Spacers 42 can comprise discrete members or formations projecting from central wall 38 and or inner wall 36. Spacers 42 provide structural stability for both central wall 38 and inner wall 36 while forming fluid channels 44 which allow fluid to flow between central wall 38 and inner wall 36 and around spacers 42.

More specifically, depicted in FIG. 3 is a cutaway view showing the outside face of inner wall 36 with spacers 42 projecting therefrom. Each of inner wall 36, central wall 38, and out wall 34 extend between and rigidly connect with a top plate 70 and an opposing bottom plate 72. In one embodiment, support brace 58, previously discussed, can be integrally formed with bottom plate 72. As will be discussed below in greater detail, a plurality of vertically oriented spaced apart slots 68 extend through body portion 23 from toward bottom plate 72 to toward top plate 70. Slots 68 generally divide body portion 23 into a plurality of sections 74. Each of inner wall 36, central wall 38, and outer wall 34 also connect with side plates 76 and 78 that bound each side of each slot 68. As a result, fluid channels 44 are sealed closed in each section 74 of body portion 23.

To facilitate fluid communication between fluid channels 44 of each section 74, a transition pipe 80 extends between each section 74 at upper end 30. Each opposing end of transition pipe 80 is in fluid communication with a corresponding fluid channel 44. As also depicted in FIG. 3, a plurality of spaced apart, vertically oriented channeling ribs 82 extend between inner wall 36 and central wall 38. Channeling ribs 82 are positioned such that as fluid flows radially about body portion 23, the fluid is also forced to flow in a sinusoidal path along the height of body portion 23.

Specifically, as depicted in FIGS. 1 and 2, a fluid inlet pipe 62 is connected with body portion 23 at lower end 32 adjacent to end plate 54 while a fluid outlet pipe 64 is connected with body portion 23 at lower end 32 adjacent to end plate 56. Each of inlet pipe 62 and outlet pipe 64 are in fluid communication with fluid channels 44. As fluid is pumped into fluid inlet pipe 62, the fluid enters a fluid channel 44 through an inlet port 66 in FIG. 3. As a result of being bounded between side plate 76 and end plate 54, the fluid travels vertically upward and around spacers 42.

When the fluid reaches upper end 30, the fluid passes through transition pipe 80 into the next adjacent section 74. As the fluid continues to travel around body portion 23 toward fluid outlet pipe 64, the fluid continues to vertically travel up and down so as to pass around channeling ribs 82. Once the fluid reaches and is removed from body portion 23 through fluid outlet pipe 64, the fluid is then heated or cooled, depending on desired operating parameters, and then reintroduced back through fluid inlet pipe 62. In one embodiment, the fluid passing through fluid channels 44 is a mixture of water and propylene glycol. In other embodiments, the fluid can be any material that can be used for heating and/or cooling.

In one embodiment of the present invention, means are provided for selectively heating or cooling a solution held within chamber 60 of tank assembly 20. One example of such means comprises fluid channels 44 and related structure as discussed above. As will be discussed below in greater detail, during operation a solution is disposed within chamber 60. By running a fluid through fluid channels 44 with the fluid at a desired temperature, the fluid acts as either a heat sink by drawing energy from the solution through inner wall 36 or as a heat source by inputting energy into the solution through inner wall 36, thereby heating or cooling the solution.

In part, channeling ribs 82 function to uniformly distribute the fluid over the exterior surface of inner wall 36 so as to uniformly control the temperature of the solution within chamber 60. In this regard, channeling ribs 82 and fluid channels 44 can be oriented to flow in a variety of different paths. Furthermore, body portion 32 can be formed without channeling ribs 82.

In yet other alternative embodiments for the means for selectively heating and cooling, open fluid channels 44 can be replaced with piping that runs on the interior, exterior, and/or within inner wall 36. The piping is configured to have the heating or cooling fluid run therethrough. Electrical heating elements can also be positioned on the interior, exterior, and/or within the inner wall 36 to facilitate heating of solutions within chamber 60. In yet another embodiment, the solution within chamber 60 can be pumped out of chamber 60 where it is then selectively heated or cooled through conventional systems and then cycled back into chamber 60.

As depicted in FIGS. 1, 2 and 2A, side wall 24 also comprises a door 25 disposed within doorway 57 between end plates 54 and 56. As with body portion 23, door 25 comprises an outer wall 34 and an inner wall 36. In this embodiment, however, door 25 does not include a central wall 38. Rather, a layer of insulation 40 is disposed between walls 34 and 36. In an alternative embodiment, door 25 can also include fluid channels 44 which communicate with body portion 23 through flexible hose connections.

A vertically oriented, elongated viewing slot 46 extends through a portion of door 25. A window 48 is disposed within viewing slot 46 so as to seal viewing slot 46 closed but provide an unobstructed view of chamber 60. Door 25 is mounted to body portion 23 by hinges 50. A handle 52 is formed on door 25 to facilitate hinged movement of door 25 between an open position (not shown) wherein free access is provided to chamber 60 through open doorway 57 and a closed position wherein door 25 closes off doorway 57.

In one embodiment of the present invention, means are provided for selectively locking door 25 in the closed position. By way of Example and not by limitation, as depicted in FIGS. 2A and 4, a vertically oriented, tubular housing 90 is movable mounted along end plate 56 of body portion 23. Housing 90 has a front face with a plurality of vertically spaced apart stops 102 formed thereon. Each stop 102 has an engagement face 104 that slopes toward chamber 60.

An actuation rod 92 extends through housing 90 in parallel alignment therewith. Actuation rod 92 is rigidly secured to housing 90 by bolts 94 or the like and extends between a first end 96 and an opposing second end 98. First end 96 of actuation rod 92 projects up above tubular housing 90. Second end 98 of actuation rod 92 is coupled with a hydraulic piston 100 disposed below support brace 58. By selectively operating hydraulic piston 100, actuation rod 92 is selectively raised and lowered which in turn selectively raises and lowers housing 90.

Projecting from a side face 105 of door 25 are a plurality of vertically oriented and spaced apart locking flanges 106. Each locking flange 106 is separated by a gap 108. To facilitate locking of door 25, actuation rod 92 is moved to a lowered position and door 25 is moved to the closed position. In this configuration, locking flanges 106 are disposed between stops 102. Hydraulic piston 100 is then used to elevate actuation rod 92. In so doing, housing 90 and stops 102 rise so that engagement face 104 of each stop 102 biases against a corresponding locking flange 106. Engagement faces 104 are sloped so as to bias locking flanges 106 radially inward, thereby locking door 25 closed. To further secure this locking, a plate 108 having a hole extending therethrough projects from the upper end of door 25. When door 25 is in the closed position the hole in plate 108 is aligned with actuation rod 92. As actuation rod 92 rises, first end 96 of actuation rod 92 passes through the hole in plate 108.

It is appreciated that the means for selectively locking door 25 can have a variety of alternative configurations. By way of example and not by limitation, hydraulic piston 100 can be replaced by a pneumatic piston, gear or belt drive, crank, jack, or other drive mechanism. Furthermore, is appreciated that locking flanges 106 and stops 102 can be switched or replaced with a variety of other conventional interlocking members. In other embodiments, a variety of shafts can be positioned so as to selectively drive from one of door 25 or body portion 23 into or against the other thereof. Hand operated dead bolts and other conventional locking strictures can also be used.

B. Floor.

Returning back to FIGS. 1 and 2, tank assembly 20 further comprises a floor 110 disposed within or within alignment of the interior of side wall 24. Floor 110 comprises a substantially flat base floor 112. In the embodiment depicted, base floor 112 is circular and extends to a perimeter edge 114. As will be discussed below in greater detail, a plurality of open port holes 116 extend through base floor 112. A central port hole 117 also extends through base floor 112. Although not required, a plurality of screened spill holes 118 are also formed on base floor 112.

A peripheral wall 120 upwardly and outwardly slops from perimeter edge 114 of base floor 112 to a terminal edge 122. Outwardly projecting from terminal edge 122 is a lip 124. Lip 124 is either biased directly against or terminates directly adjacent to interior surface 26 of side wall 24. Except for lip 124, the remainder of floor 110 and the walls of side wall 24 are typically made of a metal such as stainless steel. In contrast, lip 124 is typically made of polypropylene but can also be made of resilient materials such as rubber, silicone, Vitor, Teflon, and other moldable plastics.

In the embodiment depicted, floor 112 has a substantially frustoconical configuration. In alternative embodiments, floor 112 can be entirely flat, curved, pyramidal, conical, or any other desired configuration that can support a bag as discussed below. Furthermore, floor 112 need not be circular but can be polygonal, elliptical, irregular, or any other desired configuration.

In one embodiment of the present invention, means are provided for selectively raising and lowering floor 112 relative to side wall 24. By way of example and not by limitation, rotatably mounted on the exterior of side wall 24 in vertical alignment with each slot 68 thereof is a threaded shaft 130. In one embodiment, a driver 138 is mounted at the bottom of each shaft 130 to selectively rotate each shaft 130. A collar 134 encircles and threaded engages each shaft 130 such that rotation of each shaft 130 causes each corresponding collar 134 to advance up or down the length of shaft 130, depending on the direction of rotation, in a worm drive configuration. A strut 136 extends between floor 120 and each collar 134 so as to pass through a corresponding slot 68. As a result, simultaneous rotation of each shaft 130 facilitates uniform raising and lowering of floor 112 relative to side wall 24. By adjusting the level of floor 112, the size of chamber 60 bounded by side wall 24 and floor 60 is selectively adjusted, i.e., the size of chamber 60 gets smaller as floor 112 rises.

It is appreciated that the means for selectively raising and lowering floor 112 can comprises a variety of modified and alternative configurations. For example, rather than having a separate driver 132 for each threaded shaft 130, a single driver 132 can be used which is connected by drive lines 140 (shown in FIG. 2) to each separate threaded shaft 130. In yet other modifications, shaft 130 and collars 134 can be replaced with one or more conventional chain drives, belt drives, gear drives, hydraulic lifts, pneumatic lifts, jacks, cranks, winches, pulley systems and/or combinations thereof and the like for selectively raising struts 136 from the exterior of side wall 24. Furthermore, the above discussed various lifts and jacks can be placed directly below floor 112 for selectively raising and lowering floor 112. In these embodiments, struts 136 and slots 68 are not required but may be used for stabilizing.

C. Slot Cover Assembly.

In one embodiment of the present invention, means are provided for selectively covering and uncovering portions of slots 68 within chamber 60. As will be discussed below in greater detail, because a bag or other form of liner is typically disposed within chamber 60 of tank assembly 20, in one embodiment it is desired, although not required, that a cover be disposed over that portion of slots 68 that is exposed above floor 110 so that the bag or liner does not bulge out of or catch on slots 68 and potentially fail. As depicted in FIGS. 5A and 5B, one example of such means comprises a slot cover assembly 149 that includes an elongated flexible slot cover 150 having a first end 152 and an opposing second end 154. Slot cover 150 has a width slightly larger than slot 68 (as seen in FIG. 2) and a thickness which is typically in a range between about 2 mm to about 10 mm. Other desired thicknesses can also be used.

First end 152 of slot cover 150 is positioned against or adjacent to interior surface 26 of side wall 24 at or adjacent to lip 124 of floor 110. In one embodiment, at least a portion of first end 152 of slot cover 150 is disposed between lip 124 and side wall 24. First end 152 of slot cover 150 is held in position by a bracket 156 mounted on strut 136. Alternatively, slot cover 150 can be mounted directly to floor 110 or strut 136. From first end 152, slot cover 150 freely travels upward so as to movably and substantially cover that portion of slot 68 above floor 110. A rounded support 158 is mounted on top plate 70 of body portion 23. Slot cover 150 passes over rounded support 158 and travels down along the exterior of side wall 24 to second end 154.

Slot cover assembly 149 also includes a tensioning spring 158 and a line 160. One end of tensioning spring 158 is connected to second end 154 of slot cover 150. A first end 162 of line 160 is connected to the opposing end of tensioning spring 158. Line 160 extends down through a support loop 164 mounted on base plate 72 of body portion 23. A second end 166 of line 160 then connects back to strut 136 such as by bolting, welding, bracket, or the like. Since slot cover assembly 149 forms a continuous loop with opposing ends connecting to strut 136, raising or lowering of floor 110 causes slot cover 150 to move along and continuously cover slot 68 above lip 124 of floor 110. This configuration, however, also allows slot 68 below lip 124 of floor 110 to be open so as to allow the free travel of strut 136 therein.

Line 160 of slot cover assembly 149 can be wire, cable, rope or the like. In an alternative embodiment, line 160 can be replaced with the same material as slot cover 150. Line 160 is simply used so as to be less obstructive. In yet other embodiments of the means, a spring tensioned coil, electrical winch, or the like can be disposed on the top or outside of side wall 23 so as to selectively gather and release slot cover 150 as floor 110 is selectively raised and lowered.

D. Mixer Drivers.

As depicted in FIG. 1, extending through central port hole 117 of floor 110 (FIG. 2) is a mixing shaft 208. As will be discussed and depicted below in greater detail, a mixer is mounted on the first end of mixing shaft 208 within chamber 60. In one embodiment of the present invention, means are provided for selectively raising and lowering mixing shaft 208. By way of example and not by limitation, a frame 168 is mounted to and extends below floor 110. Mounted to frame 168 is a hydraulic piston 170 which operates an actuation rod 172. In turn, a coupler 176 removably connects actuation rod 172 to mixing shaft 208. Flexible hydraulic hoses 174 provide hydraulic fluid to hydraulic piston 170 for raising and lowering actuation rod 172 and thus mixing shaft 208. As a result of hydraulic piston 170 being mounted to floor 110 by way of frame 168, hydraulic piston 170 raises and lowers with floor 110.

It is appreciated that there are a number of alternative embodiments of the means for selectively raising and lowering mixing shaft 208. By way of example and not by limitation. Hydraulic piston 170 can be mounted on platform 12 or a ground surface. This embodiment is more practical where floor 110 is fixed. Furthermore, hydraulic piston 170 can be replaced with a number of other forms of drivers such as a pneumatic piston, rotating crank, various forms of belt drivers, chain drivers, or gear drivers, or other well known mechanisms that enable repeated raising and lowering of a shaft. It is also appreciated that such drivers can be directly connected to mixing shaft 208 or can be connected thereto through actuation rod 172.

E. Fixed Tank Configuration

Figure 7:
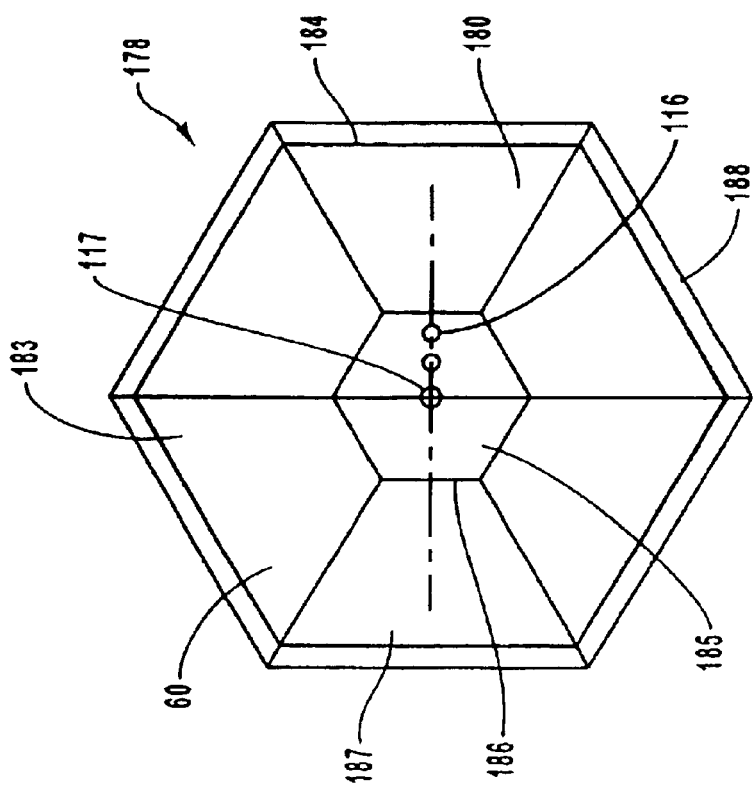
FIG. 7 is a top plan view of the tank assembly shown in FIG. 6.
Figure 6:
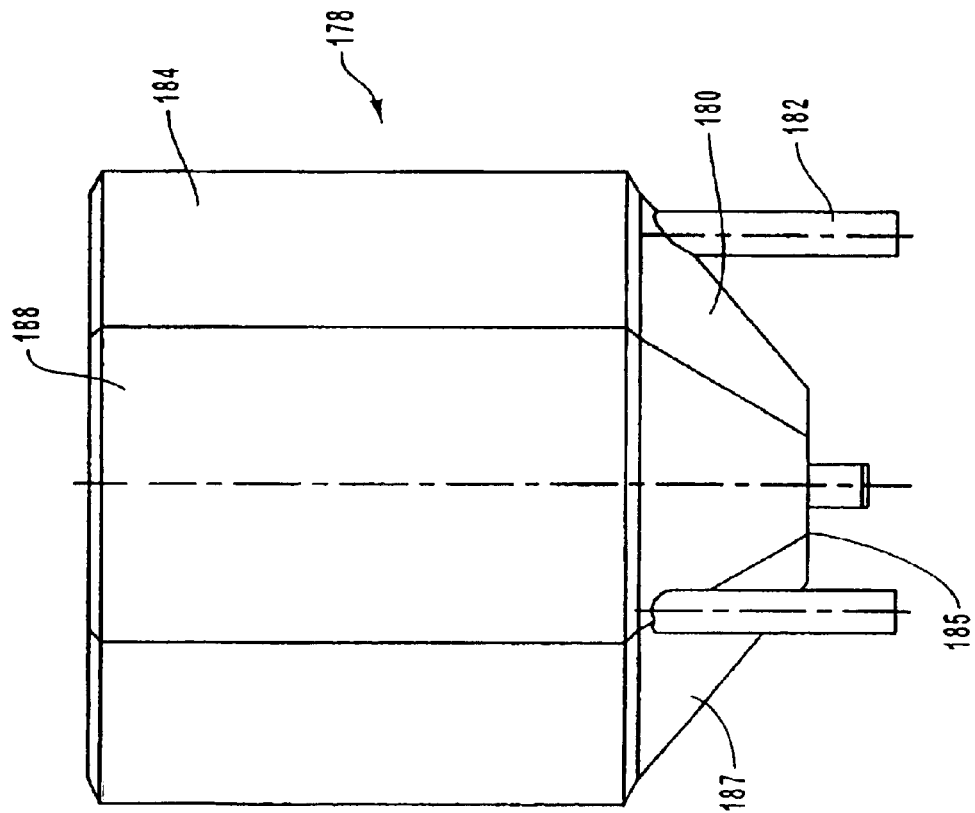
FIG. 6 is an elevated front view of an alternative embodiment of a tank assembly.

In alternative embodiments of tank assembly 20, it is appreciated that floor 110 need not be adjustable nor does tank assembly 20 need to be able to heat or cool the solution disposed therein. For example, depicted in FIGS. 6 and 7 is a tank assembly 178. Tank assembly 178 comprise a substantially frustoconical floor 180 having a plurality of support legs 182 downwardly extending therefrom. Rigidly connected to and upwardly extending from the perimeter of floor 180 is an annular side wall 184. Floor 180 and side wall 184 bound a chamber 183.

Floor 180 comprises a central base floor 185 having port holes 116 and central port hole 117 extending therethrough. Base floor 185 has a hexagonal configuration that terminates at a plurality of perimeter edges 186. A trapezoidal shaped floor panel 187 upwardly extends at an angle from each perimeter edge 186 of base floor 185. Each of floor panels 187 are secured, such as by welding, bolting, or the like, to the adjacent floor panels 187. The resulting floor 185 thus has a substantially frustoconical configuration with an interior surface, an exterior surface, and a perimeter edge each having a substantially hexagonal transverse cross section.

Side wall 184 comprises a plurality of side panels 188 each having a substantially rectangular configuration. Each side panel 188 is rigidly connected to and upwardly extends from an outer perimeter edge of a corresponding floor panel 187. Again, adjacent side panels 188 are connected to each other and to floor panels 187 such as by welding, bolting, or the like. Side wall 184 thus has an interior surface and an exterior surface each having a substantially hexagonal transverse cross section along the length of side wall 184.

In contrast to tank assembly 20, floor 180 and side wall 184 of tank assembly 178 are made of solid sheets of metal or other material and thus do not bound fluid channels 44 nor do they have slots 68 extending therethrough. Furthermore, side wall 184 does not include a door or window. Finally, floor 180 is rigidly connected to side wall 184 and thus does not raise or lower relative to side wall 184.

In both tank assembly 20 and tank assembly 178, the side wall and floor can be any desired configuration such as elliptical, polygonal, irregular, or any other desired configuration. The floor typically has a configuration complementary to the side wall. In alternative embodiments, it is appreciated that the various features of tank assemblies 20 and 178 can be mixed and matched so as to produce a variety of tank assembly configurations having different properties. For example, a tank assembly can be made to heat or cool a solution but have a fixed floor that does not raise or lower. Furthermore, tank assemblies can be made in any number of different sizes. For example, tank assemblies can be made with a chamber having a volume of 20 liters, 250 liters, 500 liters, 750 liters, 1,000 liters, 1,500 liters, 3,000 liters, 5,000 liters, 10,000 liters or other sizes. In addition, fluid preparation system 10 can comprise two or more tank assemblies of the same or different size, shape, and/or properties that are mounted on or off of platform 12.

II. Mixing Assembly.

Figure 8:
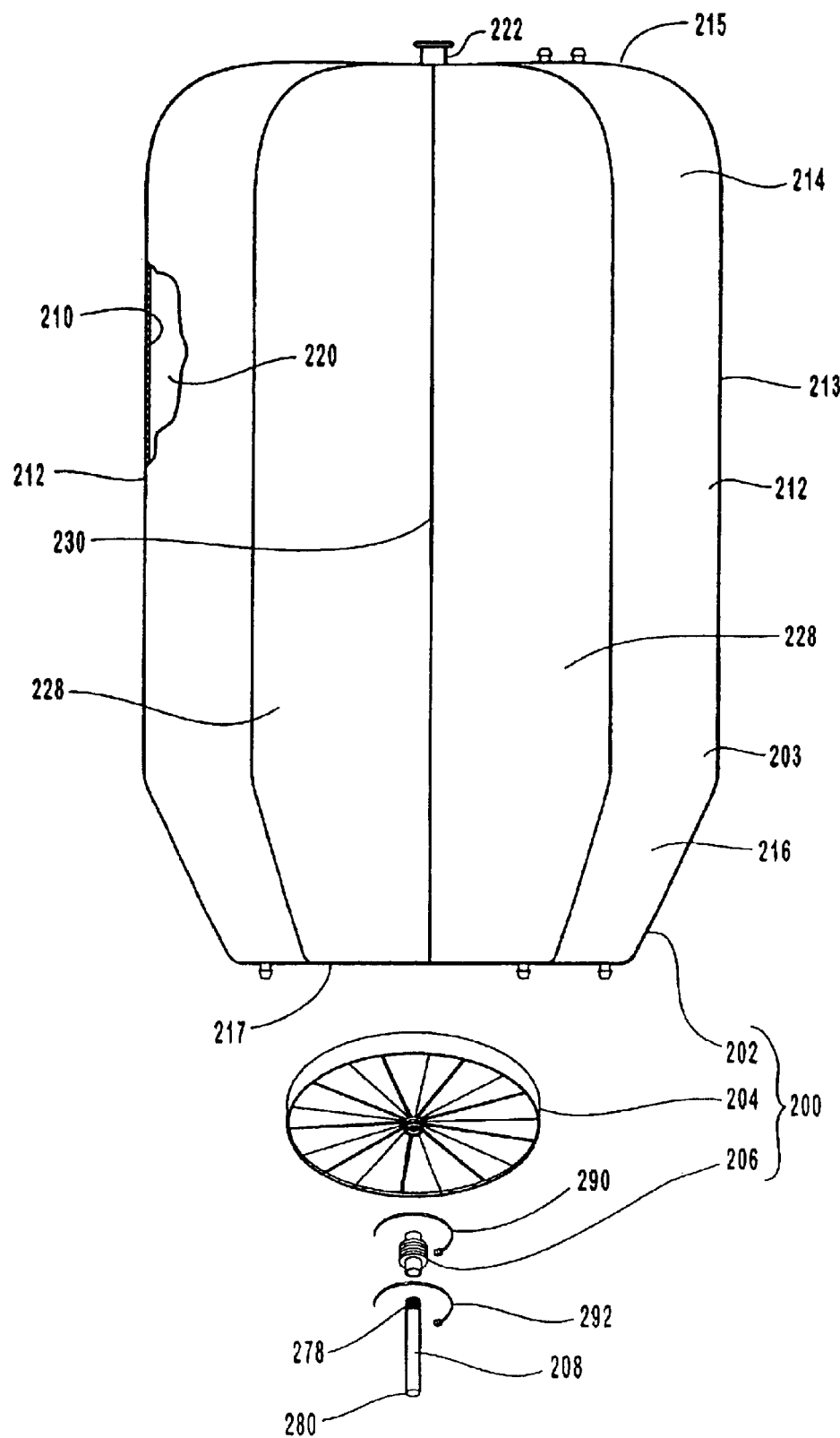
FIG. 8 is an exploded partial perspective view of a mixing bag assembly.

Depicted in FIG. 8 is one embodiment of a mixing assembly 200. In general, though not required or exclusive, mixing assembly 200 comprises a mixing bag 202, a mixer 204 configured to be disposed within mixing bag 202, and an expandable tubular seal 206 configured to provide a fluid sealed connection between mixing bag 202 and mixer 204. In alternative embodiments, mixing shaft 208, as previously discussed, can either be part of or separate from mixing assembly 200.

A. Mixing Bag.

As depicted in FIG. 8, mixing bag 202 comprises an elongated, bag-like body 203 having an interior surface 210 and an exterior surface 212. Interior surface 210 bounds a compartment 220. More specifically, body 203 comprises a side wall 213 that, when body 203 is inflated, has a substantially circular or rounded polygonal transverse cross section that extends between an upper end 214 and an opposing lower end 216. Upper end 214 terminates at a top end wall 215 while lower end 216 terminates at a bottom end wall 217.

Body 203 is comprised of a flexible, water impermeable material such as polyethylene, polyurethane or other polymeric sheets having a thickness in a range between about 0.1 mm to about 5 mm with about 0.2 mm to about 2 mm being more common. Other thicknesses can also be used. In one embodiment, the material is approved for direct contact with living cells and is capable of maintaining a solution sterile. In such an embodiment, the material should also be sterilizable such as by ionizing radiation. Examples of materials that can be used are disclosed in U.S. Pat. No. 6,083,587 which issued on Jul. 4, 2000 and U.S. patent application Ser. No. 10/044,636, filed Oct. 19, 2001 which are hereby incorporated by specific reference.

Body 203 can be comprised of a single ply material or can comprise two or more layers which are either sealed together or separated to form a double wall container. In one embodiment, body 203 comprises a two dimensional bag wherein trio sheets of material are placed in overlapping relation and the two sheets are bounded together at their peripheries to form internal compartment 220. In the embodiment depicted, however, body 203 comprises a three dimensional bag which not only has an annular side wall 213 but also a two dimensional top end wall 215 and a two dimensional bottom end wall 217.

Three dimensional body 203 comprises a plurality, i.e., typically three or more, discrete panels 228 as shown in FIG. 9. Each panel 228 is substantially identical and comprises a portion of the side wall 213a, top end wall 215a, and bottom end wall 217a. Corresponding perimeter edges of each panel 228 are seamed together to form seams 230 as shown in FIG. 8. Seams 230 are formed using methods known in the art such as heat energies, RF energies, sonics, or other sealing energies.

In alternative embodiments, panels 228 can be formed in a variety of different patterns. Further disclosure with regard to one method of manufacturing three-dimensional bags is disclosed in U.S. patent application Ser. No. 09/813,351, filed on Mar. 19, 2001 of which the drawings and Detailed Description are hereby incorporated by reference.

By using discrete panels 228, it is appreciated that body 203, and thus mixing bag 202, can be manufactured to have virtually any desired size, shape, and configuration. For example, mixing bag 202 can be formed having compartment 220 sized to hold 20 liters, 250 liters, 500 liters, 750 liters, 1,000 liters, 1,500 liters, 3,000 liters, 5,000 liters, 10,000 liters, or other desired amounts. Body 203 is often made of four or six panels 228 depending on the intended volume of mixing bag 202. Mixing bag 202 simply conforms to the configuration of tank assembly 20 as it is filled with solution. In one embodiment, however, mixing bag 202 can be specifically configured to be complementary to the interior surface of tank assembly 20 bounding chamber 60. For example, when interior surface of side wall 24 has a hexagonal configuration, mixing bag 202 can be made of six panels 228 so as to have a substantially hexagonal transverse cross section.

In either event, when mixing bag 202 is received within chamber 60, body 203 is uniformly supported by floor 110 and side wall 24 of tank assembly 20. This substantially uniform support of body 203 by tank assembly 20 helps to preclude failure of any mixing bag 202 by hydraulic forces applied to body 203 when mixing bag 202 is filled with a solution.

Depicted in FIG. 10A, mixing bag 202 further comprises a feeding port 222, a barbed fluid port 224, and an barbed pressure port 226 each mounted on top end wall 215 of body 203 so as to outwardly project therefrom. An annular flange 223 encircles and outwardly projects from the free end of feeding port 222. A channel 227 extends through each of ports 222, 224, and 226 so as to provide fluid communication between compartment 220 and the exterior.

A flexible extension sleeve 239 is received over feeding port 222 and is connected thereto by a tie 241. A tubular coupling 243 is mounted at the opposing end of sleeve 239 and is also secured thereto by a tie 241. A removable clamp 245 is closed across extension sleeve 239 so as to close off fluid communication between compartment 220 and the exterior. Extension tubes 249 and 251 are coupled to ports 224 and 226, respectively. A tie 241 can also be used to secure each of these connections. A removable clamp 244 is also closed across each tube 249 and 251 so as to seal off fluid communication between compartment 220 and the exterior.

Depicted in FIG. 10B is an alternative embodiment wherein like elements are identified by like reference characters. In this embodiment, extension sleeve 239 and clamp 244 have been replaced with a cover plate 232. Cover plate 232 is disposed within compartment 220 and is rotatably mounted to or adjacent to feeding port 222 by way of a knob 234. Selective rotation of a free end of knob 234 projecting outside of bag 202 facilitates rotation of cover plate 232 within compartment 220. Cover plate 232 can be rotated to selectively cover or expose channel 227 extending through feeding port 232.

Figure 11:
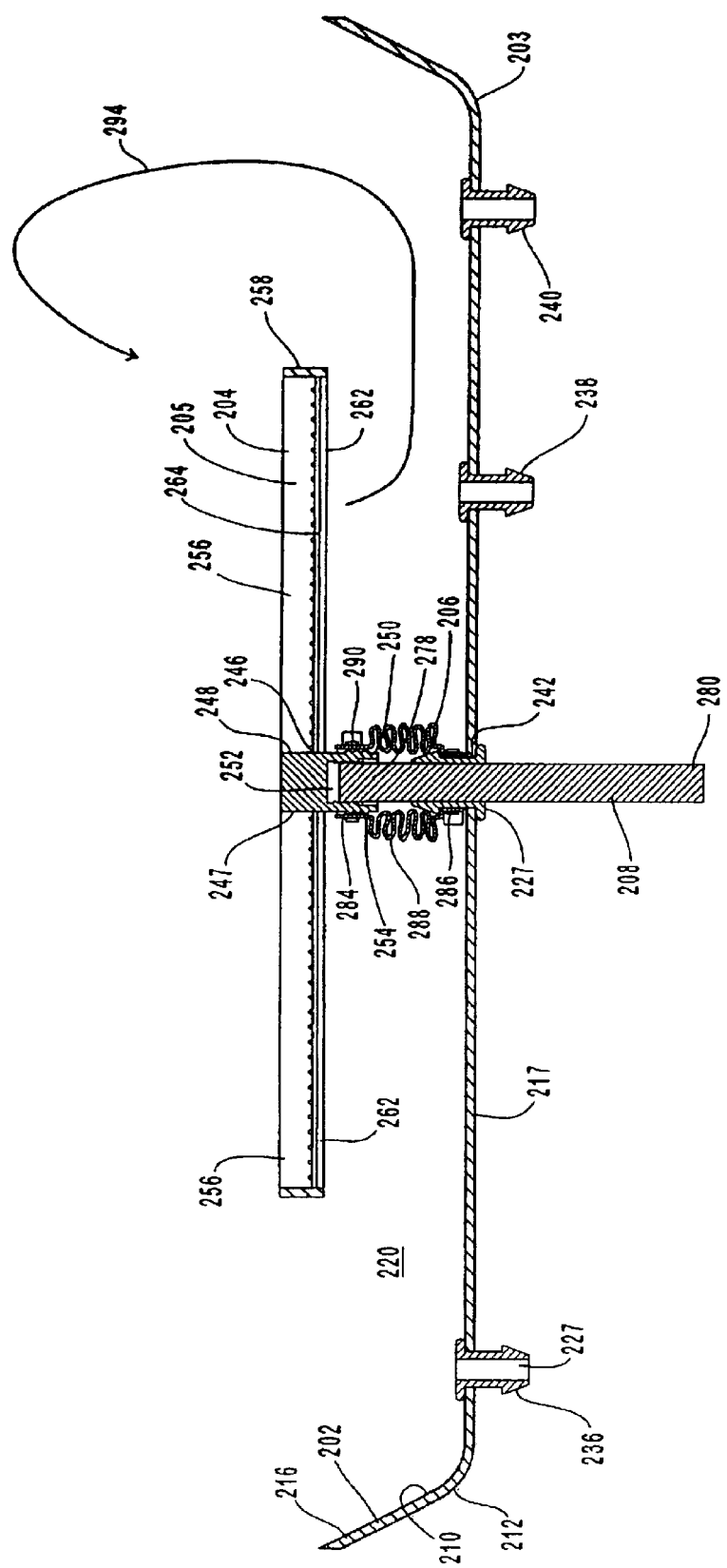
FIG. 11 is a cross sectional side view of the bottom end of the mixing bag shown in FIG. 8 with a mixer disposed therein.

Depicted in FIG. 11, mounted on bottom end wall 217 of body 203 so as to outwardly project therefrom is a barbed inflation port 236, a barbed outlet port 238, and a barbed inlet port 240. A barbed mounting port 242 is centrally disposed on bottom end wall 217 and projects into compartment 220. A channel 227 also extends through each of ports 236, 238, 240, and 242 so as to provide fluid communication between compartment 220 and the exterior. If desired, extension tubes with clamps thereon can be mounted on ports 236, 238 and 240, such as discussed with ports 224 and 226, so as to close communication with chamber 220 prior to use of mixing bag 202.

Although in the above discussed embodiments mixing bag 202 has a flexible, bag-like configuration, in alternative embodiments it is appreciated that mixing bag 202 can comprise any form of collapsible container or rigid container.

B. Mixer.

In one embodiment of the present invention means are provided for mechanically mixing a liquid solution with compartment 220 of mixing bag 202. By way of example and not by limitation, mixer 204 is disposed within compartment 220 of mixing bag 202. As depicted in FIG. 11, mixer 204 comprises a base 205 having flaps 264 mounted thereagainst. More specifically, base 205 comprises a central hub 246 having an exterior surface 247 extending between a first end 248 and an opposing second end 250. Second end 250 terminates at an end face having a threaded recess 252 formed thereon. Barbs 254 encircle and radially outwardly project from hub 246 at second end 250.

Figure 12:
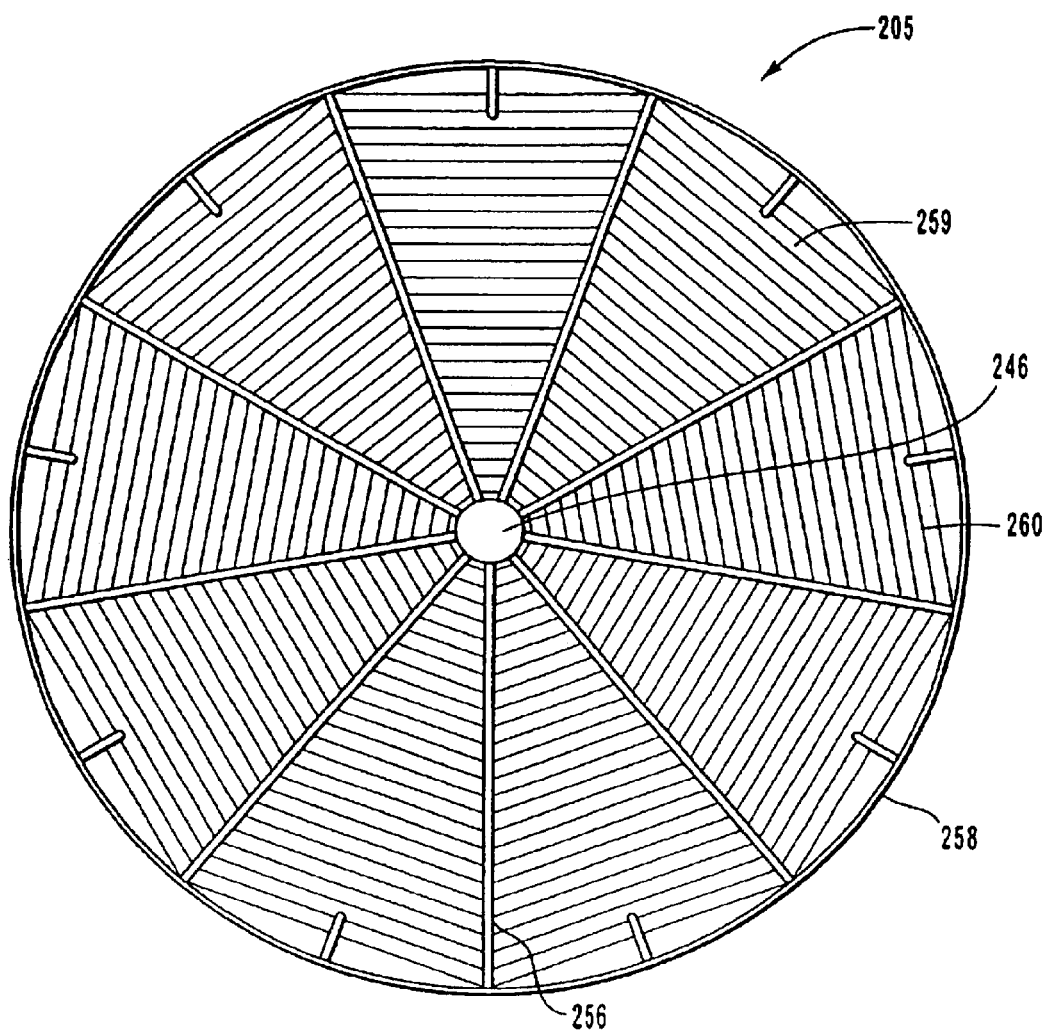
FIG. 12 is a top plan view of the mixer shown in FIG. 11.

As depicted in FIG. 12, base 205 further includes a plurality of spaced apart struts 256 that radially outwardly project from the exterior of hub 246 at first end 248 to an annular rim 258. A retention screen 260, supported on or by struts 256, extends between hub 246 and rim 258. Retention screen 260 bounds a plurality of fluid openings 259 formed between hub 246 and rim 258. In the embodiment depicted, retention screen 260 is comprised of wire or other line that is strung between struts 256. In alternative embodiments, retention screen 260 can comprise various forms of mesh, matting, conventional screen, plates having slots, holes, or other types of openings extending therethrough, or other similar types of structures that can support flaps 264, as discussed below, but which enable fluid to pass therethrough.

Figure 13A:
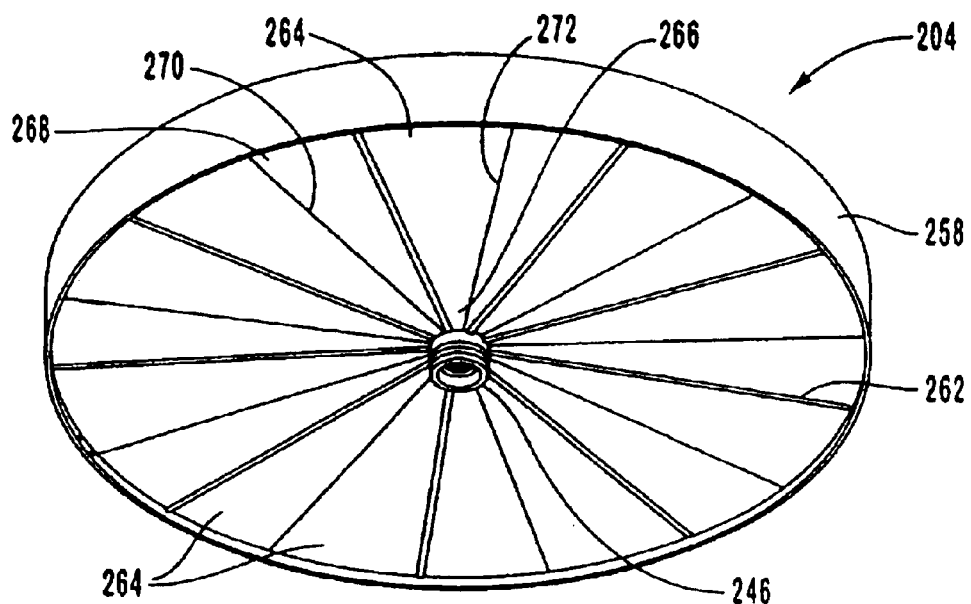
FIG. 13A is a bottom perspective view of the mixer shown in FIG. 11.

As depicted in FIGS. 11 and 13A, a plurality of spaced apart spokes 262 also extend between hub 246 and rim 258.

Each spoke 262 is aligned with a corresponding strut 256 on a side thereof closer to second end 250 of hub 246. Positioned between each spoke 262 and retention screen 260 is a flexible wedge shaped flap 264. Each flap 264 has a pointed lead end 266 disposed against or adjacent to hub 246 and a flared tail end 268 disposed adjacent to rim 258. Each flap 264 also comprises opposing diverging sides 270 and 272 that extend from lead end 266 to tail end 268. Each flap 264 is positioned so that a corresponding spoke 262 extends between lead end 266 and tail end 268 centrally between sides 270 and 272. Flaps 264 are configured to completely or at least substantially cover fluid openings 259 formed between hub 246 and rim 258 when flaps 264 rest against retention screen 260. In one embodiment, flaps 264 are comprised of a sheet of silicone having a thickness in a range between about 1 mm to about 10 mm. Other flexible sheets of material, such as polyethylene or polyurethane, having a variety of different thicknesses can also be used.

As shown in FIG. 11, mixer 204 is supported within compartment 220 of mixing bag 202 by mixing shaft 208. Specifically, mixing shaft 208 has a threaded first end 278 and an opposing second end 280. First end 278 of mixing shaft 208 slidably passes through channel 227 of mounting port 242 and then screws into threaded recess 252 of hub 246. Second end 280 of mixing shaft 208 is disposed outside of mixing bag 202.

In one embodiment of the present invention means are provided for raising and lowering mixer 204 within compartment 220 of mixing bag 202 so as to mix the solution within compartment 220. One embodiment of such means comprises mixing shaft 208 as discussed above. Alternative embodiments of such means include alternative mixing shafts as disclosed herein.

The present invention also includes means for enabling mixing shaft 208 to raise and lower mixer 204 within compartment 220 of bag 202 while preventing leaking of liquid from compartment 220 of mixing bag 202. By way of example and not by limitation, tubular seal 206 has a first end 284, an opposing second end 286, and an expandable bellow section 288 extending therebetween. First end 284 of seal 206 encircles second end 250 of hub 246. A surrounding tie 290 is used to secure the connection in a liquid tight fashion. Similarly, second end 286 of seal 206 encircles mounting port 242. A tie 292 is also used to secure this connection in a liquid tight fashion.

In the assembled configuration shown in FIG. 11, mixing shaft 208 can freely slide within channel 227 of mounting port 242 such that by selectively raising and lowering mixing shaft 208 from outside of mixing bag 202, mixer 204 is correspondingly raised and lowered within compartment 202 relative to mixing bag 202. Bellow section 288 of seal 206 selectively expands and contracts as mixing shaft 208 is raised and lowered relative to mixing bag 202, thereby maintaining the sealed communication between mixer 204 and mounting port 242.

Figure 13B:
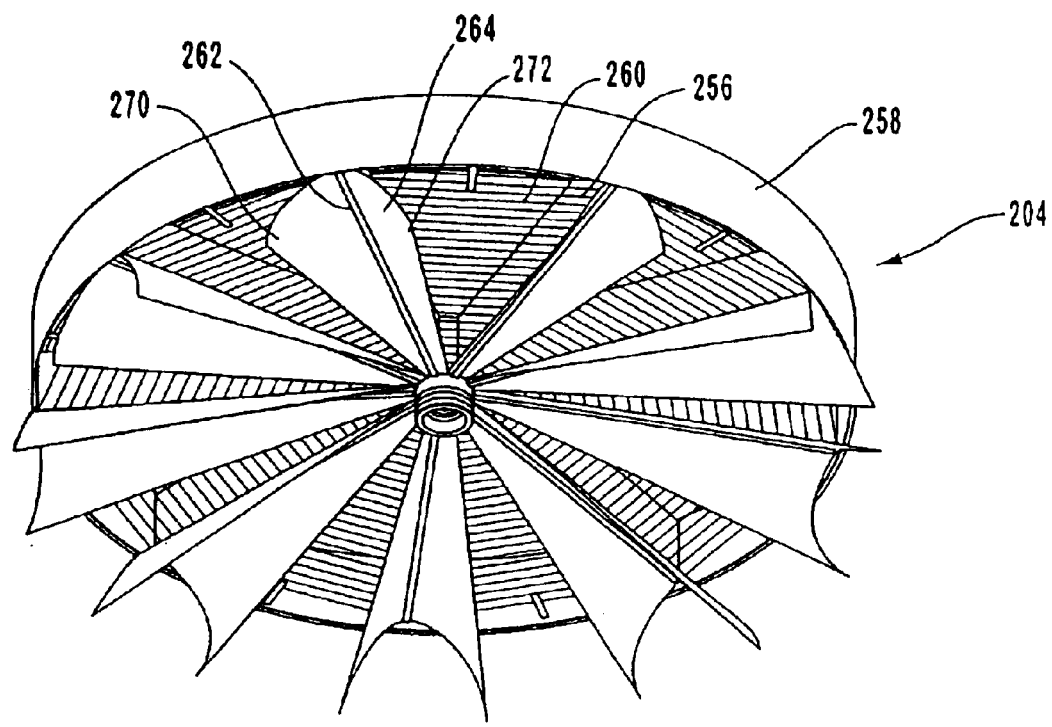
FIG. 13B is a bottom perspective view of the mixer shown in FIG. 13A with the flaps thereof being downwardly flexed.

As will be discussed below in greater detail, mixing of a solution within compartment 220 of mixing bag 202 is accomplished by repeatedly raising and lowering mixer 204 within compartment 220. As shown in FIG. 13B, as mixer 204 is raised, fluid within compartment 220 passes through retention screen 260 and pushes against flaps 264 causing sides 270 and 272 of flaps 264 on opposing sides of spokes 262 to downwardly flex, thereby allowing mixer 204 to travel through the fluid without substantial disturbance. As mixer 204 begins to travel downward, as shown in FIG. 13A, the fluid pushes flaps 264 against retention screen 260 so as to preclude the passage of the fluid through fluid openings 259 of mixer 204. As such, downward movement of mixer 204 causes the fluid within compartment 220 to flow down, out, up, and around as shown by arrow 294 in FIG. 11. As the process of raising and lowering mixer 204 is repeated, swirling motion of the solution caused by mixer 204 mixes the solution.

Mixing parameters can be varied based on the amount and type of solution being prepared. For example, the stroke length, i.e., the vertical distance that mixer 204 travels, and the frequency, i.e., the number of times mixer 204 travels the stroke length per unit of time, and the acceleration and deceleration, i.e., the rate at which mixer 204 starts and stops, can each be selectively regulated. The stroke length and frequency can not only be changed between different batches but can also be changed at different times during the mixing of a single batch. Furthermore, if desired, one or more of the variables can be continually changed during mixing.

In one embodiment, the parameters are set so as to enable rapid and thorough mixing of the components and yet be gentle enough to maintain suspensions for extended period of time without inducing excess foaming. By way of example and not by limitation, in one embodiment the stroke length is in a range between about 0.1 cm to about 30 cm with about 5 cm to about 20 cm being more common while the frequency is in a range between about 0.1 Hz to about 4 Hz with about 0.5 Hz to about 2 Hz being more common. Other parameter settings, however, can also be used based on the configuration of the mixer and the amount and type of solution being prepared.

It is appreciated that the means for mechanically mixing a liquid solution with compartment 220 of mixing bag 202 can comprise a variety of modifications or alternative embodiments of mixer 204. For example, in one embodiment mixer 204 can be flipped so that swirling is produced in an opposite direction. Furthermore, flaps 264 are simply functioning as a one-way valve. It is appreciated that there are a variety of alternative ways to form one-way valves on mixer 204. For example, rather than having flexible flaps 264, rigid flaps can be hingedly mounted on mixer 204. Furthermore, pneumatic, hydraulic, or electrical switches can be coupled with mixer 204 which selectively open and close one-way valves on mixer 204. In this embodiment, the one-way valves may simply comprise plates which selectively slide to open or close one or more holes extending through mixer 204.

In another alternative embodiment, it is appreciated that mixer 204 can be formed without one-way valves. For example, mixer 204 can comprise a rigid or flexible plate with no openings. In this embodiment, the plate swirls or otherwise mixes the solution as the plate moves in both directions. In yet another embodiments, the plate can have fixed holes or slots therein to direct movement of the fluid. Likewise, mixer 204 can simply comprise a plurality of fixed fins or vanes which can be configured to either rotate and/or move up and down within mixing bag 202 for mixing the solution. In still other embodiments, two or more mixers 204 can be mounted on mixing shaft 208. For example, the mixers 204 can be longitudinally spaced apart along shaft 208.

In other embodiments of the means for mixing, mixers can be used that do not operate by being raised and lowered. For example, shaft driven blades and magnetically operated stir bars that rotate within mixing bag 202 can be used.

Figure 14A:
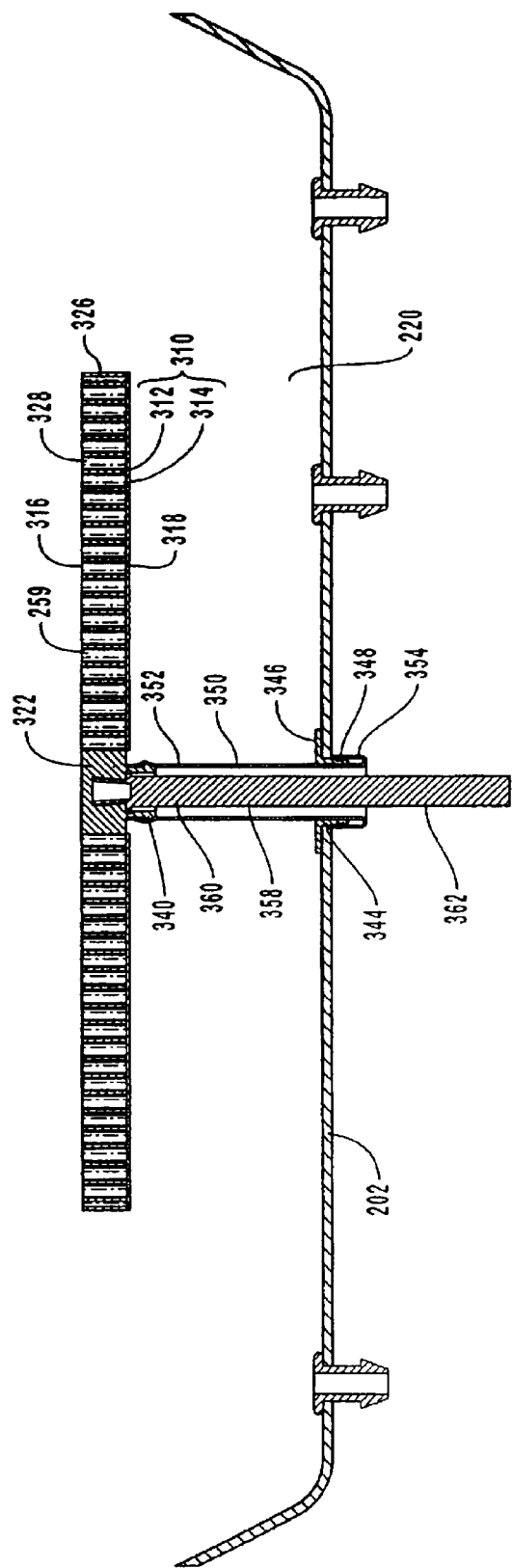
FIG. 14A is a cross sectional side view of the bottom end of the mixing bag shown in FIG. 8 with an alternative embodiment of a mixer disposed therein.
Figure 15:
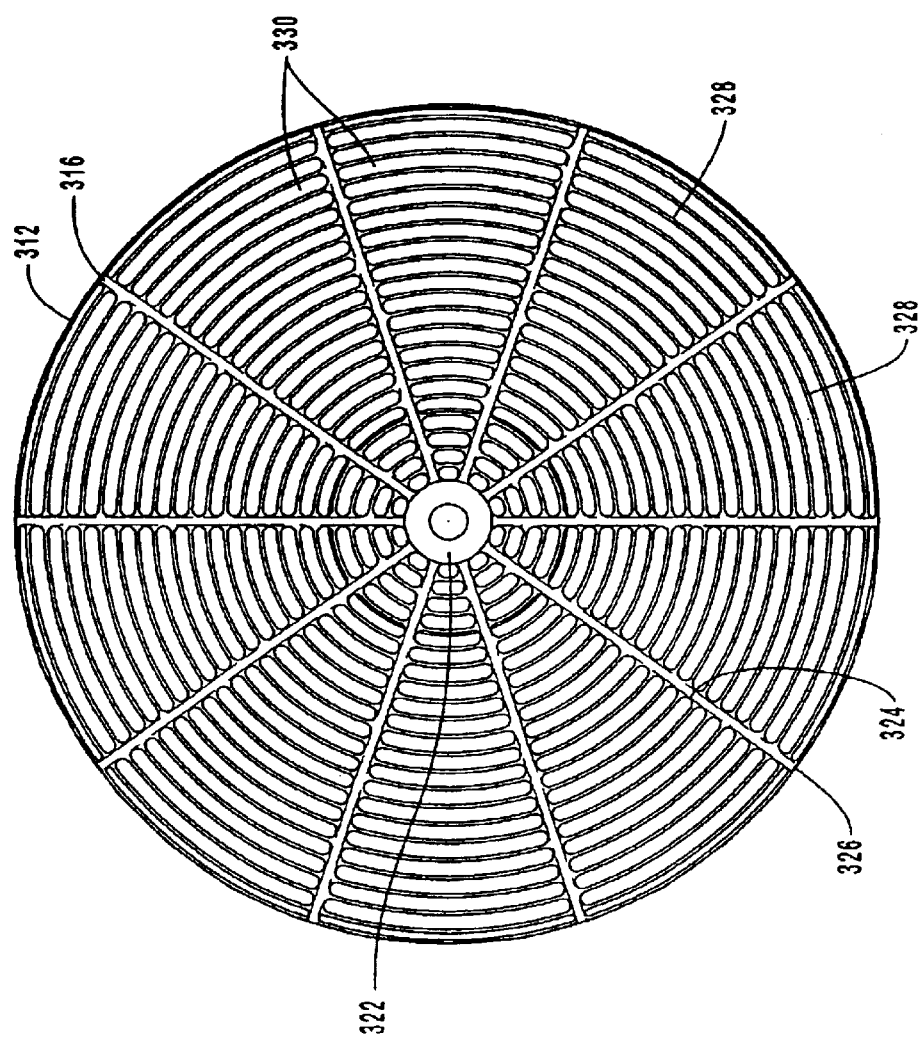
FIG. 15 is a top plan view of the mixer shown in FIG. 14A.

Depicted in FIG. 14A is one alternative embodiment of a mixer 310. Mixer 310 comprises a base 312 having flaps 314 connected thereto. Base 312 has a substantially circular plate-like configuration having a top surface 316 and an opposing bottom surface 318. As depicted in FIG. 15, base 312 includes an integrally formed central hub 322 and integrally formed struts 324 that radially outwardly project from hub 322 to an outer edge 326. Struts 324 divide base 312 into a plurality of wedge shaped sections 328. Formed within each section 328 so as to extend between top surface 316 and bottom surface 318 are a plurality of fluid openings 330.

Base 312 is typically made of a polymeric material, such as high density polyurethane or polyethylene, but can also be made of metal, composite, or other desired materials. Base 312 can be molded having fluid openings 330 formed thereon. Alternatively, base 312 and/or fluid openings 330 can be cut. In one embodiment, base 312 has a thickness between surfaces 316 and 318 in a range between about 1 cm to about 6 cm with about 2 cm to about 4 cm being more common. Other dimensions can also be used depending on size and use parameters.

Figure 16:
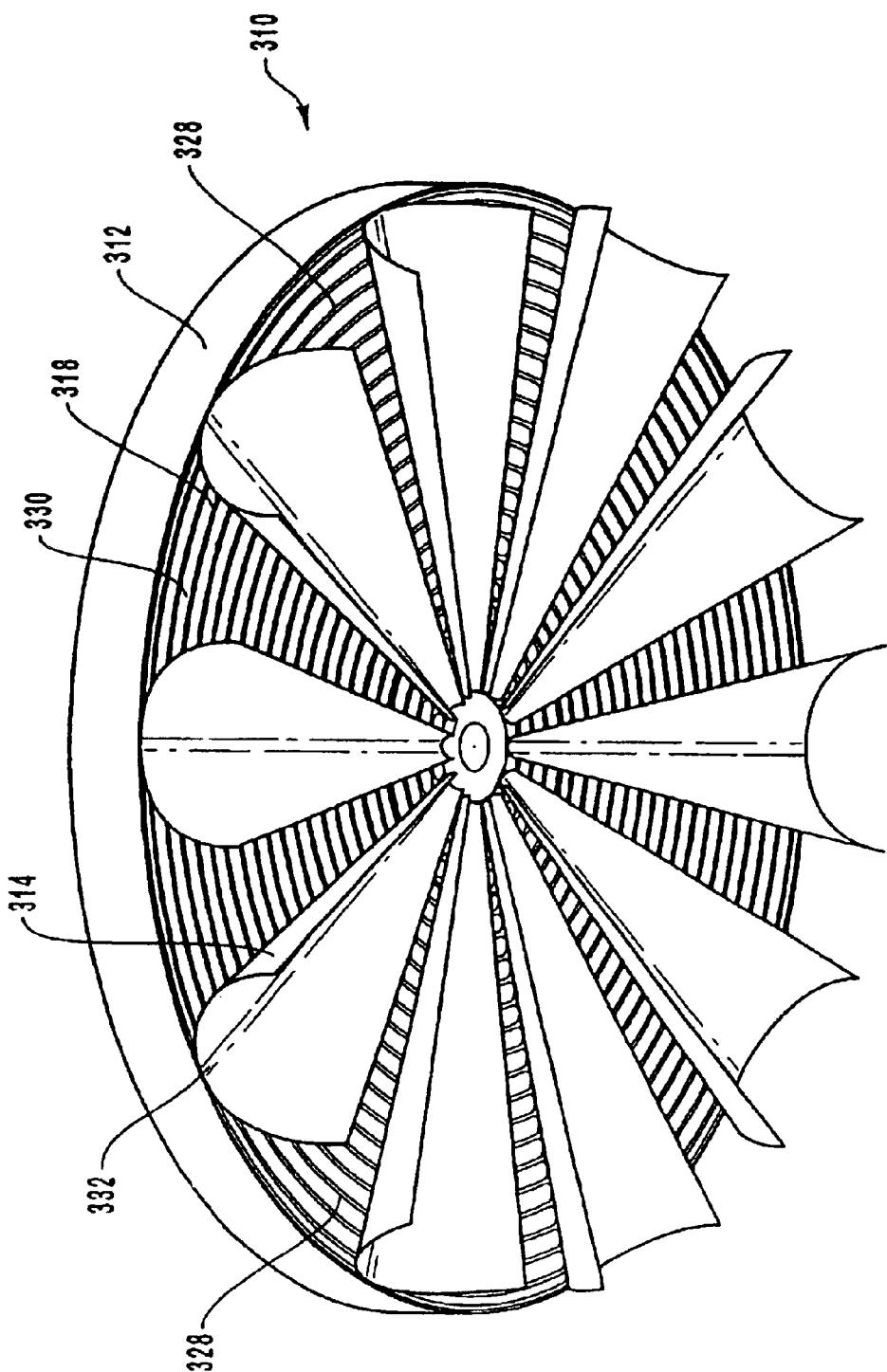
FIG. 16 is a bottom perspective view of the mixer shown in FIG. 14A with the flaps thereof being downwardly flexed.

As depicted in FIG. 16, flaps 314 are mounted on bottom surface 318 of base 312. Flaps 314 have substantially the same configuration as flaps 264. In this embodiment flaps 314 are comprised of polyethylene sheets having a thickness in a range between about 0.1 mm to about 5 mm with about 0.2 mm to about 2 mm being more common. Again, other materials and thicknesses can be used. In contrast to mixer 204 where flaps 264 are held in place by spokes 262, flaps 314 are directly welded to base 312. That is, each flap 314 is welded, such as by heat, sonic, chemical welding or the like, along a central axis 332 to a corresponding strut 324. Each flap 314 is configured to overlay half of each adjacent section 328 with the side edges of each flap 314 being free to flex. Flaps 314 can thus operate in the same fashion as previously discussed with regard to flaps 264.

Figure 17:
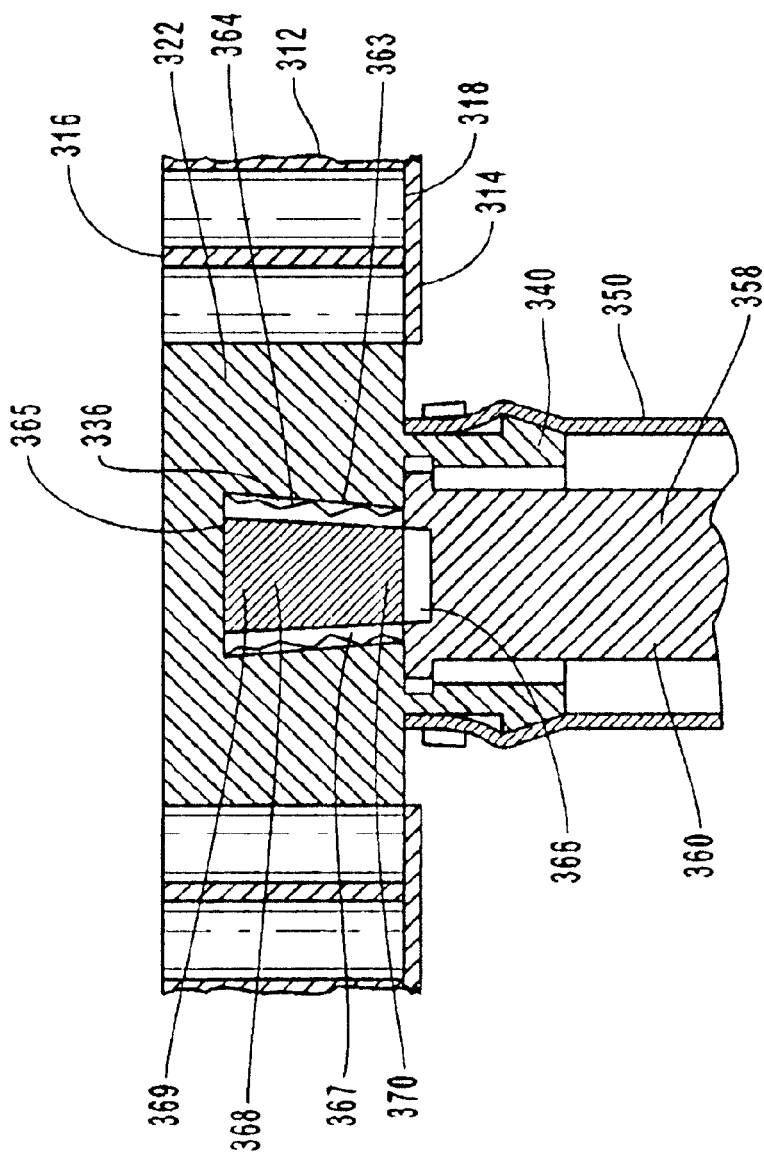
FIG. 17 is an enlarged cross sectional side view of the hub of the mixer shown in FIG. 14A.

As depicted in FIG. 17, a blind hole 336 is formed on bottom surface 318 of hub 322 of base 312. Blind hole 336 has a frustoconical configuration that tapers outwardly toward top surface 316. The taper is typically in a range between 1° to about 10° although other angles can also be used. A tubular connector 340 has a first end disposed on bottom surface 318 so as to encircle blind hole 336 and has a barbed annular second end downwardly projecting therefrom. Tubular connector 340 can be integrally formed with or connected to base 312.

Returning to FIG. 14A, a tubular port 344 has a flanged first end 346 that is welded or otherwise secured to mixing bag 202 and has a barbed second end 348 that outwardly projects from mixing bag 202. A tubular seal 350 has a first end 352 and an opposing second end 354. First end 352 is received over the second end of tubular connector 340 so as to form a sealed connection therewith. Second end 354 of seal 350 is passed through tubular port 344 and then turned inside-out so as to enclose barbed second end 348 of tubular port 344 and form a sealed connection therewith. Tubular seal 350 is typically made of a polymeric material, such as polyethylene, having a thickness in a range between about 0.5 mm to about 10 mm with about 0.75 mm to about 3 mm being more common. Other flexible materials and thicknesses can also be used.

A mixing shaft 358 is shown removably connected to mixer 310. Mixing shaft 358 has a first end 360 and an opposing second end 362. Returning to FIG. 17, a tubular collet 363 projects from first end 360 of shaft 358. Collet 363 has an exterior surface 364 with threads formed thereon and an interior surface 365 that bound a socket 366. A plurality of radially spaced apart slot 376 extend between surfaces 364 and 365 along the length thereof. Disposed within socket 336 is a frustoconical wedge 368 having a first end 369 and an opposing second end 370.

Prior to coupling mixing shaft 358 to mixer 310, collet 363 has a substantially cylindrical configuration with socket 366 being sized only to receive the smaller second end 370 of wedge 368. During assembly, first end 360 of mixing shaft 358 having wedge 368 partially received within socket 366 is passed through tubular seal 350 and into blind hole 336 of base 312. As collet 363 is further pressed into blind hole 336, first end 369 of wedge 368 biases against the bottom of blind hole 336. In turn, wedge 368 is pressed further into socket 366 causing collet 363 to radially outwardly expand so that the threaded exterior surface 364 of collet 363 engages against the interior surface of blind hole 336. By further pressing wedge 368 within collet 363, first end 360 of mixing shaft 358 becomes securely connected to base 312. However, once use of mixing bag 202 is completed, mixing shaft 358 can be rotated so that collet 363 unscrews from base 312, thereby enabling reuse of mixing shaft 358.

The above embodiment enables relatively easy attachment of mixing shaft 358 to mixer 310 positioned within mixing bag 202 without fear of cross threading. In alternative embodiments, however, it is appreciated that mixing shaft 358 can be connected to mixer 310 using conventional connections, such as threaded engagement, or can be permanently secured to mixer 310.

Figure 14B:
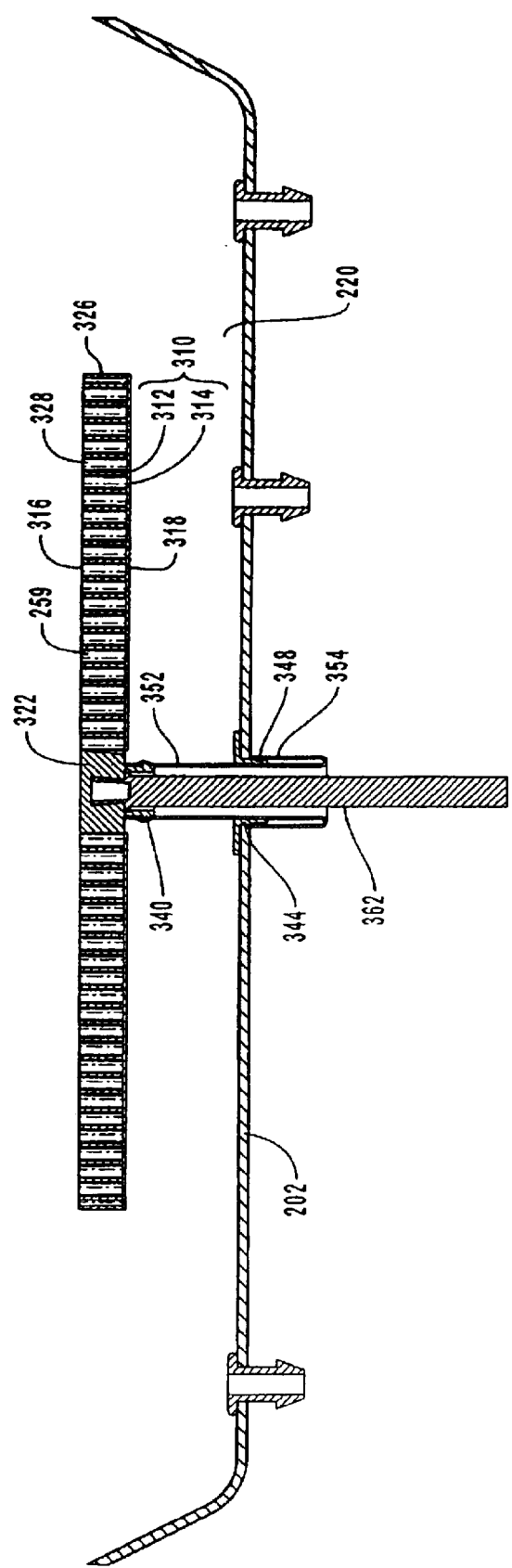
FIG. 14B is a cross sectional side view of the mixer shown in FIG. 14A in a second position.

Returning to FIG. 14A, once mixing shaft 358 is secured to mixer 310, mixing shaft 358 can be used for selectively raising and lower mixer 310 for mixing the solution within compartment 202. In contrast to expansion and contraction of bellow section 288 of tubular seal 206 (FIG. 9), tubular seal 350, as shown in FIGS. 14A and 14B progressively turns inside-out and then turns back rightside-in as shaft 358 is raised and lowered. Tubular seal 350 is thus another example of a means for enabling a mixing shaft to raise and lower a mixer within compartment 220 of bag 202 while preventing leaking of liquid from compartment 220 of mixing bag 202.

Figure 18A:
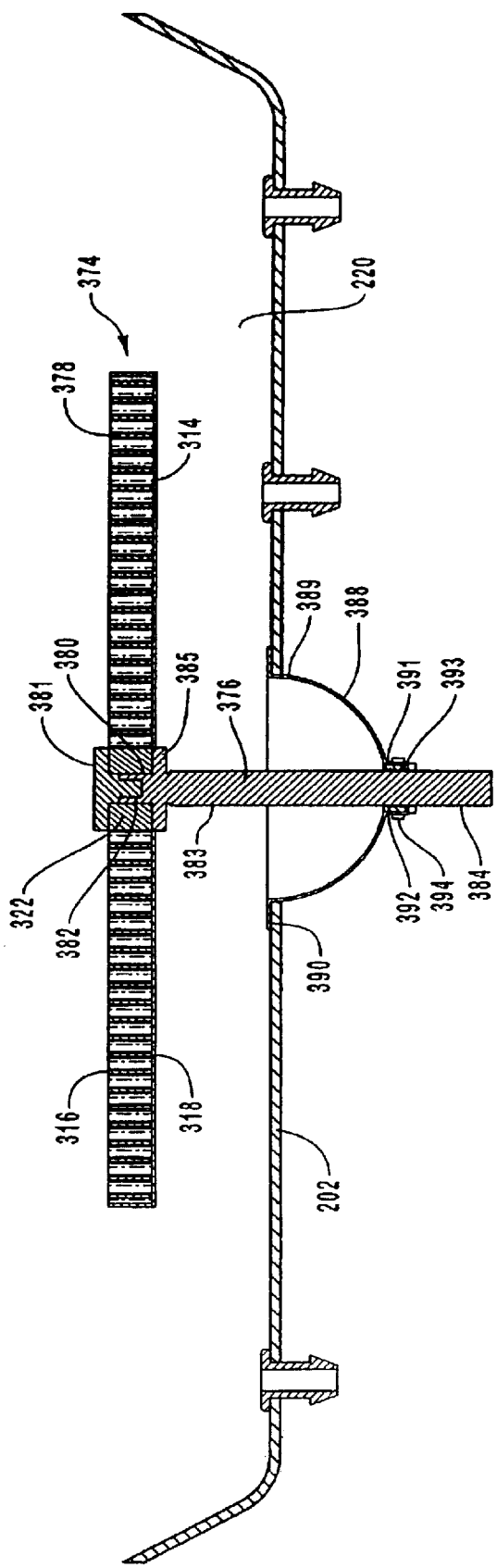
FIG. 18A is a cross sectional side view of the bottom end of the mixing bag shown in FIG. 8 with an alternative embodiment of a mixer disposed therein.

Depicted in FIG. 18A is another alternative embodiment of a mixer 374 having a mixing shaft 376 attached thereto. Like elements between mixer 374 and mixer 310 are identified by like reference characters. Mixer 374 is substantially identical to mixer 310 except that base 378 of mixer 374 does not include blind hole 336 or tubular connector 340. Rather, base 378 has a through hole 380 formed through hub 322. A bolt 381 is disposed on top surface 316 of base 378 such that a threaded shaft 382 thereof is received within through hole 380. Mixing shaft 376 has a first end 383 and an opposing second end 384. A threaded socket is recessed within first end 383 of mixing shaft 376. First end 383 of mixing shaft 376 is positioned within through hole 380 and threadedly engaged with bolt 381. An annular flange 385 outwardly projects from mixing shaft 376 and biases against bottom surface of base 378, thereby preventing mixing shaft 376 from passing through base 378. In this embodiment, mixing shaft 376 is designed to be permanently attached to mixer 374. Again, mixing shaft 376 can be connected to mixer 374 using any conventional attachment mechanisms such as welding, integrally forming, screwing, clipping, and the like.

Mounted on or toward second end 384 of mixing shaft 376 is a flexible diaphragm 388. In one embodiment diaphragm 388 is molded from polyurethane. Other flexible materials can also be used. Diaphragm 388 has a hollow semi-spherical configuration that includes an outer annular base 389 with an annular flange 390 radially outwardly projecting therefrom. Flange 390 is sealed, such as by welding or other conventional techniques, to mixing bag 202 so that diaphragm 388 communicates with compartment 220 of mixing bag 202. Diaphragm 388 also includes a central portion 391 having a tubular sleeve 392 projecting therefrom. A plurality of ribs 393 encircle and radially outwardly project on mixing shaft 376 at or toward second end 384 thereof. Sleeve 392 of diaphragm 388 is passed over ribs 393 so that a sealed connection is formed between mixing shaft 376 and diaphragm 388. A tie 394 can be secured around sleeve 392 to ensure the sealed connection.

Figure 18B:
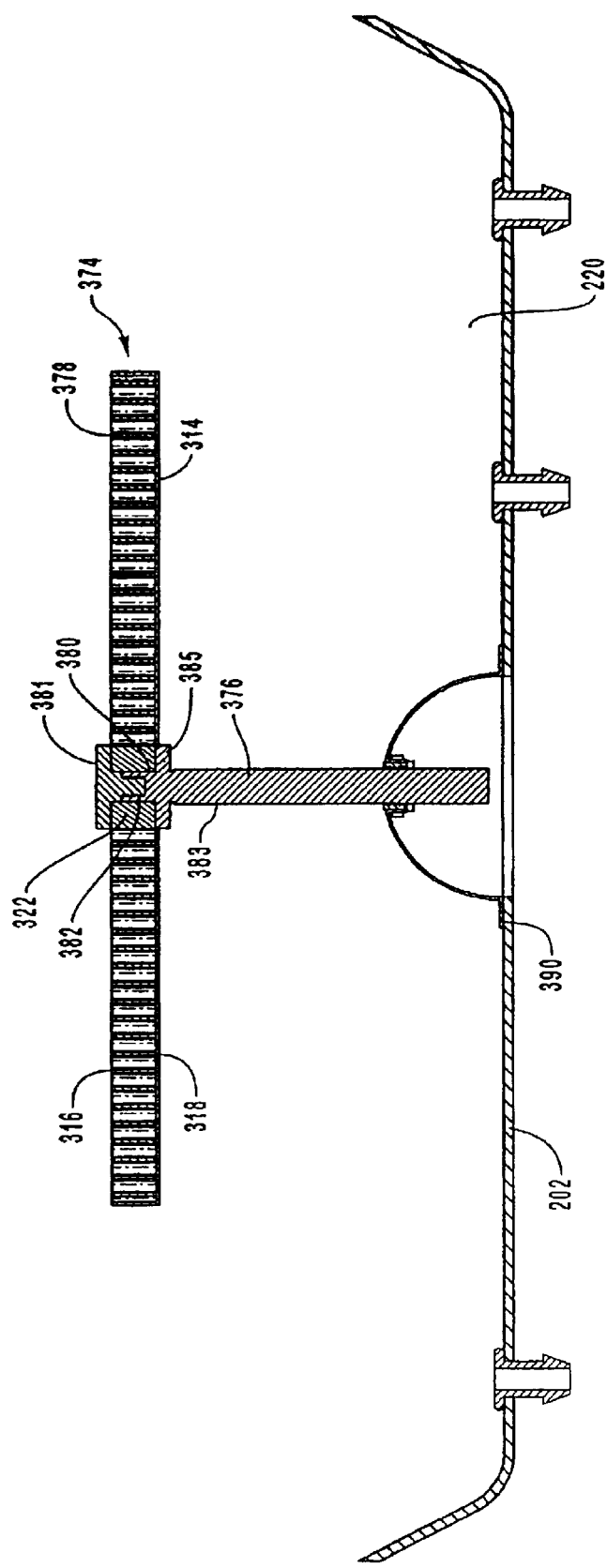
FIG. 18B is a cross sectional side view of the mixer shown in FIG. 18A in a second position.

In this configuration, diaphragm 388 is another example of the means for enabling a mixing shaft to raise and lower a mixer within compartment 220 of mixing bag 202 while preventing leaking of liquid from compartment 220 of mixing bag 202. Specifically, as depicted in FIGS. 18A and 18B, as mixing shaft 376 is selectively raised and lowered so as to raise and lower mixer 374, diaphragm 388 freely flexes in and out so as to allow free movement of mixing shaft 376.

It is appreciated that the various mixers, shafts, and/or seals and components thereof can be mixed and matched to create a variety of other alternative embodiments. It is also noted that the first end of seals 206 and 350 can be coupled in a sealed connection directly to mixing shafts 208 and 358, respectively, as opposed to the corresponding mixers.

III. Positioning Mixing Assembly in Tank Assembly.

In one embodiment, mixing assembly 200 is manufactured and sold as a disposable unit. During manufacture, a portion of panels 228 are seamed together as previously discussed. Prior to complete sealing of panels 228, however, mixer 204 is positioned within compartment 220. Seal 206 is then coupled between mixer 204 and mounting port 242 as previously discussed. Once seal 206 is appropriately attached, the remainder of panels 228 are seamed together to complete the production.

Figure 19:
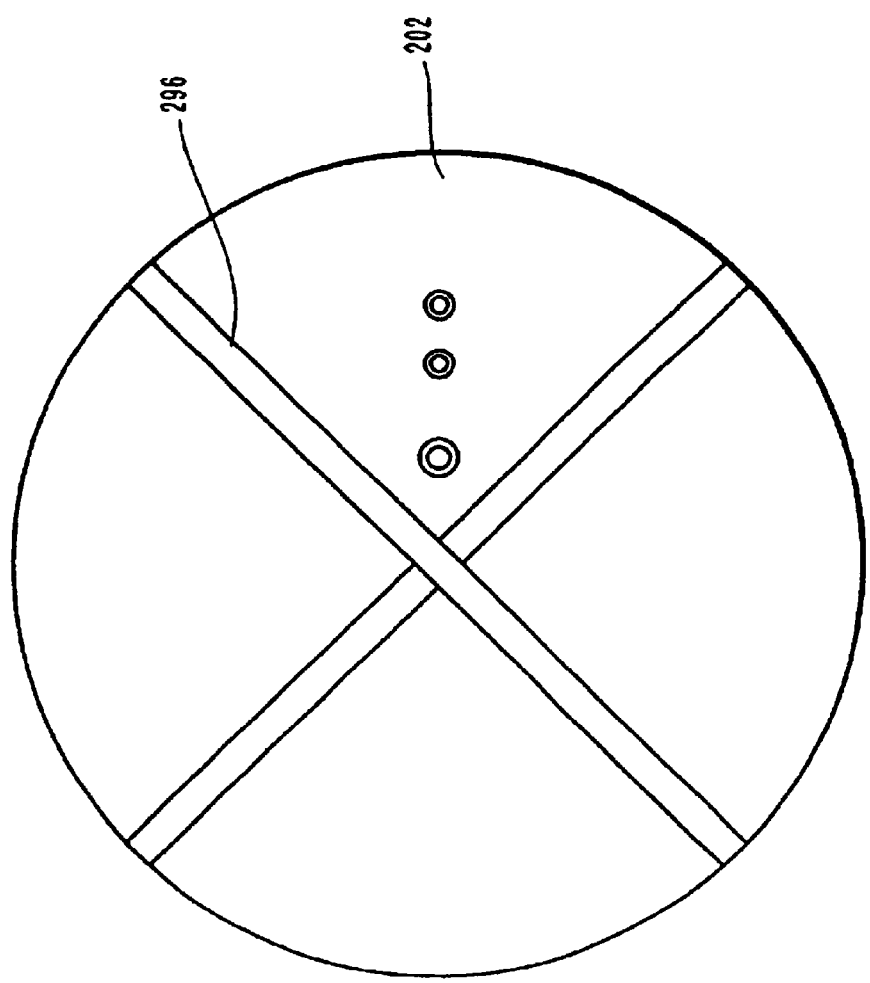
FIG. 19 is a top plan view of the mixing bag shown in FIG. 8 in a collapsed state bounded by a harness.

As shown in FIG. 19, mixing bag 202 is then collapsed in an accordion fashion and bounded by a harness 296. Once complete, mixing assembly 200 can be sterilized such as by ionizing radiation or other conventional methods. Depending on the desired solution and the method of manufacture, however, it may not be necessary to sterilize mixing assembly 200.

Mixing shaft 208 can be mounted to mixer 204 either before mixer 204 is disposed within compartment 220 of mixing bag 202 or at any time after mixer 204 is sealed within compartment 220. As depicted in FIG. 11, this latter attachment is accomplished by simply passing first end 278 of mixing shaft 208 from exterior of mixing bag 202 up through mixing port 242 and tubular seal 206 and then screwing mixing shaft 208 into mixer 204. In this embodiment, mixing shaft 208 can either be disposed of after use or removed and reused.

In the embodiments where mixing shaft 208 is considered to be disposable, mixing shaft 208 can be connected to mixer 204 in any conventional manner such as by adhesion, welding, press fit, or can be integrally formed as a portion of hub 246. Where the first end of seal 206 is coupled with mixing shaft 208 rather then mixer 204, mixing shaft 208 is coupled with mixer 204 prior to being sealed within compartment 220. The second end of mixing shaft 208 is then passed down through seal 206 to the exterior of mixing bag 202.

Mixers 310 and 374 are also position within compartment 220 of mixing bag 202 prior to complete seaming of panels 228. Likewise, mixing shafts 358 and 376 can also be coupled with corresponding mixers either before or after the mixers are sealed within compartment 220.

As previously discussed, mixing bag 202 can be manufactured to hold any desired volume of fluid. During use, a manufacturer initially determines how much solution is desired to be manufactured. Based on that determination, a mixing assembly 200 corresponding to the desired volume is selected. Based on the size of the selected mixing assembly 200, floor 110 of tank assembly 20 is either raised or lowered so that when mixing bag 202 is completely inflated or filled within chamber 60 of tank assembly 20, top end wall 215 of mixing bag 202 is positioned within upper end 30 of tank assembly 20.

Once floor 110 is moved to the desired position, mixing assembly 200 is inserted within chamber 60 of tank assembly 20 through open doorway 57. More specifically, in one embodiment fluid preparation system 10, as depicted in FIG. 1, further comprises a lift 400 mounted on platform 12. Lift 400 comprises a tower 402 having an arm 404 mounted thereon. Tower 402 has a longitudinal axis 406 and is configured to rotate about such axis. Similarly, arm 404 is configured to selectively raise and lower along the length of tower 402. Mounted on arm 404 is a winch 408 operable with a cable 410. Mounted at the end of cable 410 is a connecter 412.

To position mixing assembly 200 within chamber 60, arm 404 and/or cable 408 is lowered so that connecter 412 is attached to harness 296 on mixing assembly 200. Lift 400 is then used to guide mixing assembly 200 into chamber 60 through doorway 57. Mixing assembly 200 is lowered within chamber 60 so that as bottom end wall 217 of mixing bag 202 comes to rest on base floor 112 of floor 110, ports 236, 238, and 240 are aligned with port holes 116. Likewise, mixing shaft 208 is aligned with and passed through central port hole 117 so as to couple with actuation rod 172 by coupler 176 as previously discussed. Once mixing assembly 200 is seated within chamber 60, harness 296 is removed and door 25 is closed and locked.

Next, the ports extending through ports holes 116 are coupled with various tubes. For example, a delivery tube 420 is coupled with outlet port 238. Delivery tube 420 passes through or couples with a first value 422, a pump 424, a second valve 426, and then couples with filtration system 500 which will be discussed below in great detail. Coupled with first valve 422 is a sample tube 428. A return tube 430 extends between second valve 426 and inlet port 240.

The term "tube" as used in the specification and appended claims is intended to include conventional flexible hose and tubing which is relatively inexpensive and can be easily replaced, if desired, between the manufacture of different batches or types of solution. The term "tube", however, is also intended to include rigid piping and other forms of conduits which may be fixed and require sterilization between the manufacture of different batches or types of solution.

Furthermore, the term "valve" as used in the specification and appended claims is broadly intended to include any type or combination of mechanisms which enables selective closing of a fluid or gas path. For example, first valve 422 can comprise a tee joint coupled with two sections of delivery tube 420 and sample tube 428 acting in combination with an external clamp, such as a conventional hose clamp, which can be manually or otherwise selectively closed around either delivery tube 420 or sample tube 428. Alternatively, there are a variety of other conventional types of electrical or manual valves that can be used. The use of external clamps or other forms of valves which do not contact the solution have the benefit in that they can be reused without sterilization. However, valves that contact the solution can also be used and then discarded or sterilized. In this regard pump 424 can comprises a peristaltic pump wherein deliver tube 420 passes therethrough without the solution ever contacting the pump. Conventional pumps can also be used, however, where the solution directly contacts the pump.

Coupled with inflation port 236 is an air tube 432. Air tube 432 is coupled with an air source. In one embodiment, the air source comprises a compressor or some form of tank wherein compressed air is already stored. In the embodiment depicted, a portion of platform 12 is hollow and forms a large storage tank for compressed air. One benefit of using a large storage tank for holding compressed air is that it enables quick inflation of mixing bag 202. By using platform 12 as the storage tank, the use of space is optimized. Air tube 432 is coupled with platform 12 by way of a valve 434.

Figure 20:
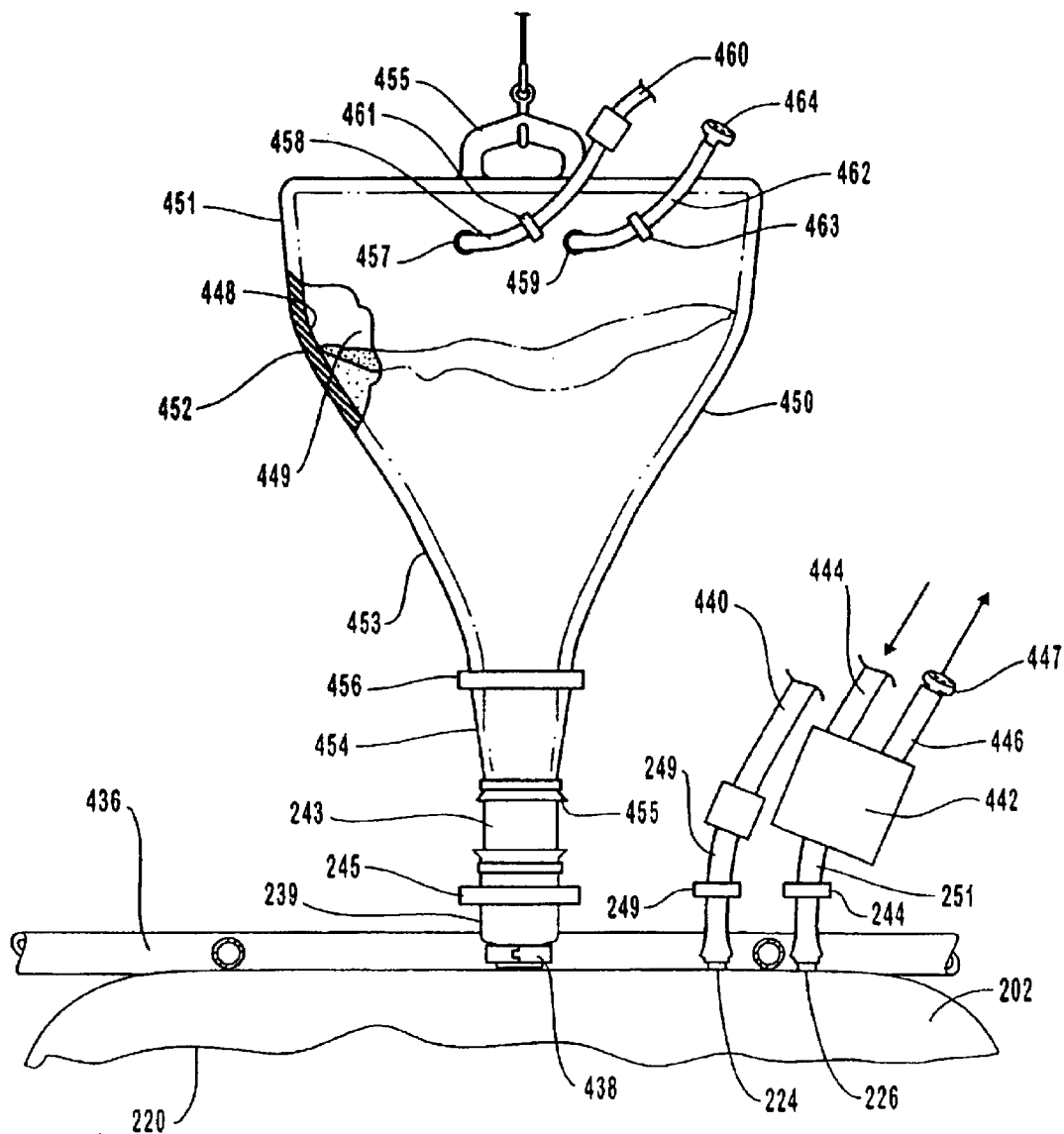
FIG. 20 is an elevated side view of a feed bag coupled with the top end of the mixing bag shown in FIG. 8.

Once air tube 432 is coupled, air or some other form of gas is fed through tube 432 into compartment 220 so as to completely or substantially inflate mixing bag 202 within chamber 60. As previously discussed, clamps 244 are used in association with ports 222, 224, and 226 so as to seal the ports, thereby enabling inflation of mixing bag 202. Alternatively, various forms of caps, seals or other forms of stops can be used to temporarily seal the ports. As depicted in FIG. 20, a support rack 436 is mounted to or positioned on upper end 30 of side wall 24 of tank assembly 20 so as to extend at least partially across side wall 24. A removable clamp 438 is used to secure feeding port 222 (FIG. 10A) to support rack 436.

Once mixing bag 202 is inflated and secured to support rack 436, a fluid line 440 is coupled with fluid port 224 either directly or through extension tube 249. Fluid line 440 is configured for selectively delivering fluid, such as various forms of water, into mixing bag 202. A pressure regulator 442 is coupled with pressure port 226, such as through extension tube 251, so as to selectively control the air pressure within mixing bag 202 within a desired range. In this regard, pressure regulator 442 operates with an air inlet line 444, which is coupled with a pump or pressurized gas source, for delivering air or other gases into mixing bag 202 and an air outlet line 446 for allowing air to escape from mixing bag 202. A filter 447 is coupled with outlet line 446 to prevent particulate feed component within mixing bag 202 from escaping with the exiting air.

The above described process is typical for placement of a relatively large mixing bag within a tank assembly having a movable floor. For tank assembly 178 shown in FIGS. 6 and 7 where the floor is fixed to the side wall, mixing bag 202 is typically sized so as to have a volume corresponding to the volume of the chamber of tank assembly. In general, such systems can efficiently mix fluid volumes down to ⅕ the volume of the mixing bag. For example, a tank assembly 178 having a chamber with a volume of 100 liters would typically receive a mixing bag having a compartment with a volume of 100 liters. In turn, such an arrangement could be used to efficiently mix a volume of solution ranging from about 20 liters to about 100 liters.

Mixing bag 202 is inserted into the chamber of tank assembly 178 by being lowered through the top opening thereof. This can be accomplished either manually or through the use of lift 400. If desired, feeding port 222 (FIG. 10A) can be secured to support rack 436 (FIG. 20) mounted on top of tank assembly 178. For small mixing bags, however, the mixing bag need not be supported within the tank assembly.

The inflation of mixing bag 202 is in part helpful for the proper positioning of mixing bag 202 within the tank assembly, for accessing and connecting various structures to the top of mixing bag 202, and, as will be discussed below in greater detail, for creating a positive gas pressure that helps the dry material component to feed into mixing bag 202. It is not necessary, however, especially for small mixing bags, to inflate the mixing bag. Furthermore, for small mixing bags, air tube 432 (FIG. 1) can be eliminated and the mixing bag inflated solely through air inlet line 444 (FIG. 20).

IV. Feed Bag.

Depicted in FIG. 20, coupled with mixing bag 202 is a feed bag 450. Feed bag 450 comprises a body 452 that extends from an upper end 451 to a lower end 453. Body 452 has an interior surface 448 bounding a compartment 449. Compartment 449 is at least partially filled with a feed component which is typically in the form of a powder, grain, or other substantially dry material that is flowable. The feed component can also be in a liquid form. Although the feed component can be any desired material, in one embodiment the feed component comprises culture media, buffers, or reagents in a powder form.

Lower end 453 of body 452 tapers down to a tubular spout 454. Tubular spout 454 bounds an outlet 455 that is selectively and removably coupled with tubular coupling 243. (Tubular coupling 243 was previously discussed with regard to FIG. 10A.) This connection enables the feed component to pass from feed bag 450 to mixing bag 202 and can be secured through the use of a tie, band, clamp or the like. A removable clamp 456 is clamped across spout 454 to prevent unwanted passage of the feed component through spout 454.

Feed bag 450 further comprises a handle 455 that is positioned at upper end 451 of body 452 for supporting feed bag 450. Formed on upper end 451 of body 452 so as to communicate with compartment 449 is a fluid port 457 and a spaced apart vent port 459. In one embodiment, ports 457 and 459 comprise conventional barbed ports outwardly projection from body 452. Other conventional types of ports can also be used. Coupled with ports 457 and 459 is a fluid tube 458 and a vent tube 462, respectively. Furthermore, a clamp 461, such as a conventional hose clamp, is positioned on each of tubes 458 and 462.

Fluid tube 458 is selectively and removably coupled with a delivery line 460 which communicates with a fluid source for delivering a rinsing fluid, such as water, into compartment 449. Vent tube 462 is coupled with a filter 464. Filter 464 can be mounted directly on vent port 459 or at any point along vent tube 462. Filter 464 allows air and/or other gases to enter and/or escape from compartment 449 while preventing the escape of the feed component therethrough. In alternative embodiments, it is appreciated that feed bag 450 can be formed with a single port which can be used for either or both of the above functions.

Body 452 of feed bag 450 can be made of the same materials, such as polyethylene, and layers as previously discussed with regard to body 203 of mixing bag 202. Furthermore, body 452 and thus feed bag 450 can be any desired shape or configuration and can be either a two or three dimensional bag. It is also appreciated that feed bag 450 can be any form of collapsible container or a rigid reusable container.

Returning to FIG. 1, lift 400 further includes an L-shape support 466 having a connector 468 mounted on the end thereof. Support 466 is selectively rotatable about the longitudinal axis of arm 404 to facilitate connecting connector 468 to handle 455 of feed bag 450. Feed bag 450 is secured to connector 468 so as to suspend therefrom. Support 466 can also be configured to weigh feed bag 450 when connected thereto.

Figure 21B:
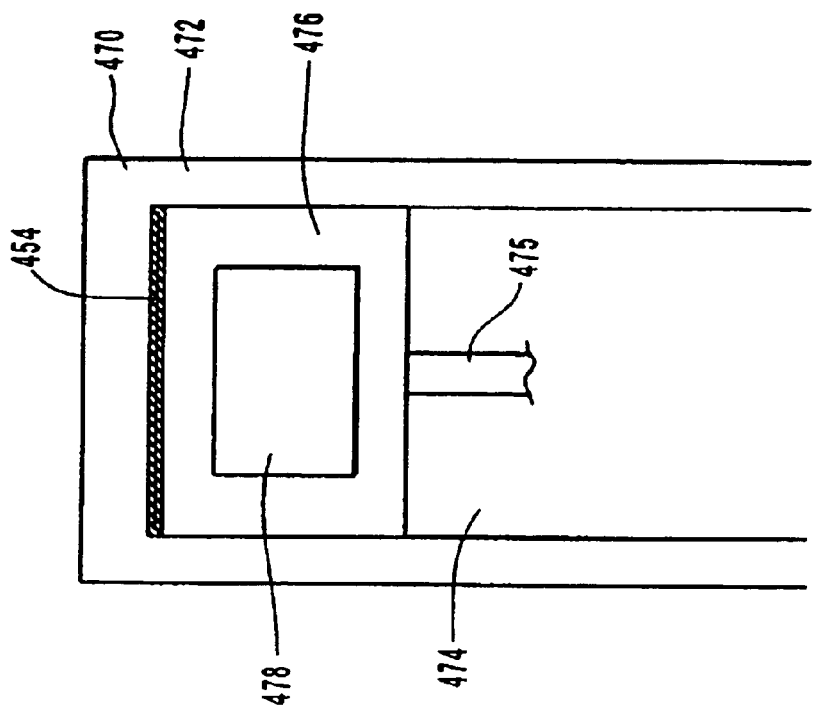
FIG. 21B is a top plan view of the regulator shown in FIG. 21A in a closed position.
Figure 21A:
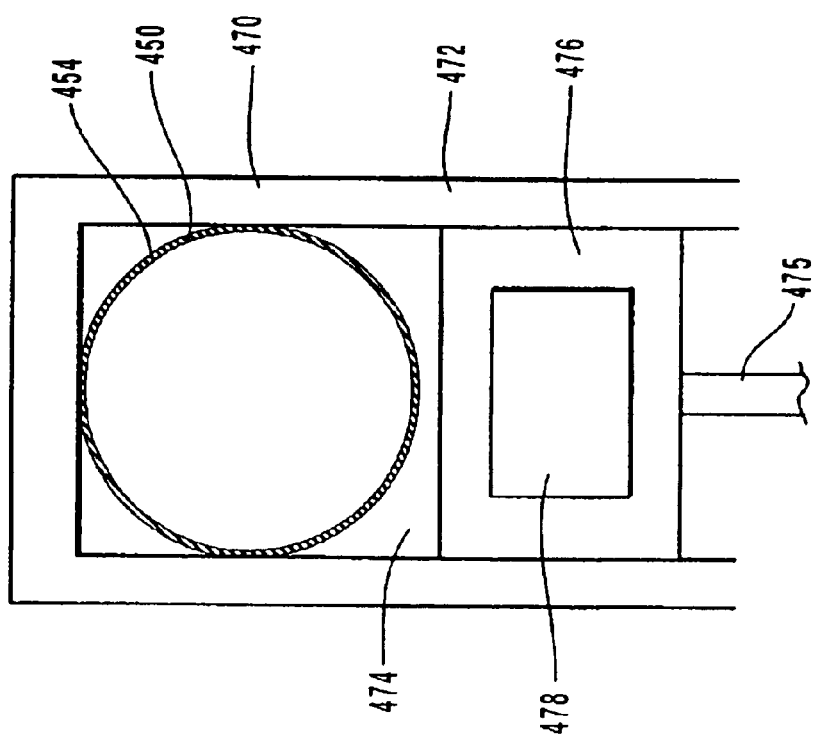
FIG. 21A is a top plan view of a regulator in an open position operable with the feed bag shown in FIG. 20.

Although not required, in one embodiment a regulator 470 is mounted to arm 404 for selectively dispensing the feed component from feed bag 450. As depicted in FIG. 21A, regulator 470 comprises a base frame 472 having a central channel 474 formed thereon. Tubular spout 454 of feed bag 450 is positioned so as to pass through channel 474. A control plate 476 is slidably mounted to base frame 472 and is controlled by a push rod 475 to selectively slide within channel 474. Mounted on control plate 476 is a vibrator 478. During operation, control plate 476, operable under electrical control of push rod 475, is advanced within channel 474 so as to compress tubular spout 454 against base frame 472, thereby preventing the unwanted passage of the feed component therethrough.

For controlled dispensing of the feed component, control plate 476 is retracted an incremental amount, thereby allowing the feed component to flow through the now only partially constricted tubular spout 454. To help facilitate the passage of the feed component through tubular spout 454, vibrator 478 can be activated which vibrates the feed component and assists it in passing through tubular spout 454, coupling 243, extension sleeve 239 and into compartment 220. Dispensing of the feed component can be determined through the change of weight of feed bag 450 as measured by support 466. It is appreciated that regulator 470 may or may not be required when all of the contents of feed bag 450 is to be dispensed within mixing bag 202.

In one method of use as depicted in FIG. 20, once mixing bag 202 is inflated, air tube 432 (FIG. 1) is sealed closed and clamps 244 are removed from association with fluid port 224 and pressure port 226. Compartment 220 of mixing bag 202 is now at least partially filled with a liquid component entering through fluid line 440 and fluid port 224. In one embodiment, mixing bag 202 is initially filled with the liquid component to an amount between about 50% to 80% by volume. As the liquid component enters compartment 220, the air within compartment 220 bleeds out through pressure port 226 so that the pressure range is maintained within compartment 220. Either before, during, or after initial fluid filing of compartment 220, feed bag 450 is coupled with mixing bag 202 as discussed above.

Once mixing bag 202 is filled with the liquid component to the initial capacity, clamps 245 and 456 are removed such that the feed component is free to feed into compartment 202 from feed bag 450. The feed component can be fed as a dump or regulated through the use of regulator 470 as previously discussed. In alternative embodiments, the feed component can be feed into compartment 202 at any time during the process.

It has been discovered that the free and continuous flow of the powdered feed component from body 452 of feed bag 450 through tubular spout 454 and extension sleeve 239 is improved if feed bag 450 is operated under a positive air pressure. For example, the powdered feed component has improved flow properties if feed bag 450 is at least partially inflated by air flowing from mixing bag 202 up through extension sleeve 239 and tubular spout 454. As such, pressure regulator 442 maintains the air pressure within compartment 220 of mixing bag 202 so that when clamps 245 and 456 are removed, feed bag 450 is subject to a positive air pressure. That is, air or other gases can be added or removed from mixing bag 202 through air inlet line 444 and air outlet line 446, respectively, which are controlled by pressure regulator 442.

Maintaining mixing bag 202 under a positive gas pressure also helps to ensure that unwanted gases or particulates do not unintentionally enter mixing bag 202 and contaminate the solution. In one embodiment, pressure regulator 442 maintains a positive pressure within compartment 220 in a range between about 0.5 KPa to about 14 KPa with about 3.5 KPa to about 10 KPa being more common. Other pressures can also be used depending on the system parameters.

Once feed bag 452 is empty, clamp 461 on fluid tube 458 is opened and a rinsing fluid, such as water or other compatible liquids for the solution, is fed through line 460 and fluid tube 458 into feed bag 450. The rinsing fluid is used to help flush suspended particles and other residue of the feed component within feed bag 450, coupling 243, and extension sleeve 239 into compartment 220. Once feed bag 452 is empty and flushed, clamp 461 is closed and line 460 disconnected. Furthermore, clamps 244 and 456 are closed about extension sleeve 239 and spout 454, respectively. In this configuration, feed bag 450 remains inflated through air delivered from mixing bag 202.

To deflate feed bag 450, clamp 463 is opened on vent tube 462. The venting air passes through filter 464 so as to capture any residue feed component. Vent tube 462 is also used to deflate feed bags 450 which are only partially emptied of the feed component. Feed bag 450 is uncoupled from coupling 243 either before or after deflating. If required, a new feed bag 450 can then be connected to coupling 243. It is appreciated that in some embodiments it may be necessary to empty several feed bags 450 into mixing bag 202 for the production of the solution while in other embodiments it may be necessary only to empty a portion of a single feed bag 450.

In some methods of use, vent tube 462 can remain open during dispensing of the feed component so that air continually passes out therethrough. Furthermore, in embodiments where mixing bag 202 is not under a positive pressure, vent tube 462 can be opened to allow filtered air to freely pass into mixing bag 202 to enhance the free flow of the feed component. Air or other gases can also be forced through vent tube 462 into feed bag 450.

Figure 22:
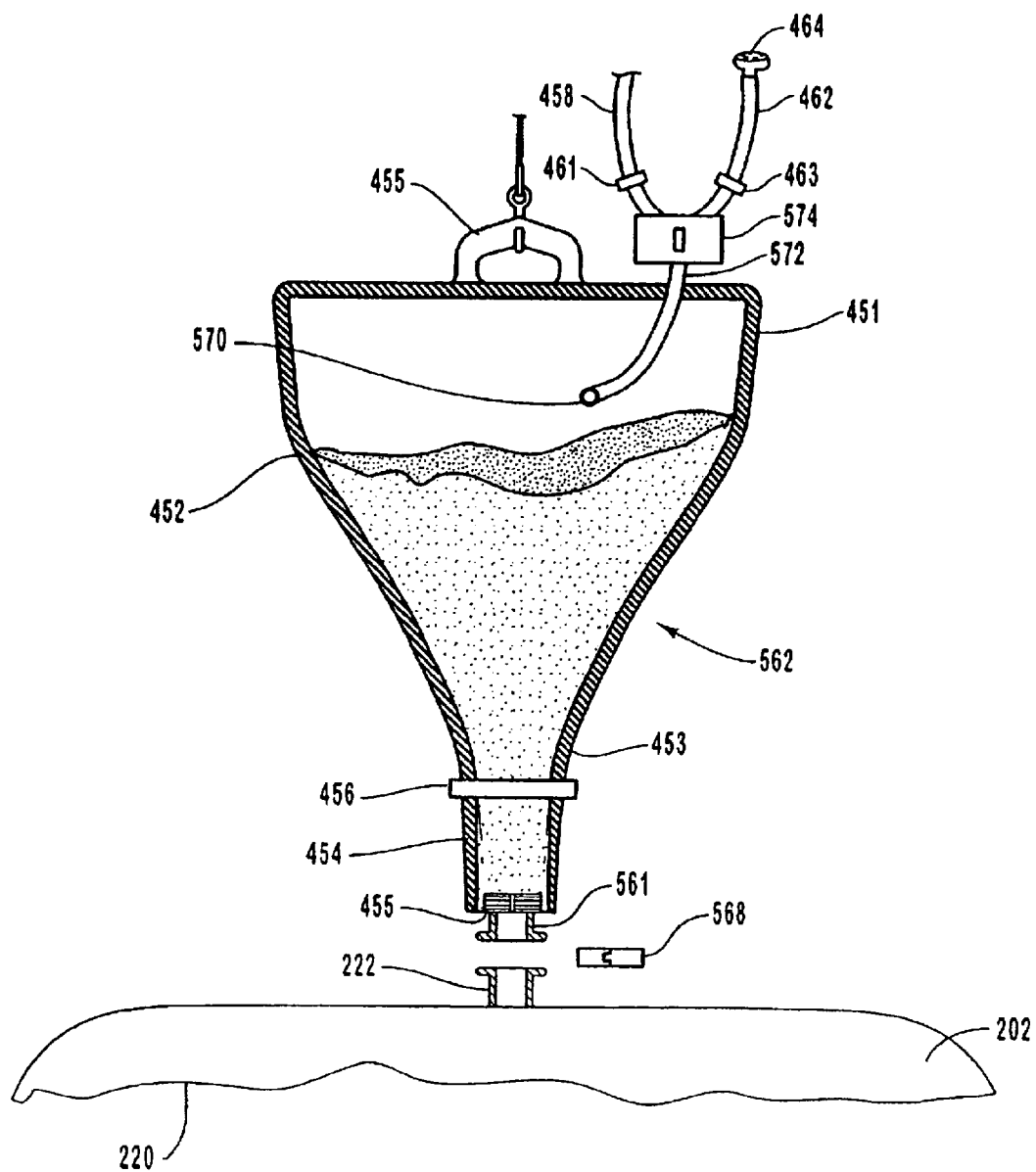
FIG. 22 is an elevated side view of an alternative embodiment of the feed bag shown in FIG. 20.
Figure 23:
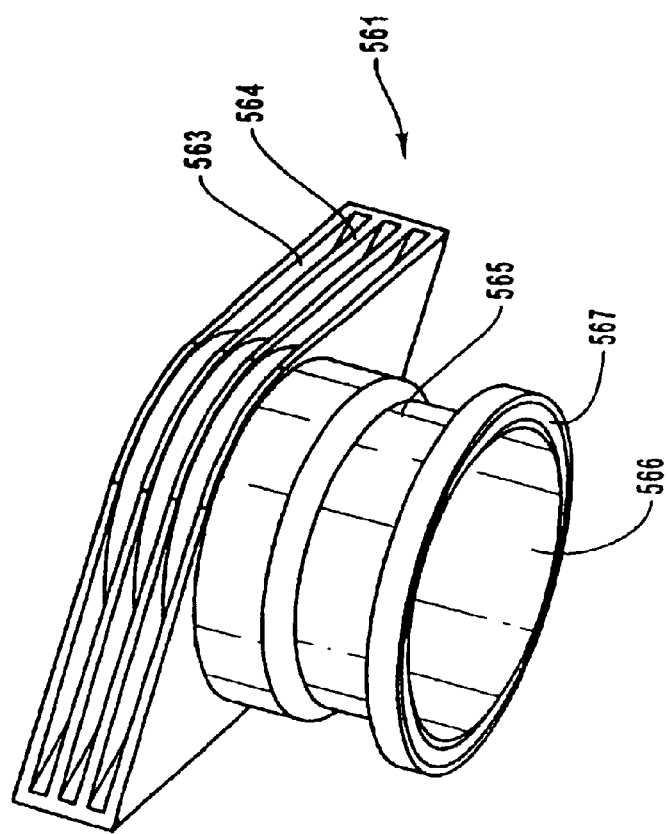
FIG. 23 is a perspective view of a port of the feed bag shown in FIG. 22.

Depicted in FIG. 22 is an alternative embodiment of a feed bag 562. Like elements between feed bag 562 and feed bag 450 are identified by like reference characters. In contrast to feed bag 450 where spout 454 removably connects with coupling 243, spout 454 of feed bag 562 is welded or otherwise fixed to an outlet port 561. As shown in FIG. 23, outlet port 561 has a diamond shaped base 563 having a plurality of ribs 564 extending along the length thereof. A tubular stem 565 is integrally formed with and extends through base 563. Stem 565 bounds an opening 566 extending therethrough and terminates at an outwardly projecting flange 567.

Base 563 of outlet port 561 is received within outlet 455 of body 452 so that the sides of spout 454 cover ribs 564. A conventional welding technique, such as heat or sonic welding, is then used to weld the sides of spout 454 to ribs 564 so as to form a sealed connection therebetween. As desired, a clamp 568 is then used to removably and directly connect outlet port 561 of feed bag 562 to feed port 222 of mixing bag 202.

Feed bag 562 is also distinguished from feed bag 450 in that a single port 570 is formed at upper end 451. A transition tube 572 extends between port 570 and a three-way valve 574. Fluid tube 458 and vent tube 462, as previously discussed, are each coupled with valve 574. Operating valve 574 thus enables fluid tube 458 and vent tube 462 to selectively communicate with compartment 449 of feed bag 562.

V. Spray Nozzle.

Figure 24:
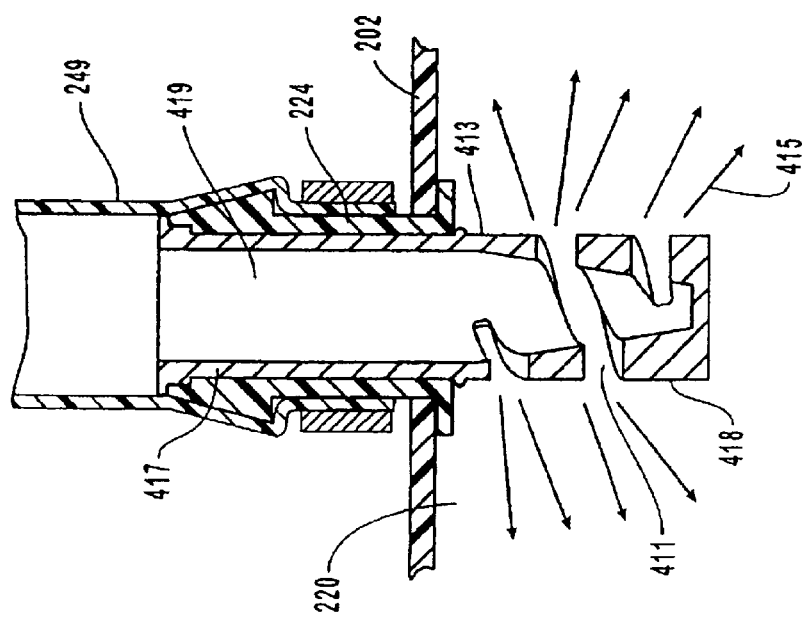
FIG. 24 is an elevated side view of a spray nozzle disposed within a port of the mixing bag shown in FIG. 8.

Either subsequent to and/or concurrently with dispensing of the feed component into mixing bag 202, the remainder of the required fluid component is fed into mixing bag 202 through fluid port 224 (FIG. 20). Although not required, in one embodiment, as depicted in FIG. 24, a spray nozzle 413 is removably mounted to fluid port 224. As depicted by arrows 415, spray nozzle 413 facilitates a radial outward spraying of the liquid component entering compartment 220 of mixing bag 202 through fluid port 224. The sprayed liquid component helps wash down feed component that may have collected on the side walls of mixing bag 202 and also helps remove particles of the feed component suspended or floating within mixing bag 202.

Figure 26:
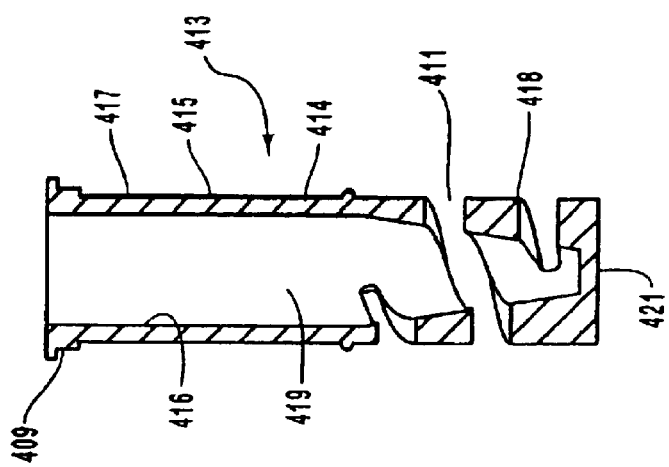
FIG. 26 is a cross sectional side view of the spray nozzle shown in FIG. 25.
Figure 25:
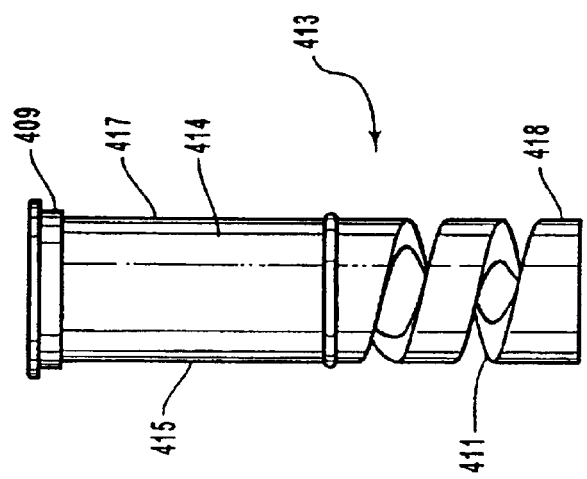
FIG. 25 is an elevated side view of the spray nozzle shown in FIG. 24.

As depicted in FIGS. 25 and 26, spray nozzle 413 comprises a tubular body 414 having an exterior surface 415 and an interior surface 416 each extending between a first end 417 and an opposing second end 418. Encircling and radially outwardly projecting from exterior surface 415 at first end 417 is a stepped flanged 409. Interior surface 416 bounds a channel 419 that radially inwardly slopes at second end 418 to an end wall 421. Extending between interior surface 416 and exterior surface 415 so as to encircle at least a portion of second end 418 is a helical slot 411.

Returning to FIG. 24, during use second end 418 of spray nozzle 413 is passed through fluid port 224 so that stepped flange 409 engages with the leading edge of fluid port 224. In this configuration, second end 418 having helical slot 411 formed thereon is disposed within compartment 220 of mixing bag 202. The fluid component flowing down extension tube 249 enters channel 419 of spray nozzle 413 at first end 417. The fluid component travels down channel 419 and is radially outwardly sprayed through helical slot 411. In turn, the sprayed fluid component functions to wash down the feed component as previously discussed. In alternative embodiments, it is appreciated that spray nozzle 413 or the end thereof can be replaced with any number of different spray heads such as those used in conventional sprinkler systems.

VI. Mixing and Removal of Solution.

During and/or subsequent to feeding of the components into compartment 220 of mixing bag 202, mixer 204 or one of the alternatives thereto is activated so as to mix the components into a homogeneous solution. Specifically, as previously discussed, mixer 204 is repeatedly raised and lowered within compartment 220 under various operating parameters specific to the volume and type of solution being made. One of the benefits of mixers 204, 310, and 374 is that they are able to efficiently mix both large and relatively small amounts of solution with minimal shearing forces and while minimizing the formation of foam. High shearing forces and the formation of foam can be detrimental to some biological solutions.

Although side wall 24 of tank assembly 20 can be any configuration, such as circular as shown in FIG. 2, it has been discovered that improved mixing properties are obtained if the interior configuration of the side wall has a polygonal configuration, such as the hexagonal configuration shown in FIG. 7. The polygonal configuration appears to increase turbulent flow which improves mixing.

As the feed component and the liquid component are mixed within compartment 220, samples can be drawn out and tested through sample tube 428 in communication with delivery tube 420 as depicted in FIG. 1. Likewise, select additives can be added through sample tube 428 which additives then pass through pump 424 and then back into compartment 220 through return tube 430. Examples of additives include serum, acids, bases, lipids, buffers, and trace element components. Once the feed component and liquid component are mixed to a desired amount, typically to a homogenous solution, the solution can be directly dispensed through delivery tube 420, passed through filtration system 500 (as discussed blow), or passed through some other type of system prior to dispensing.

In the embodiment where upper end 214 of mixing bag 202 is secured to support rack 436 by clamp 438 as shown in FIG. 20, mixing bag 202 remains suspended within chamber 60 as the solution is removed from mixing bag 202. In one embodiment, as the solution is removed, mixing bag 202 begins to radially inwardly collapse from upper end 214 to lower end 216. Accordingly, when all of the solution is removed, mixing bag 202 is almost entirely supported by support rack 436. In an alternative embodiment, as the solution is removed, air or some other gas in continually pumped into compartment 220 through air inlet line 444 so as to maintain a positive pressure within mixing bag 202. Mixing bag 202 thus remains partially supported by the side wall of the tank assembly. Inflating mixing bag 202 also helps in removal of all solution therefrom.

Once all of the solution is removed, mixing bag 202 can be refilled for a new batch. Alternatively, mixing bag 202 is disconnected from the various tubes and mixing shaft 208 is disconnected from actuation rod 172. The entire mixing assembly 200 is then removed from chamber 60 through the use of lift 400 where it is then either disposed of or recycled. A new mixing assembly can then be inserted within chamber 60 for the production of a new batch of solution without the need to sterilize or clean tank assembly 20.

VII. Temperature Probe.

As previously discussed, fluid channels 44 in side wall 24 of tank assembly 20 are used for controlling the temperature of the solution within mixing bag 202. Although fluid channels 44 can regulate temperature, they do not actually measure the temperature of the solution. In one embodiment, conventional temperature probes can be inserted into the solution through ports on mixing bag 202. One downside to this embodiment, however, is that the probes must then be sterilized prior to use with a different batch or type of solution.

Figure 27:
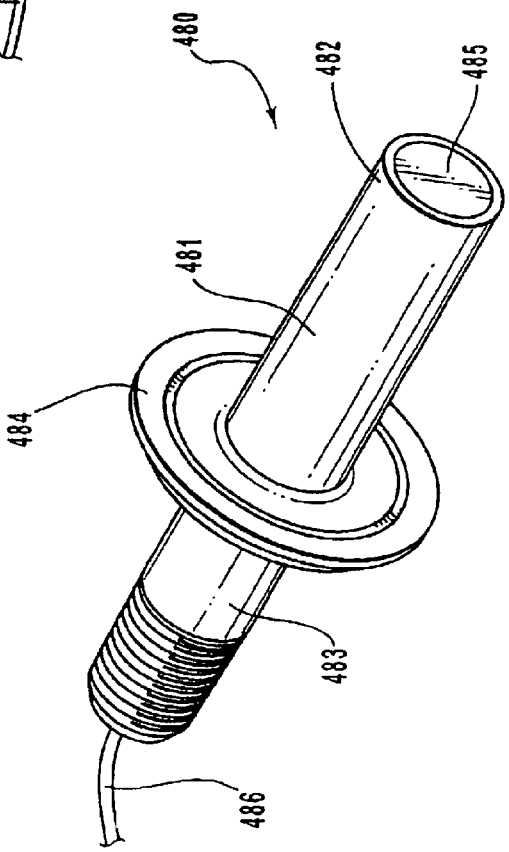
FIG. 27 is a perspective view of a temperature probe.

Accordingly, in one embodiment of the present invention means are provided for continuously sensing the temperature of the solution within compartment 220 of mixing bag 202 without directly contacting the solution. By way of example and not by limitation, depicted in FIG. 27 is a temperature probe 480 having an exterior surface 481 extending between a first end 482 and an opposing second end 483. Outwardly projecting from exterior surface 481 between opposing ends 482 and 483 is a mounting flange 484. First end 482 terminates at a substantially flat end face 485. Projecting from second end 443 is signal wiring 486 for transmitting the signal produced by temperature probe 480.

Figure 28:
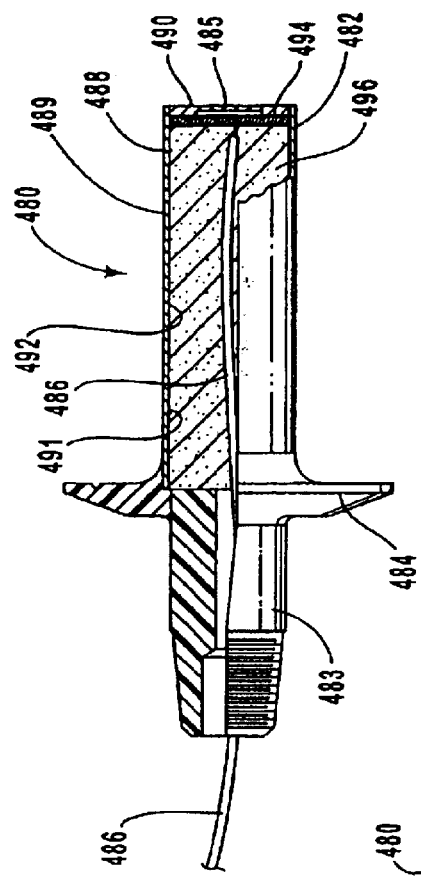
FIG. 28 is a partial cross sectional side view of the temperature probe shown in FIG. 27.

Depicted in FIG. 28, temperature probe 480 is further defined as having a cylindrical housing 488 comprising an encircling peripheral wall 489 and an end wall 490 disposed at first end 482 thereof. Housing 488 is typically comprised of metal, such as stainless steel, and typically has a thickness in a range between about 0.3 mm to about 3 mm. Other materials and thicknesses can also be used. Housing 488 has an interior surface 491 which bounds a cavity 492. Disposed within cavity 492 so as to bias against interior surface 491 of end wall 490 is a thermal sensor 494. In one embodiment thermal sensor 494 comprises a thermal resistor or other configurations of thermal sensitive material, such as in the form of wiring, wherein the electrical resistance of the material changes as the temperature of the material changes. Accordingly, by passing an electrical current through the thermal resistor or other material and measuring the resistance, the temperature at thermal sensor 494 can be measured.

Figure 29:
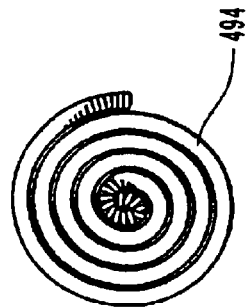
FIG. 29 is a top plan view of the sensor of the temperature probe shown in FIG. 28.

In the embodiment depicted, thermal sensor 494 comprises the wiring out of a conventional linear RTD (resistance thermal device) probe. As depicted in FIG. 29, the linear wiring has been coiled into a substantially flat circular configuration. In one embodiment, sensing element 494 is comprised of platinum but can also be comprised of nickel, copper, nickel-iron or other thermal resistance materials. Extending from thermal sensor 494 within cavity 492 is signal wiring 486. Signal wiring 486 is used for passing a current through thermal sensor 494. The remainder of cavity 492 is filled with an insulative plug 496 which surrounds signal wiring 486. In one embodiment, insulative plug 496 is comprised of a ceramic such as aluminum oxide (alumina). Other types of insulation can also be used. The above configuration of thermal sensor 494 and the positioning of insulative plug 496 focuses the temperature sensing path of thermal sensor 494 toward end wall 490.

Figure 30:
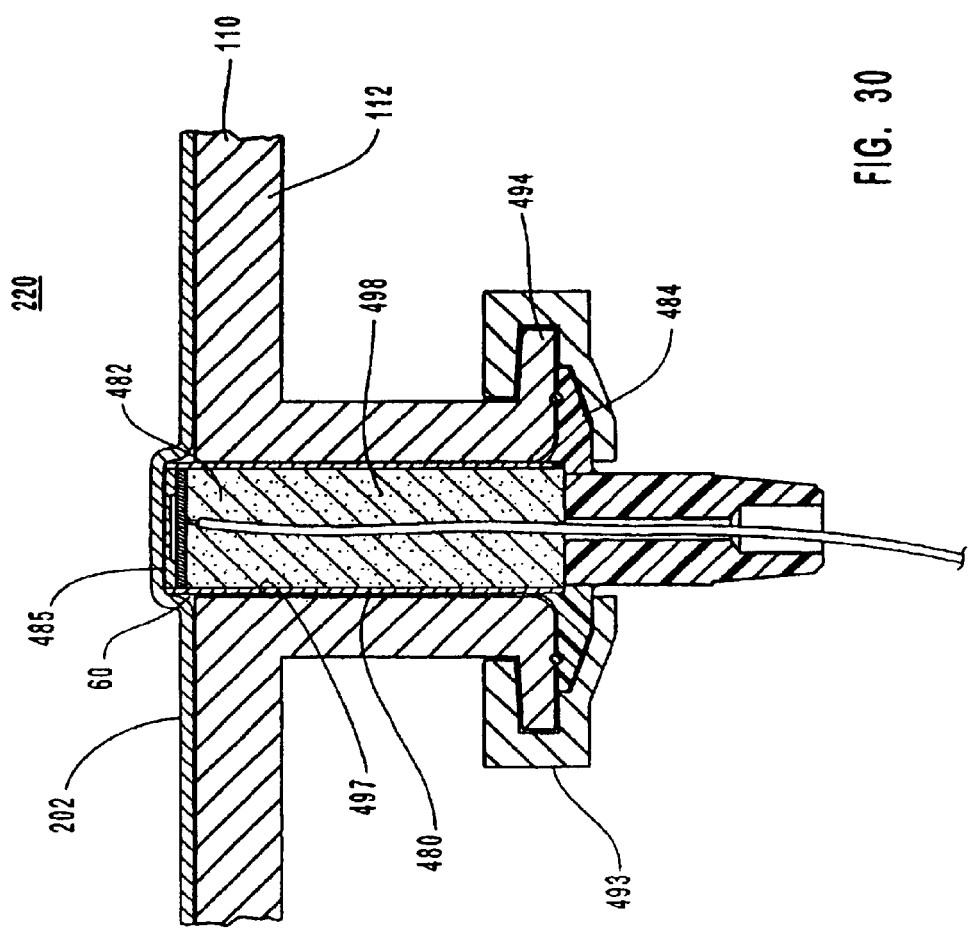
FIG. 30 is a partial cross sectional side view of the temperature probe shown FIG. 27 mounted to the floor of the tank assembly shown in FIG. 1.

In one embodiment, as depicted in FIG. 30, to facilitate use of temperature probe 480 a hole 497 is formed through base floor 112 of floor 110. A tubular collar 498 is mounted, such as by welding, to the bottom surface of base floor 112 so as to encircle hole 497. A flange 499 outwardly projects from the free end of collar 498. First end 482 of temperature probe 480 is advanced through tubular collar 498 so that mounting flange 484 of temperature probe 480 biases against flange 499. A clamp 493, such as a hinged tri-clamp or any other type of clamp, is then used to removably secure flanges 484 and 499 together. In this secure but removable configuration, at least a portion of first end 482 of temperature probe 480 projects past the interior surface of base floor 112 and into chamber 60.

In one embodiment, end face 485 is spaced apart from the interior surface of base floor 112 by a distance in a range between about 1 mm to about 5 mm. Other distances can also be used. In this configuration, mixing bag 202 biases directly against end face 485 of temperature probe 480. This biasing force increases as mixing bag 202 is filled with the solution.

During operation, temperature probe 480 measures the surface temperature of mixing bag 202, and thus tie temperature of the solution therein, without penetrating mixing bag 202 or being in direct contact with the solution. As such, there is no need to sterilize or clean temperature probe 480 as fluid preparation system 10 switches between the manufacture of different batches or types of solution. To accurately determine the temperature of the solution, the sensed temperature is calibrated to offset the thermal lag of mixing bag 202. Accuracy of the measured temperature depends in part on end face 485 of temperature probe 480 being clean and being in intimate contact with mixing bag 202. In the depicted embodiment, temperature probe 480 is mounted on base floor 112 so as to utilize the weight of the solution in maintaining intimate contact between temperature probe 480 and mixing bag 202 throughout the process.

In alternative embodiments, it is appreciated that end face 485 of temperature probe 480 can be positioned flush with or below the interior surface of base floor 112. Furthermore, temperature probe 480 can be mounted on other portions of floor 102 or on side wall 24. It is also appreciated that temperature probe 480 can be mounted in any number of fixed or removable manners to tank assembly 20.

VIII. Filtration System.

Figure 31:
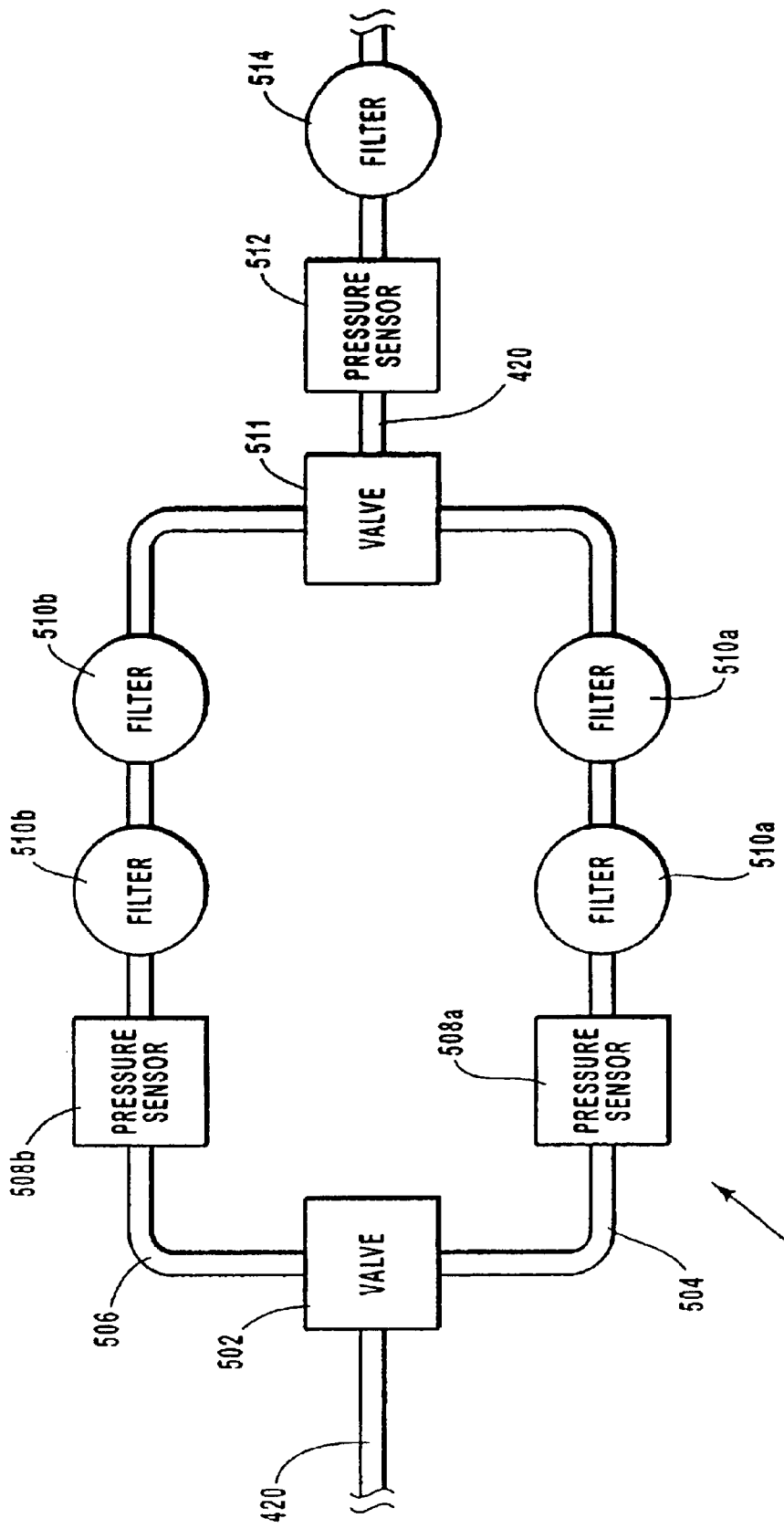
FIG. 31 is a schematic illustration of the filter assembly of the fluid preparation system shown in FIG. 1.

As depicted in FIG. 31, filtration system 500 comprises a valve 502 which splits delivery tube 420 into a first leg 504 and a discrete second leg 506. As previously discussed, valve 502 can simply comprise a tee joint coupled with delivery tube 420 and legs 504 and 506 acting in combination with external clamps which selectively close around either first leg 504 and/or second leg 506. Alternatively, there are a variety of other conventional types of electrical and manual valves that can be used.

Coupled with each leg 504 and 506 is a pressure sensor 508 and one or more filters 510. The type and number of filters 510 depends upon the material being processed and the desired properties of the end product. In one embodiment, filters 510 can comprise conventional bacterial filters to facilitate sterilization of the solution. Once the solution passes through filters 510, legs 504 and 506 connect together as a valve 511 to reestablish delivery tube 420. The solution then again passes by or through a pressure sensor 512 and then through a final filter 514.

During operation, valves 502 and 511 are set so that the solution passes through only one of legs 504 or 506. For example, valves 502 and 511 can initially be set so that the solution entering from delivery tube 420 passes through first leg 504. As filters 510a become partially occluded by filtered material, the fluid back pressure is sensed by pressure sensor 508a. When filters 510a are sufficiently occluded as determined by a preset back pressure, valves 502 and 511 are switched so that the fluid passes through leg 506. Filters 510a are then replaced with clean filters. When filters 510b become occluded the process is repeated. Accordingly, by using this configuration of filtration system 500, filtration of the solution can be continuous.

Pressure sensor 512 is either directly or indirectly coupled with pump 424 (FIG. 1) so as to control the flow rate of solution through delivery tube 420. That is, as the pressure drops at pressure sensor 512 due to the increased occlusion of filters 510a or 510b, the speed of pump 424 can be increased so that the flow rate of solution is relatively constant. Likewise, when filtration system 500 switches to new filters causing the pressure to increase, pump 424 can be slowed. Where it is not desired to have a constant flow rate, pressure sensor 512 is not required.

As will be discussed below with regard to dispenser assembly 700, filter 514 is used for final sterilization of the solution and can be considered either part of filtration system 500 or dispenser assembly 700.

In alternative embodiments, it is appreciated that filtration system 500 can comprise three or more discrete legs. Alternatively, filtration system 500 need not include two or more separate legs but can simply comprise a pressure sensor and one or more filters through which deliver tube 420 passes. In this embodiment, however, it is necessary to stop the filtration process to replace the filters. In yet other embodiments, pressure sensor(s) 508 are not required. In theses embodiments, filters 510 can simply be replaced after predetermined periods of use.

IX. Pressure Sensor Assembly.

The various pressure sensors 508 and 512 depicted in FIG. 31 can comprise any conventional pressure sensor which is placed in direct communication with the solution so as to measure the fluid pressure thereof. In an alternative embodiment, however, pressure sensors can be positioned so that they are not in direct fluid communication with the solution. As a result, it is not necessary to sterilize or clean the pressure sensors as fluid preparation system 10 is switched between the manufacture of different batches or types of solution.

Figure 32:
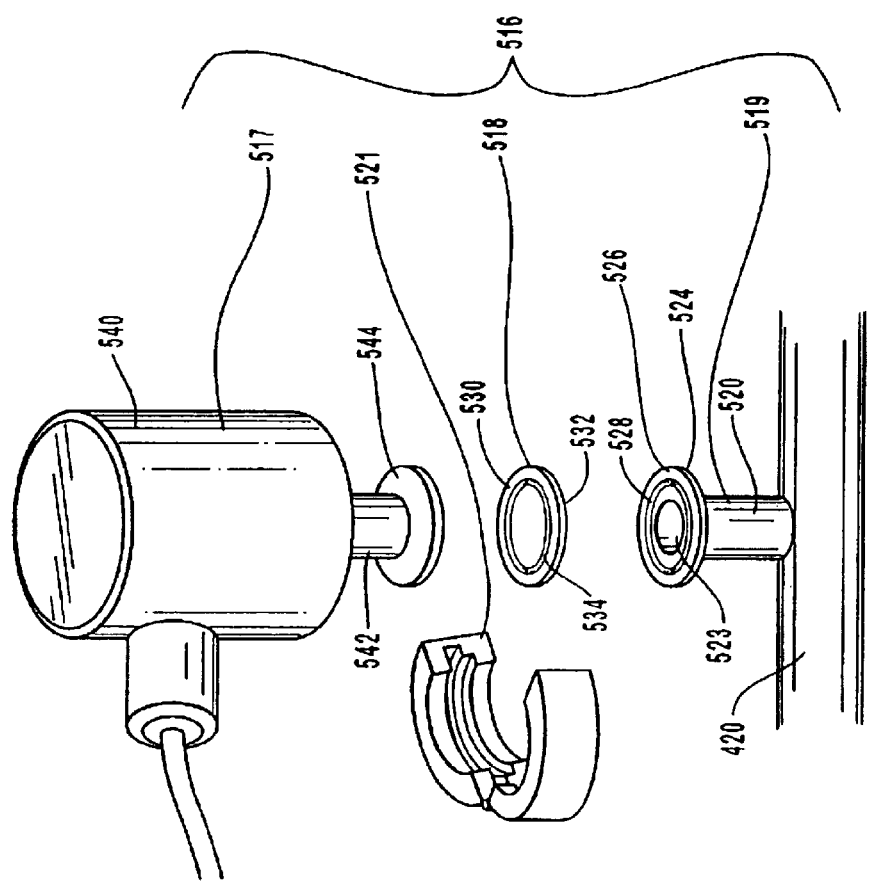
FIG. 32 is an exploded perspective view of a pressure sensor assembly used in association with the filtration system shown in FIG. 31.

By way of example and not by limitation, depicted in FIG. 32 is one embodiment of a pressure sensor assembly 516. Assembly 516 comprises a pressure sensor 517, a diaphragm 518, a sensing port 519, and a clamp 521. Sensing port 519 comprises a tubular stem 520 projecting from delivery tube 420. Stem 520 bounds a passageway 523 that communicates with delivery tube 420. Encircling and radially outwardly projecting from the free end of stem 520 is a flange 524. Flange 524 terminates at an engagement face 526. A continuous sealing groove 528 is recessed on engagement face 526 so as to encircle passageway 523.

Figure 33:
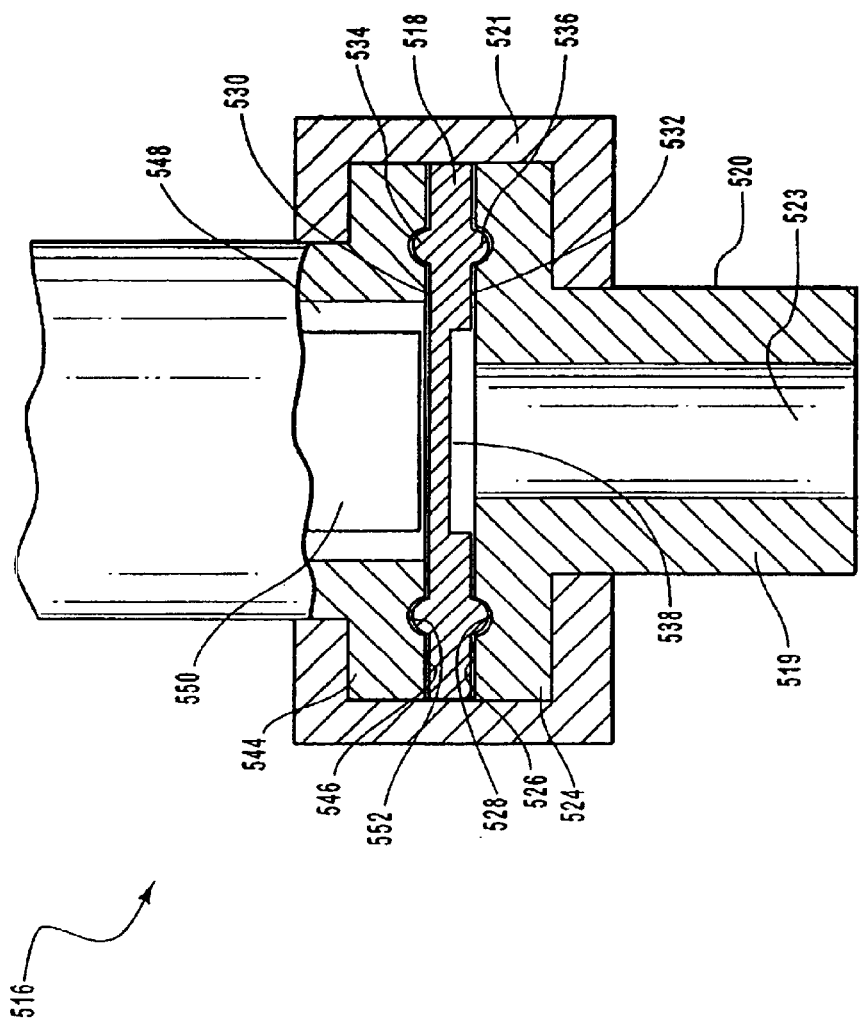
FIG. 33 is a cross sectional side view of the pressure sensor assembly shown in FIG. 32 in an assembled state.

As depicted in FIGS. 32 and 33, diaphragm 518 has a first side 530 and an opposing second side 532. A sealing ridge 534 and 536 outwardly projects in a continuous loop from first side 530 and second side 532, respectively. Recessed into second side 532 within the area bounded by sealing ridge 536 is a pocket 538. Diaphragm 518 is removably seated on engagement face 526 of sensing port 519 so that sealing ridge 536 is received within sealing groove 528. In this configuration, diaphragm 518 covers the opening to passageway 523 with pocket 528 being aligned therewith.

Pressure sensor 517 is a standard "off-the-shelf" item such as a conventional (digital or analog pressure transducer. One example of pressure sensor 517 comprises the Mini Pressure Transducer produced by Anderson Instrument Co. out of Fultonville, N.Y. As depicted, pressure sensor 517 comprises a body 540 having a tubular stem 542 projecting therefrom. Encircling and outwardly projecting from the free end of stem 542 is a flange 544. An engagement face 546 is formed on one side of flange 544. Engagement face 546 encircles an opening 548 in which a sensor 550 is movably disposed. A continuous sealing groove 552 is recessed on engagement face 546 so as to encircle opening 548.

Engagement face 546 is received on first side 530 of diaphragm 518 so that sealing ridge 534 is received within sealing groove 552. In this configuration sensor 550 is biased against first side 530 of diaphragm 518 opposite of pocket 538.

Clamp 521 is used to secure flanges 524 and 544 together so that diaphragm 518 seals against sensing port 519 and so that sensor 550 is held against diaphragm 518. The seal prevents solution passing through delivery tube 420 and entering passageway 523 from leaking out between flange 524 and diaphragm 518. In one embodiment, clamp 521 comprise a conventional hinged tri-clamp such as available from Tri-Clover out of Kenosha, Wis. Alternatively, any other type of removable clamp or securing structure can be used that produces the desired coupling.

During operation, the solution passing through delivery tube 420 enters passageway 523 of sensing port 519 and pushes against diaphragm 518. In turn, diaphragm 518 pushes against sensor 550. Pocket 538 is formed so as to decrease the thickness of diaphragm 518 at that location, thereby increasing the pressure sensitivity thereat. Readings or signals from sensor 550 are used to determine the actual or relative fluid pressure of the solution.

Because the solution does not directly contact clamp 521 or pressure sensor 517, these components do not have to be sterilized or otherwise cleaned when fluid preparation system 10 is switched between the manufacture of different batches or types of solution. The remainder of pressure sensor assembly 516, namely, diaphragm 518 and sensing port 519, are relatively inexpensive and can simply be replaced during the manufacture of different solutions.

Diaphragm 518 is typically molded, such as by compression or injection molding, from a soft flexible material. Examples of materials that can be used include neoprene, silicone, EPDM, Viton, Kalrez, Teflon, polypropylene, polyethylene, polyolefin, Buna, and nitrile rubber as well as other moldable plastic compounds. The above materials can also be reinforced with glass, carbon, or other types of fibers. The portion of diaphragm 518 that pushes against sensor 550 typically has a thickness in a range between 2 mm to about 20 mm with about 3 mm to about 10 mm being more common.

Figure 34:
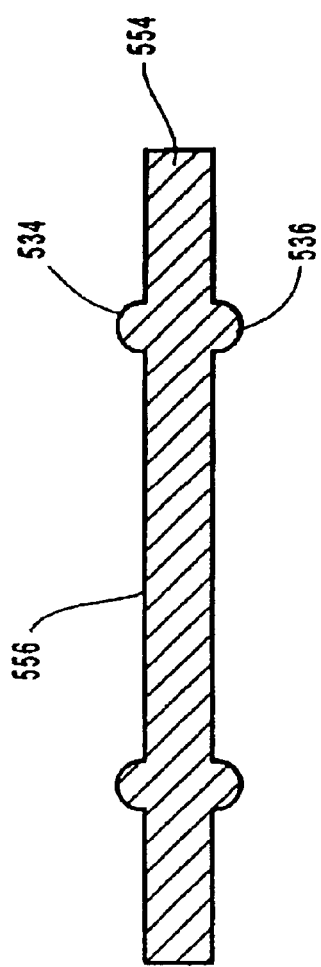
FIG. 34 is an elevated side view of an alternative embodiment of a diaphragm of the pressure sensor assembly shown in FIG. 32.
Figure 35:
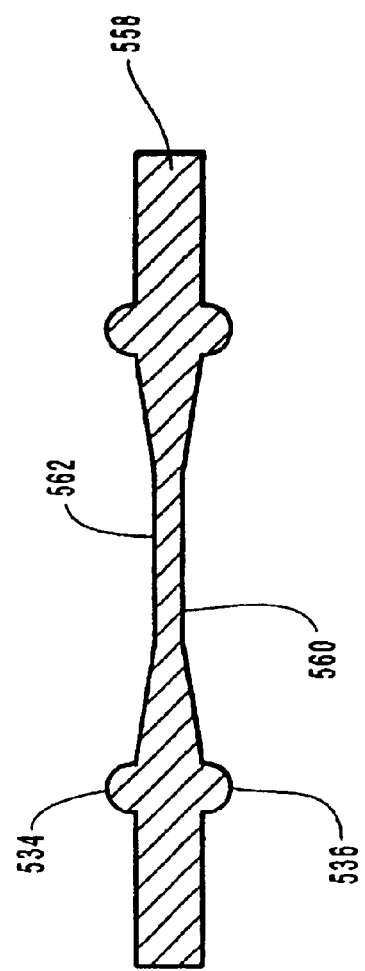
FIG. 35 is an elevated side view of an alternative embodiment of the diaphragm shown in FIG. 34.

Depicted in FIGS. 34 and 35 are alternative embodiments of diaphragm 518 wherein like elements are identified by like reference characters. Depicted in FIG. 34 is a diaphragm 554 wherein a central sensing portion 556, i.e., the area bounded by sealing ridges 534 and 536, has a substantially uniform thickness. This thickness can be any desired amount to produce the desired sensitivity. Depicted in FIG. 35 is a diaphragm 558 wherein a central sensing portion 560 tapers on each side from sealing ridges 534 and 536 to a central flat portion 562. In yet other embodiments, one side of central sealing portion 560 can be flat as shown with diaphragm 554 while the other side is tapered as shown with diaphragm 558. Other combinations and alternative configurations can also be used.

X. Dispensing System.

Once the solution passes through filtration system 500, the solution is dispensed either directly into its end use environment or into a container. When it is not necessary that the solution be sterile, the solution can simply be dispensed from delivery tube 420 in any conventional manner. Where the solution must remain sterile after passing through the filters, it is necessary that a sterile fluid coupling be formed between delivery tube 420 and the end storage container.

By way of example and not by limitation, depicted in FIG. 36 is one embodiment of a sterile fluid dispensing system 700. Dispensing system 700 comprises a delivery assembly 702, a collector assembly 704, and a sterilizer 706. Delivery assembly 702 comprises filter 514, a flexible extension tube 712, and a rigid fill tube 714. Filter 514 is a final sterilizing filter which is designed so that all solution passing therethrough is completely sterile or is at least filtered to the desired parameters of the end product solution. As such, the solution prior to filter 514 need not be sterile. Filter 514 has an inlet port 708 and an outlet port 710. Inlet port 708 is configured to selectively and removeably couple with delivery tube 420 while outlet port 710 is coupled in sealed fluid communication with a first end 711 of extension tube 712.

Fill tube 714 is coupled in sealed fluid communication with a second end 713 of extension tube 712. Depicted in FIG. 37, fill tube 714 comprises a tubular, cylindrical body 715 having an interior surface 716 and an exterior surface 718 each extending between a first end 720 and an opposing second end 722. Interior surface 716 bounds a channel 724 longitudinally extending through fill tube 714. Encircling and radially outwardly projecting from first end 720 of body 715 is a flange 728. Projecting from first end 720 of body 715 in longitudinal alignment therewith is a barbed port 717. Barbed port 717 is received within second end 713 of extension tube 712 so as to affect a sealed fluid communication therewith. In alternative embodiments, any conventional form of connection can be used to fluid couple fill tube 714 to extension tube 712.

Formed at second end 722 of body 715 is a tapered, substantially frustoconical nose 730. Nose 730 bounds an outlet 732 in fluid communication with channel 724. A locking groove 734 encircles and is recessed into exterior surface 718 of nose 730. As depicted in FIG. 37 and 38, mounted within outlet 732 and secured to interior surface 716 of nose 70 are a pair of crossing puncture blades 736. Each blade 736 has a sharpened outer edge 738 that projects beyond the end of nose 730.

Figure 39:
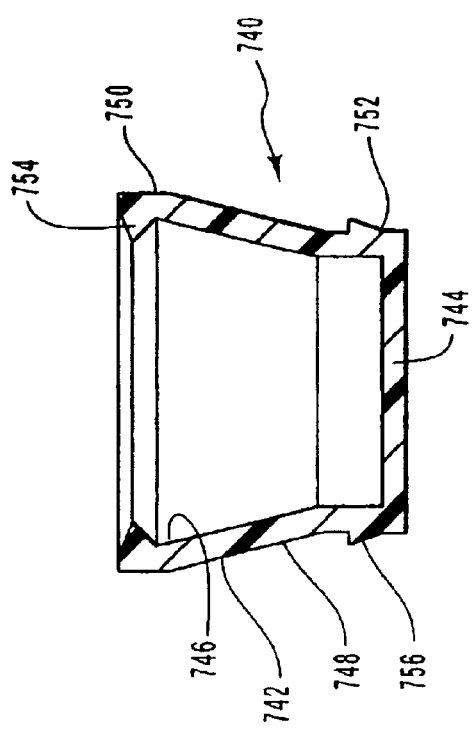
FIG. 39 is a cross sectional side view of a cap on the fill tube shown in FIG. 37.

As depicted in FIGS. 37 and 39, a cap 740 is removably mounted on second end 722 of fill tube 714 50 as to seal off outlet 732. Cap 740 has an annular substantially frustoconical side wall 742 that terminates at a end plate 744. Side wall 742 has an interior surface 746 and an exterior surface 748 that each extend between a first end 750 and an opposing second end 752. Radially inwardly projecting from interior surface 746 at first end 750 is an annular locking ridge 754. Encircling and radially outwardly projecting from exterior surface 748 at second end 752 is a barb 756. As depicted in FIG. 37, cap 740 is received over nose 730 so that locking ridge 754 of cap 740 is received within locking groove 734, thereby forming a sealed connection between cap 740 and fill tube 714. In one embodiment, fill tube 714 is made of a metal, such as stainless steel, while cap 740 is formed of a molded plastic. In other embodiment, fill tube 714 can also be made of rigid plastics, composites, or other materials.

In its fully assembled state, as depicted in FIG. 36, delivery system 702 is sterilized as a unit such as by ionizing radiation or other conventional sterilization techniques.

Collector assembly 704 as shown in FIG. 36 comprises a flexible extension tube 760 having a first end 762 and an opposing second end 764. Second end 764 of extension tube 760 is coupled in sealed fluid communication with a container 765. Container 765 can comprise any rigid or flexible container used for holding sterile fluids. Container 765 can be disposable or recyclable. For example, in one embodiment container 765 comprises a bag made of the same materials and methods as previously discussed with regard to mixing bag 202.

Figure 40:
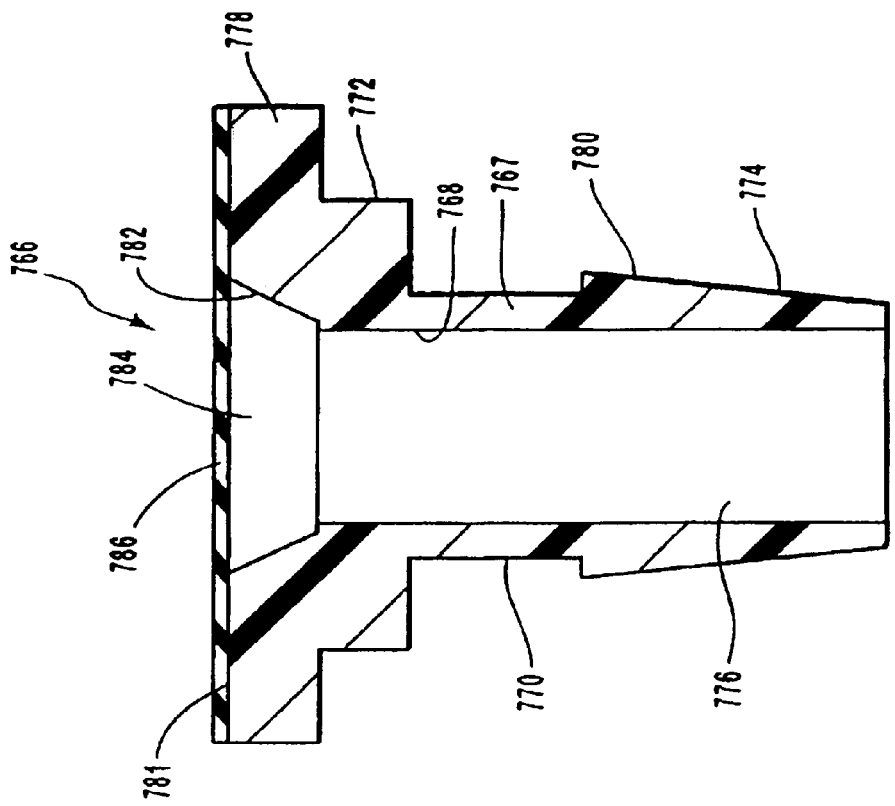
FIG. 40 is a cross sectional side view of a fill port of the collector assembly shown in FIG. 36.

Mounted at first end 762 of extension tube 760 is a fill port 766. As depicted in FIG. 40, fill port 766 comprises a tubular, substantially cylindrical body 767 having an interior surface 768 and an exterior surface 770 each extending between a first end 772 and an opposing second end 774. Interior surface 768 bounds a channel 776 longitudinally extending through fill port 766. Encircling and outwardly projecting from exterior surface 770 at first end 772 is an annular flange 778. Encircling and outwardly projecting from exterior surface 770 at second end 774 is an annular barb 780. Second end 774 of fill port 766 is received in sealed fluid communication within first end 762 of extension tube 760. In other embodiments, other conventional connections can be used to couple fill port 766 with extension tube 760. For example, rather than using barb 780, fill port 766 can be heat sealed, welded, or otherwise secured to extension tube 760.

Fill port 766 terminates at an end face 781 at first end 772. Interior surface 768 of fill port 766 includes a sloping, substantially frustoconical seat 782 extending from end face 781. Seat 782 bounds an opening 784 to channel 776. Mounted on end face 781 so as to extend across opening 784 is a membrane 786. In this configuration, membrane 786 seals opening 784 closed. Membrane 786 is typically made of a sheet of polymeric material that can be selectively punctured.

In its fully assembled state, as depicted in FIG. 36, collector assembly 704 is completely sealed. In this configuration, collector assembly 704 is sterilized such as by ionizing radiation or other conventional techniques of sterilization.

Figure 41:
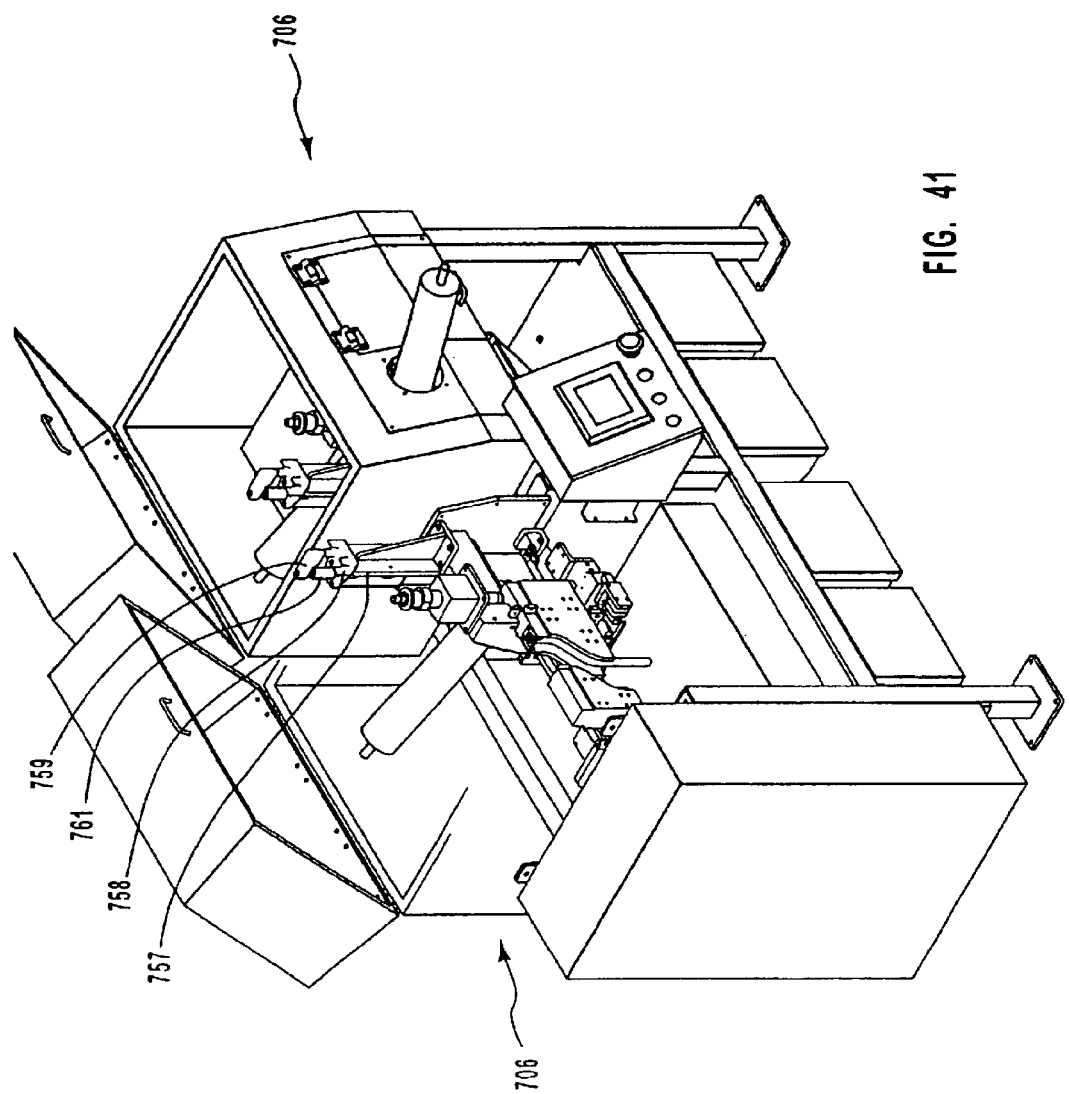
FIG. 41 is a perspective view of a pair of adjacent sterilizers.

Depicted in FIG. 41 is one embodiment of two adjacently disposed sterilizers 706, one of such sterilizers being shown in a partially disassembled state. Mounted on each sterilizer 706 is an automated hose clamp 757. Hose clamp 757 comprises a rack 758 on which a flexible hose or tube is selectively placed. A piston 761 selectively raises and lowers an arm 759 projecting therefrom. When arm 759 is in the lowered position, arm 759 biases against the hose so as to pinch the hose closed. As arm 759 is raised, fluid is allowed to flow through the hose.

Figure 42:
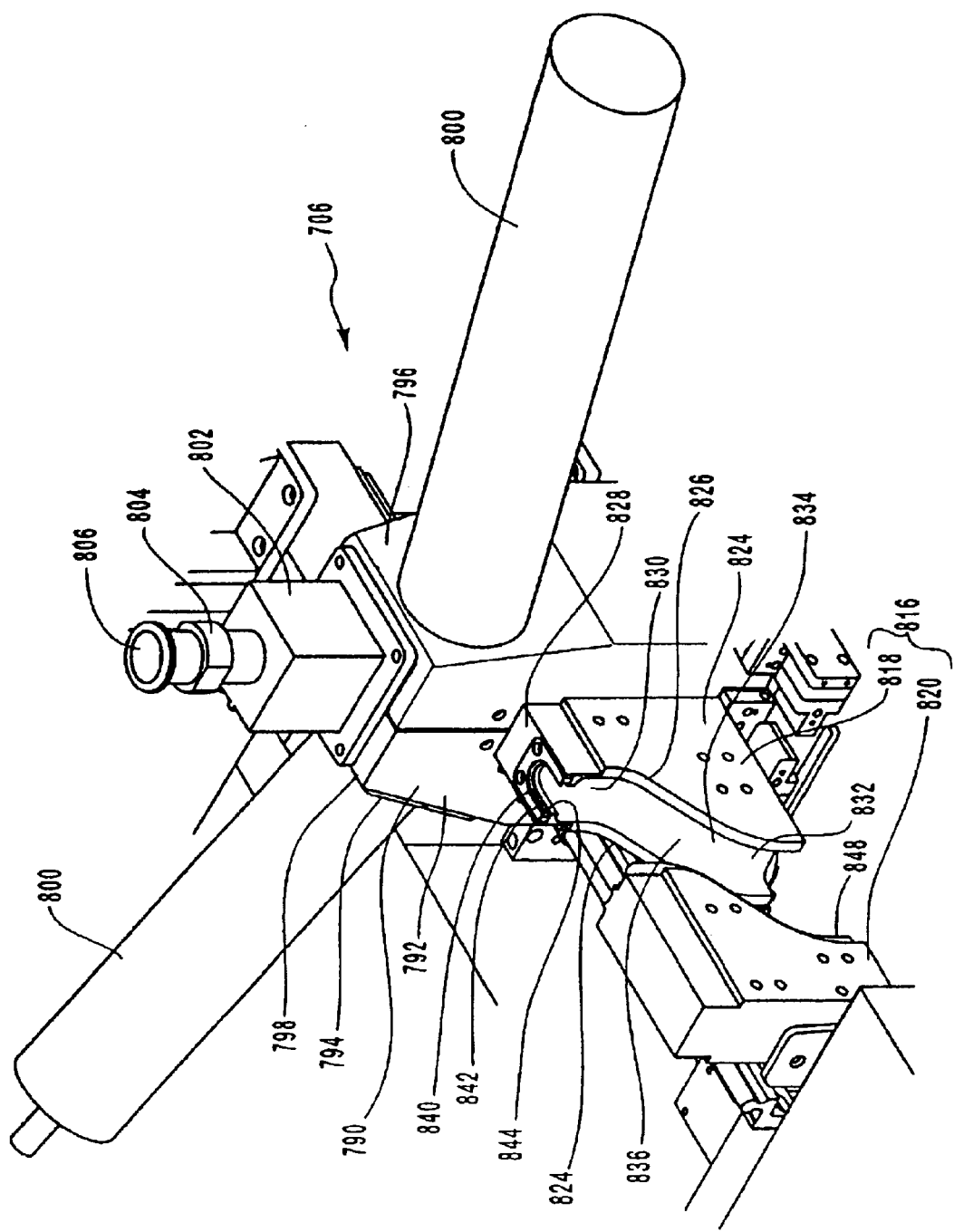
FIG. 42 is a enlarged perspective view of the internal components of the sterilizer shown in FIG. 41.
Figure 43:
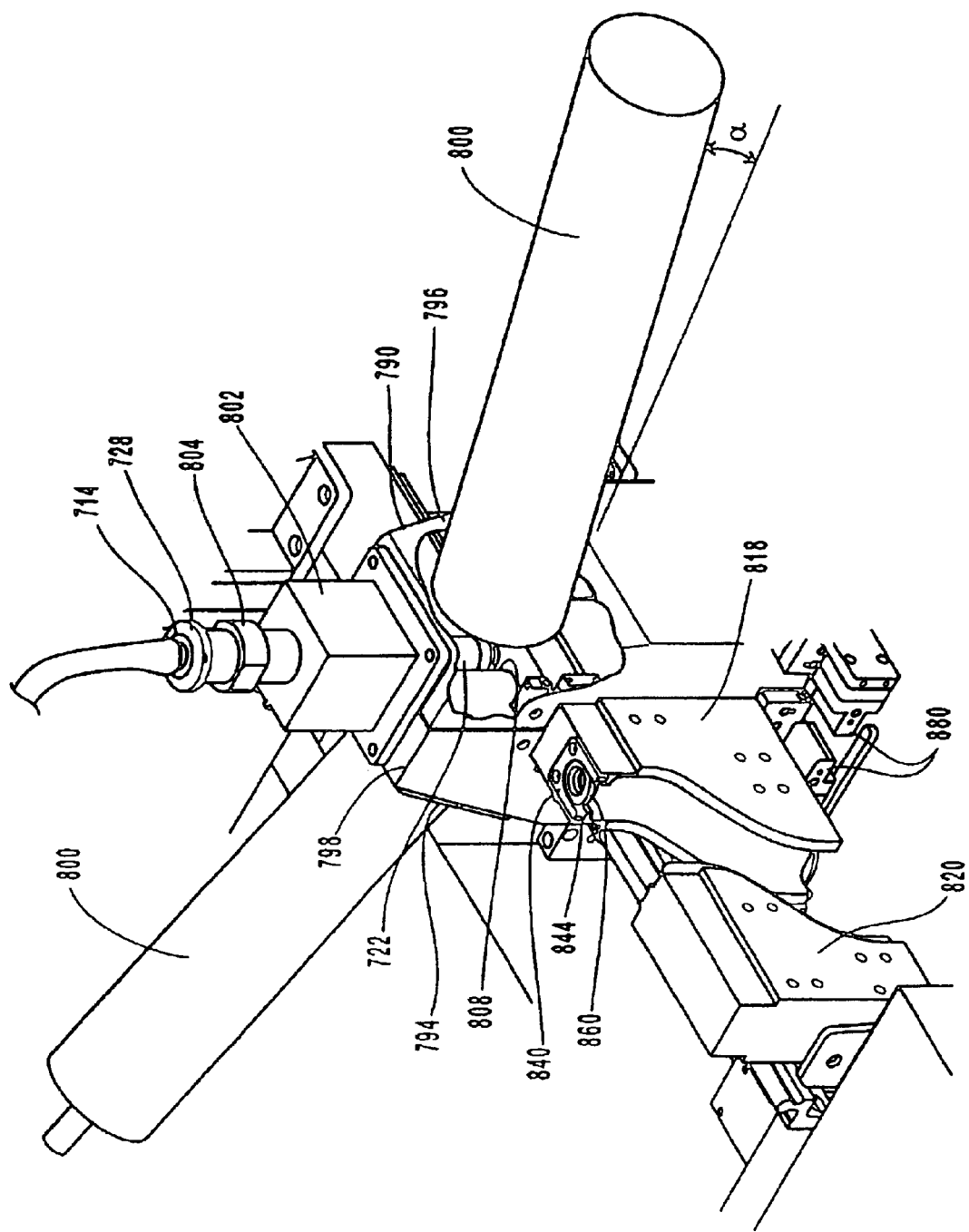
FIG. 43 is a partially cut away perspective view of the sterilizer shown in FIG. 42.

As depicted in FIG. 42, sterilizer 706 comprises a housing 790 having a front face 792 extending between opposing side faces 794 and 796. Also extending between side faces 794 and 796 is a top face 798. As depicted in FIG. 43, a cavity 808 is formed within housing 790. Projecting from each side face 794 and 796 so as to be in alignment with cavity 808 is an electron beam generator 800. Each generator 800 communicates with cavity 808 through a corresponding channel formed on housing 790. Although not required, in the embodiment depicted, generators 800 are disposed at an angle α in a range between about 15° to about 45° relative to the horizontal. One example of an electron beam generator is the E-Beam module available from USHIO America out of Cyprus, Calif.

Each electron beam generator 800 generates an electron field within cavity 808 so as to sterilize cavity 808 and all structure placed therein. During operation of generators 800, cavity 808 is continually flooded with a non-oxidizing gas, such as nitrogen. The non-oxidizing gas displaces any oxygen from within cavity 808. Subjecting oxygen to the electron field could convert the oxygen to ozone which could produce a corrosive effect. To prevent the surrounding environment from being exposed to the electron field, housing 79 is formed of stainless steel or other shielding materials in sufficient thickness to block any harmful emission of the electron field.

Mounted on top face 798 of housing 790 is a plunger 802 which operates a tubular piston 804. Tubular piston 804 bounds a passageway 806 (FIG. 42) that communicates with cavity 808. As depicted in FIG. 43, piston 804 is configured to receive fill tube 714 within passageway 806 so that flange 728 of fill tube 714 rests on piston 804. In this configuration, second end 722 of fill tube 714 is received within cavity 808. As will be discussed below in greater detail, plunger 802 and piston 804 are configured to securely retain fill tube 714 when disposed therein and to selectively raise and lower fill tube 714.

Returning to FIG. 42, slidably mounted so as to selectively extend into and out of housing 790 through front face 792 is a shuttle assembly 816. Shuttle assembly 816 comprises a female shuttle 818 and a male shuttle 820. Female shuttle 818 has opposing side faces 822 and 824 with a front face 826 and a top face 828 each extending therebetween. Front face 826 has a sloping step shaped configuration. Specifically, front face 826 has a substantially vertical upper portion 830, a substantially vertically lower portion 832, and an outwardly sloping central portion 834 extending therebetween. Recessed into and extending along the length of front face 826 so as to have substantially the same sloping configuration as front face 826 is an open channel 836.

Mounted flush on top face 828 at the intersection with front face 826 is a substantially U-shaped retaining collar 840. Collar 840 has an interior face 842 with a substantially U-shaped groove 844 recessed thereon.

Figures 44, 45:
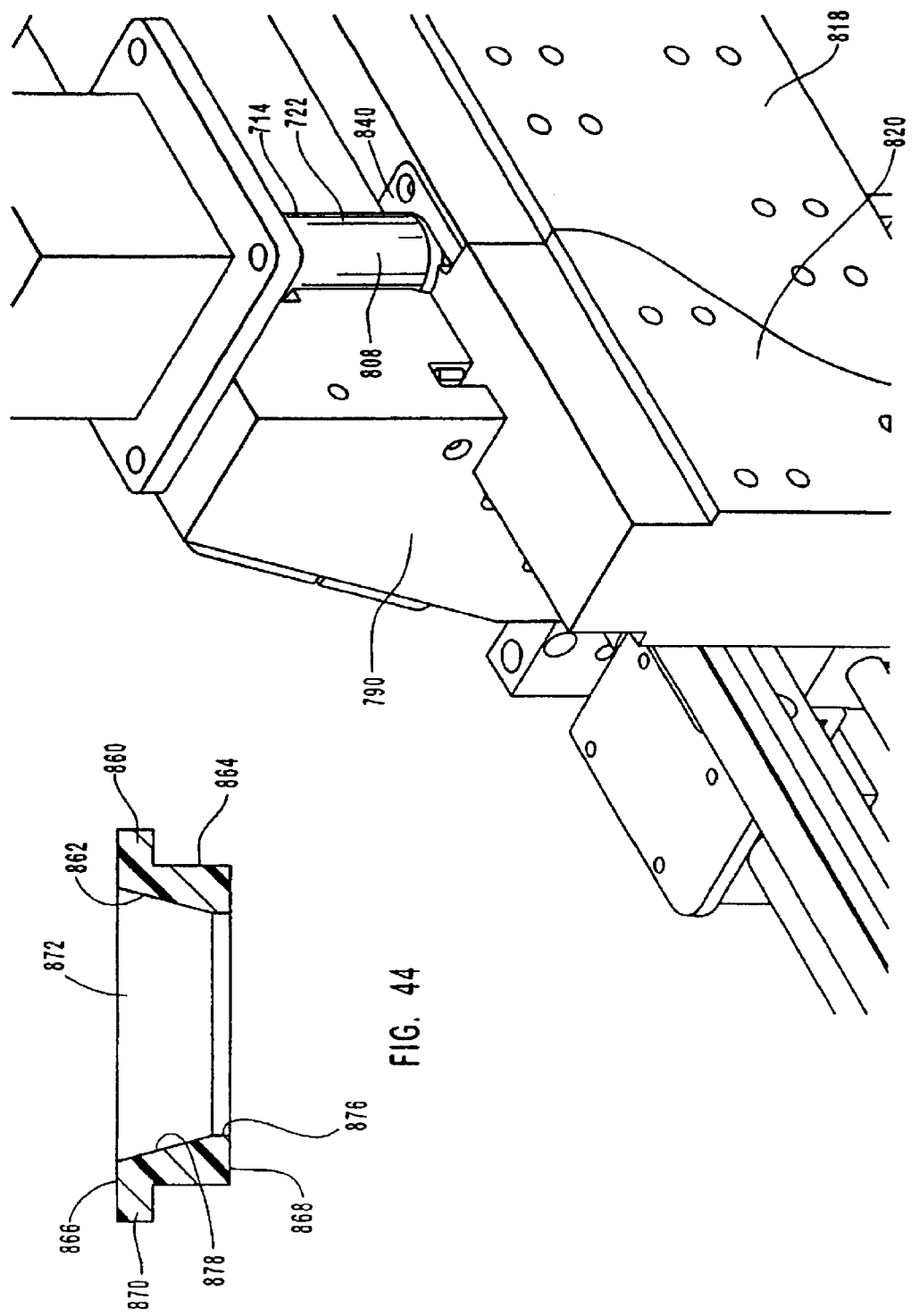
FIG. 44 is a cross sectional side view of a cap remover.
FIG. 45 is a perspective view of the sterilizer of FIG. 43 with the shuttles thereof moved into the housing.

Male shuttle 820 has a front face 848. As discussed and depicted below in greater detail, front face 848 of male shuttle 820 is configured to complementarily mate in close tolerance with front face 826 of female shuttle 818 while leaving channel 836 open. In general, shuttles 818 and 820 are operable between one of three positions. In a first position as depicted in FIG. 42, front face 848 of male shuttle 820 is separated from front face 826 of female shuttle 818 with both front faces 826 and 848 being disposed outside of housing 790. In a second position, male shuttle 820 is moved to mate with female shuttle 818. In the third position, as depicted in FIG. 45, mated shuttles 818 and 820 are moved into housing 790 such that retaining collar 840 is disposed in alignment with cavity 808.

During use, fill tube 714 is slidably received within opening 806 of tubular piston 804 as previously discussed and depicted in FIG. 43. Once fill tube 714 is positioned, electron beam generators 800 are activated so that the electron field is generated within cavity 808, thereby sterilizing second end 722 of fill tube 714. Extension tube 712 of delivery assembly 702 (FIG. 36) is placed on rack 758 of hose clamp 757 (FIG. 41). Arm 759 is then lowered so as to temporarily close off extension tube 712.

A cap remover 860 is removably slid within groove 844 of retaining collar 840. As depicted in FIG. 44, cap remover 860 has an interior surface 862 and an opposing exterior surface 864 each extending between a top end face 866 and a bottom end face 868. Encircling and radially outwardly projecting from exterior surface 864 at top end face 866 is an annular flange 870. Interior surface 862 bounds a channel 872 that extends through cap remover 860. Interior surface 862 comprises cylindrical portion 876 that extends from bottom end face 868 and an inwardly sloping frustoconical tapered portion 878 that extends from top end face 866 to cylindrical portion 876. In this configuration, cylindrical portion 876 has a diameter slightly smaller than the diameter of cap 740 at barb 756.

Cap remover 860 is manually positioned within retainer collar 840 by sliding flange 870 into groove 844. Once positioned, male shuttle 820 is mated with female shuttle 818 so as to lock cap remover 860 in place. The mated shuttles are then moved into housing 790, as illustrated in FIGS. 45 and 46, so that cap remover 860 is vertically aligned and exposed to cavity 808.

Figures 46, 47:
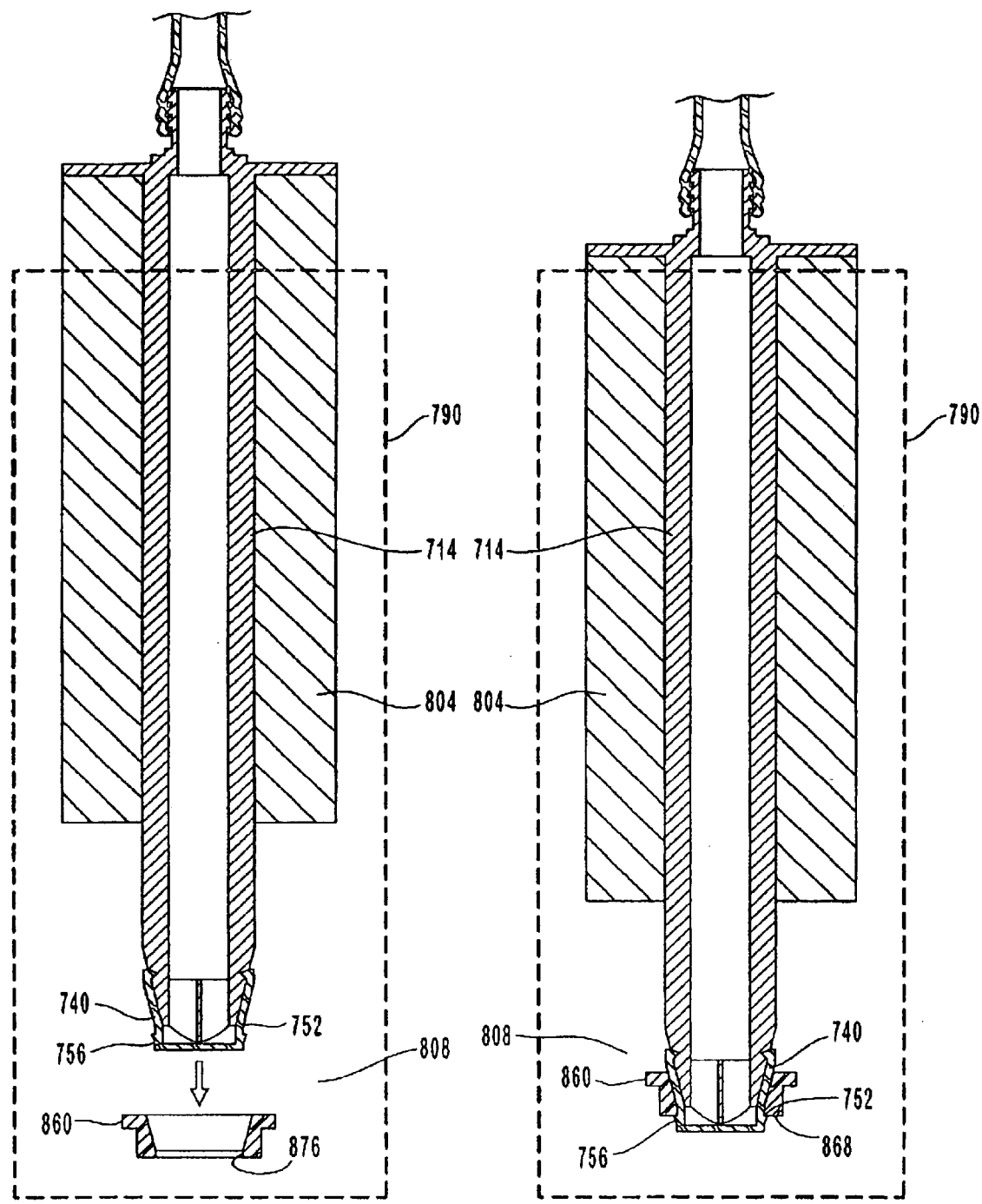
FIG. 46 is a cross sectional side view of the fill tube of FIG. 37 disposed with the sterilizer in vertical alignment with the cap remover.
FIG. 47 is a cross sectional side view of the assembly shown in FIG. 46 with the cap of the fill tube being mated with the cap remover.

Next, as depicted in FIGS. 46 and 47, piston 804 drives fill tube 714 downward causing second end 752 of cap 740 to pass through cap remover 860. Annular barb 756 is resiliently compressed as it passed through cylindrical portion 876 of the interior surface of cap remover 860, but then radially outwardly expands as it passes bottom end face 868. As a result, annular barb 756 rests against bottom end face 868, thereby locking cap 740 in engagement with cap remover 860.

Figure 48:
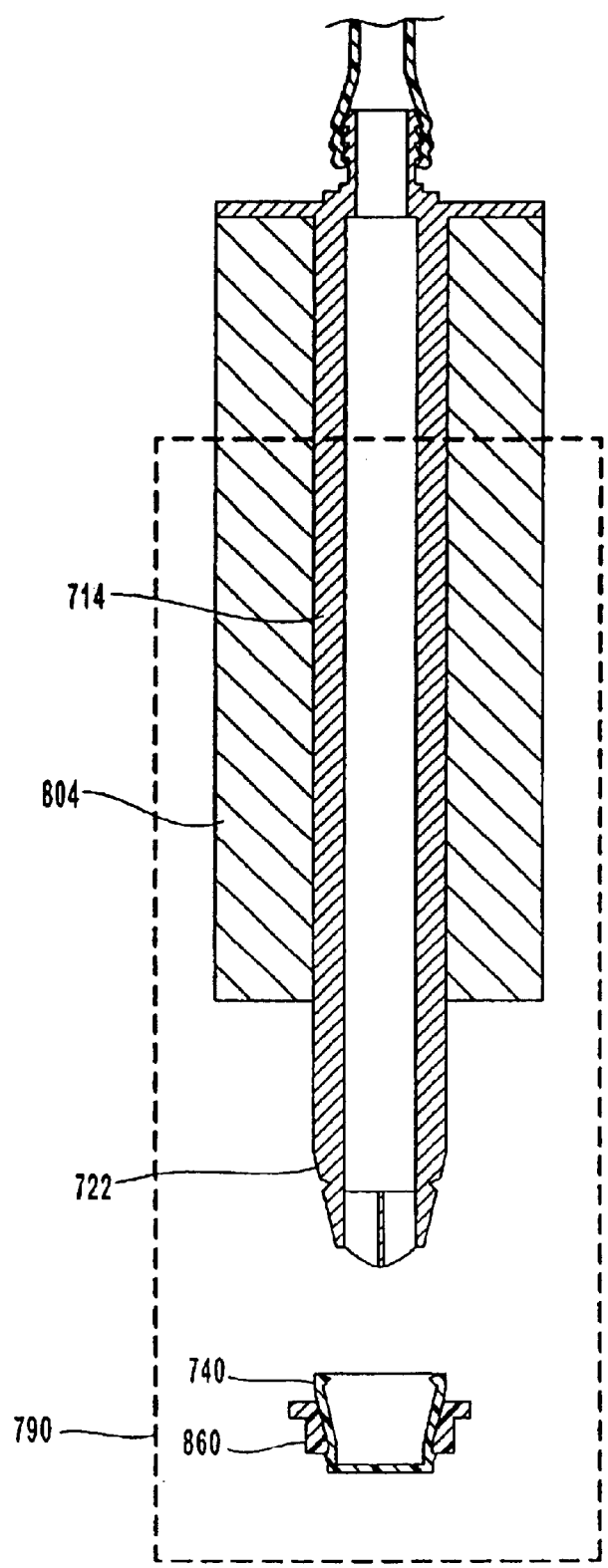
FIG. 48 is a cross sectional side view of the assembly shown in FIG. 47 with the cap being removed from the fill tube.

As depicted in FIG. 48, piston 804 then moves fill tube 714 back to the raised position. As a result of the engagement between cap remover 860 and cap 740, cap 740 is removed from fill tube 714 and retained on cap remover 860. In this position, second end 722 of fill tube 714 is openly exposed within cavity 808 of housing 790. Due to the electron field maintained within cavity 808, however, second end 722 of fill tube 714 remains sterilized.

Figure 49:
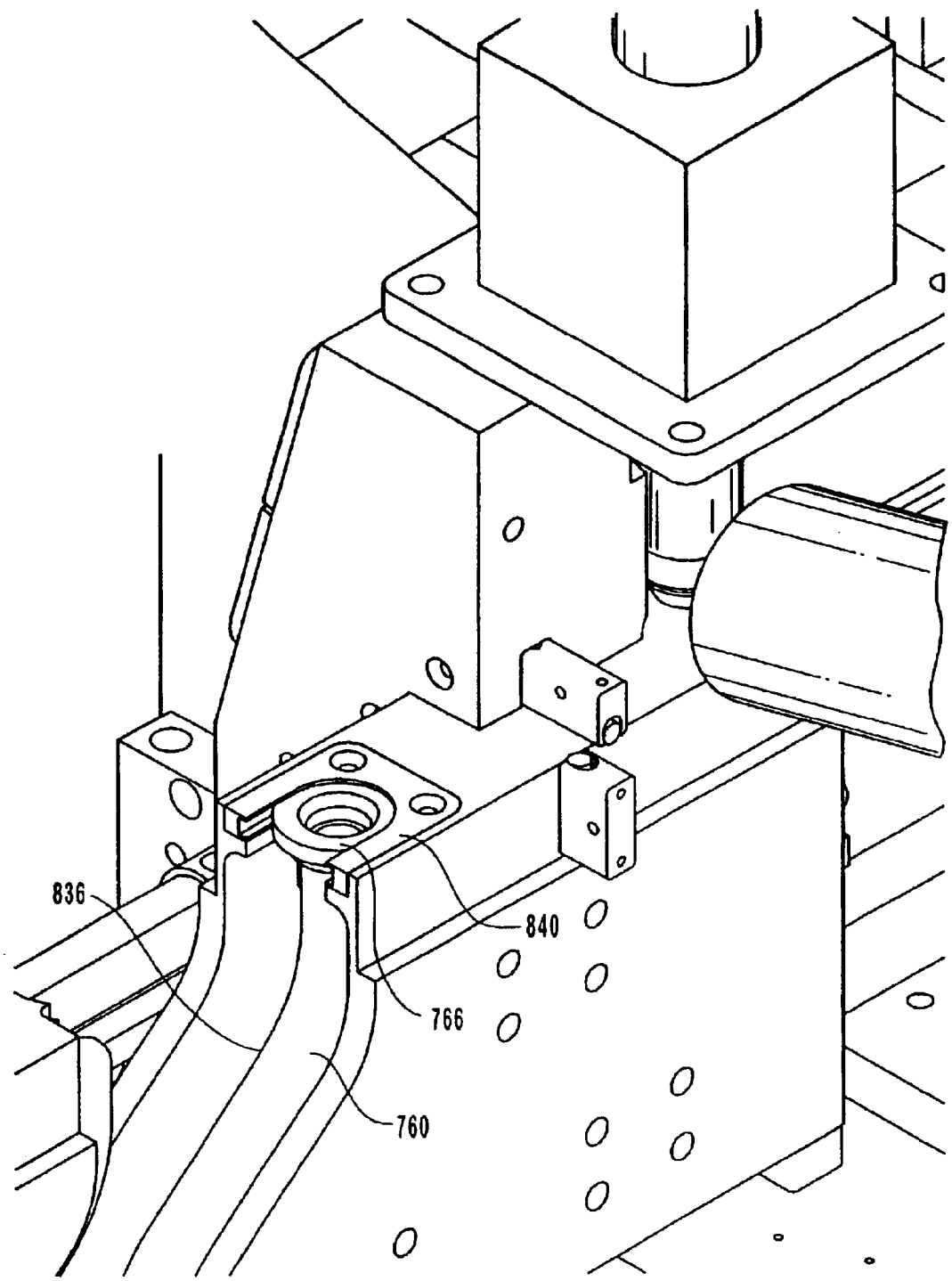
FIG. 49 is a perspective view of the sterilizer shown in FIG. 42 with the fill port being coupled therewith.
Figures 50, 51:
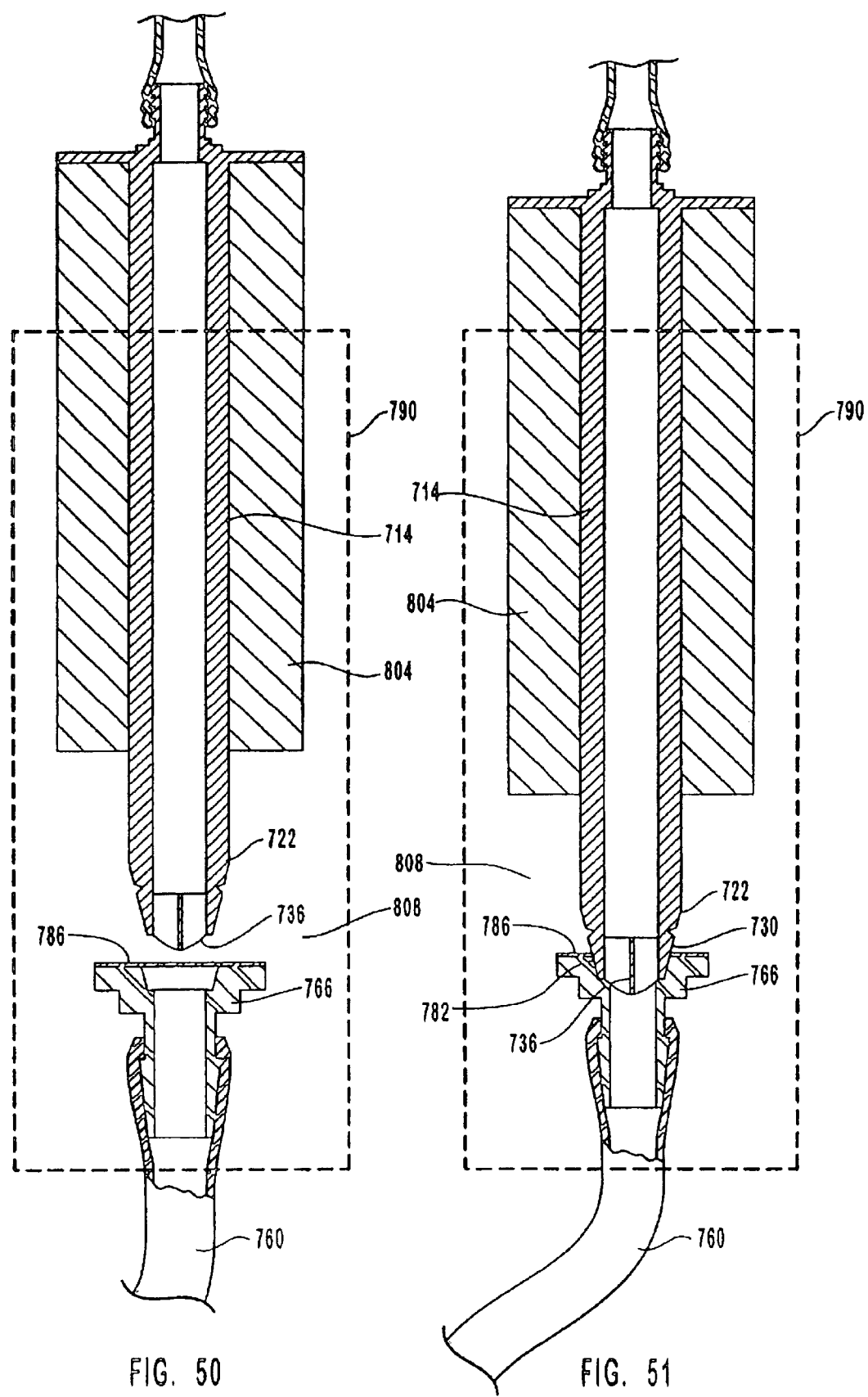
FIG. 50 is a cross sectional side view of the fill tube shown in FIG. 48 being aligned with the fill port.
FIG. 51 is a cross sectional side view of the fill tube shown in FIG. 48 coupled with the fill port.

Once cap 740 is removed, shuttles 818 and 820 slide out of housing 790 and separate. Next, as depicted in FIG. 49, cap remover 860 is replaced in retaining collar 840 with fill port 766 of collector assembly 704 (FIG. 36). Extension tube 760 is positioned within channel 836. Again, shuttles 818 and 820 are closed locking fill port 766 and extension tube 760 therebetween. As depicted in FIG. 50, the mated shuttles are then slid within housing 790 so that fill port 766 is vertically disposed below and in communication with cavity 808. The exterior of fill port 766 is thus sterilized through exposed to the electron field.

Once fill port 766 is positioned, fill tube 714 is again lowered. In so doing, as shown in FIG. 51, blades 736 of fill tube 714 puncture membrane 786. Once membrane 786 is punctured, nose 730 of fill tube 714 engages against seat 782, thereby forming a fluid coupling between fill tube 714 and fill port 766. Again, it is appreciated that throughout the process the electron field is maintained within cavity 808 so that all parts therein are sterilized.

Once fill tube 714 is coupled with fill port 766, clamp 757 (FIG. 41) is opened allowing the flow of solution through delivery assembly 702 and into collecting assembly 704, thereby filling container 765. As depicted in FIG. 1, in one embodiment a scale 882 is disposed below container 765. Once container 765 has been filled to a desired weight or to other form of fill mark, clamp 757 is again closed, thereby closing off the flow of solution. A tube heat sealer 880, which comprises two opposing heated elements as shown in FIG. 43, is then closed on opposing sides of extension tube 760, thereby pinching and heat sealing extension tube 760 closed. Extension tube 760 is then either removed from the shuttles or cut above the seal so as to allow removal of container 765 containing the sterile solution.

Once a first container 765 is filled, the process can be repeated for a new collector assembly 704. That is, fill tube 714 is raised within cavity 808 and shuttles 818 and 820 retracted. A new fill port 766 coupled with a new container 765 is then mounted with shuttles and shifted back into cavity 808 for filling by fill tube 714.

Housing 790 and shuttles 818 and 820 are configured to shield the emission of the electron field outside of cavity 808. However, channel 836 cannot be shielded closed in that extension tube 760 is disposed therein. The electrons entering cavity 808 travel in straight paths and dissipate once they encounter the shielding. Accordingly, to prevent the emission of electrons though channel 836, channel 836 is curved in a step-like fashion as previously discussed. This curvature of channel 836 ensures that the electrons entering channel 836 contact the wall bounding channel 836 prior to exiting therethrough. In alternative embodiments, channel 836 can be curved, bent, or otherwise shielded or blocked in a variety of different configurations so as to prevent a straight path from cavity 808 to the exterior.

In the above described embodiment of sterilizer 706, electron beam generators are used for sterilizing parts within or communicating with cavity 808. In alternative embodiments, it is appreciated that other forms of radiation, such as ultra violet light, can also be used for sterilization. In yet other embodiments, thermal sterilization can be used such as by the use of steam. Finally, vapor phase sterilization can be used such as through the use of hydrogen peroxide or chlorine dioxide. Each of the above described options are examples of means for generating a sterilizing field with cavity 808.

In one embodiment, once the solution is emptied from mixing bag 202, all of the components that were in direct contact with the solution are simply removed and disposed of or recycled. For example, each of the structural components such as the mixing bag, feed bag, mixer, tubes, pressure sensor diaphragm, connectors, ports, filters, and delivery assembly are designed and manufactured so as to be considered disposable components. Once the old components are removed, they are replaced with clean components. The fluid preparation process can then be repeated for a new solution without the need for cleaning, sterilization, or the risk of cross contamination. Of course in alternative embodiments where the solution need not be sterile or pure, some or all of the components can be repeatedly used and then discarded when worn or when an incompatible solution is to be prepared.

In one embodiment it is desirable that each of the structural components that the solution contacts be made from the same resin family. For example, each of the above identified structural components and any others that directly contact the solution or feed component can be made of polyethylene.

By having all of the structural components made from the same resin family, it is easier to control and monitor any effects resulting from leaching, adsorption, and absorption between the solution and the structural components. Depending on the solution being made, it can also be desirable that the structural components that contact the solution satisfy USP Class 6 testing for biological products and/or that they have no cytotoxic effects. In other embodiments, the different components can be made of different materials and need not satisfy the above testing.

XI. Conclusion.

It is appreciated from the forgoing that the inventive fluid preparation system 10 can, in various embodiments, include manually actuated components, electrically actuated components, and combinations thereof. In embodiments, where electrically actuated components are used, a central processing unit 890, as shown in FIG. 1, is provided for controlling the components. Furthermore, central processing unit 890 can be loaded with select programs for automating select operations of the fluid preparation system 10.

Fluid preparation system 10 and the structural components thereof provide a number of unique advantages over conventional fluid preparation systems. By way of example and not by limitation, the system enables a manufacturer or an end user to efficiently manufacture predefined amounts of a solution to meet a desired need, thereby avoiding short supply or the necessary storage of over supply. By using disposable components, the system can be used to rapidly make different batches or types of solutions without the costly delay or expense of having to clean or sterilize structural parts. The mixers enable efficient mixing of the solution while minimizing high shearing, foaming or splashing that could be potentially detrimental to some solutions. The feed bag enables efficient storage and dispensing of powder components while minimizing the possibility of potentially harmful components being emitted into the surrounding environment. Similarly, the final dispensing system provides an efficient way for quickly filling a number of different containers and switching between different solution batches while ensuring that the solution is sterile and sealed in a closed container.

Fluid preparation system 10 includes many discrete components, some of which are identified by section headings. It is appreciated that each of the disclosed components and alternatives thereof contain novel features and that each component can be used independently, in different assemblies of fluid preparation system 10, or in systems other than fluid preparation systems. For example, it is appreciated that each of the various components can be mixed and matched depending on the type of solution to be made and whether or not the solution needs to be sterile. As such, different systems may have different benefits and be used in different ways.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for mixing a solution, the method comprising:
   positioning a collapsible container within a chamber of a substantially rigid tank, the collapsible container bounding a compartment, a mixer being disposed within the compartment of the container;
   feeding two or more components into the compartment of the container, at least one of the components being a liquid; and
   raising and lowering the mixer within the compartment of the container so as to mix the components.

2. A method as recited in claim 1, further comprising raising or lowering a floor of the tank before or after inserting the collapsible container within the chamber of the tank so as to adjust the size of the chamber of the tank.

3. A method as recited in claim 1, further comprising heating or cooling at least a portion of the tank so as to correspondingly heat or cool the components within the compartment of the container.

4. A method as recited in claim 1, further comprising inflating the collapsible container with a gas within the chamber of the tank.

5. A method as recited in claim 1, wherein the collapsible container has a volume of at least 20 liters.

6. A method as recited in claim 1, wherein the collapsible container has a volume of at least 500 liters.

7. A method as recited in claim 1, wherein the act of feeding the at least two or more components comprises at least one of the components being a substantially dry material.

8. A method as recited in claim 7, wherein the dry material comprises culture media, buffers, or reagents.

9. A method as recited in claim 7, further comprising maintaining a positive gas pressure within the compartment of the collapsible container while at least a portion of the substantially dry material is fed into the compartment.

10. A method as recited in claim 1, wherein a shaft has a first end coupled with the mixer disposed within the compartment of the collapsible container and an opposing second end disposed outside of the collapsible container, the method further comprising connecting the second end of the shaft to a driver for selectively raising and lower the shaft.

11. A method as recited in claim 1, further comprising spraying a liquid into the compartment of the collapsible container so as to capture any component suspended in air within the compartment or resting on the collapsible container.

12. A method as recited in claim 1, further comprising:
   removing the mixed components from the compartment of the collapsible container; and
   injecting gas into the compartment of the collapsible container as the mixed components are removed therefrom.

13. A method as recited in claim 1, further comprising:
   removing the mixed components from the compartment of the collapsible container;
   withdrawing the collapsible container with the mixer therein from the chamber of the tank; and
   inserting a new collapsible container with a new mixer therein into the chamber of the tank.

14. A method as recited in claim 1, further comprising:
   draining the mixed components from the collapsible container through an exit tube;
   passing the mixed components through a sterilizing filter; and
   dispensing the sterile mixed components into a sterile container.

15. A method for mixing a solution, the method comprising:
   positioning a flexible mixing bag within a chamber of a substantially rigid tank, the flexible mixing bag bounding a compartment, a mixer being disposed within the compartment of the mixing bag;
   inflating the mixing bag with a gas;
   feeding two or more components into the compartment of the mixing bag, at least one of the components being a liquid; and mixing the components within the compartment of the mixing bag using the mixer.

16. A method as recited in claim 15, wherein the act of mixing the components comprises raising and lowering the mixer within the compartment.

17. A method as recited in claim 16, wherein a shaft has a first end coupled with the mixer disposed within the compartment of the mixing bag and an opposing second end disposed outside of the mixing bag, the method further comprising connecting the second end of the shaft to a driver for selectively raising and lower the shaft.

18. A method as recited in claim 15, further comprising raising or lowering a floor of the tank before or after inserting the mixing bag within the chamber of the tank so as to adjust the size of the chamber of the tank.

19. A method as recited in claim 18, further comprising maintaining a positive gas pressure within the compartment of the mixing bag while at least a portion of the substantially dry material is fed into the compartment.

20. A method as recited in claim 15, further comprising heating or cooling at least a portion of the tank so as to correspondingly heat or cool the components within the compartment of the mixing bag.

21. A method as recited in claim 15, wherein the mixing bag has a volume of at least 1,000 liters.

22. A method as recited in claim 15, wherein the act of feeding the at least two or more components comprises at least one of the components being a substantially dry material.

23. A method for mixing a solution, the method comprising:

positioning a first disposable mixing bag within a chamber of a substantially rigid reusable tank, the first disposable mixing bag bounding a compartment, a first disposable mixer being disposed within the compartment of the first disposable mixing bag, a disposable shaft having a first end coupled with the first disposable mixer disposed within the compartment of the first disposable mixing bag and having an opposing second end disposed outside of the first disposable mixing bag;

feeding two or more components into the compartment of the first disposable mixing bag, at least one of the components being a liquid;

mixing the components within the compartment of the first disposable mixing bag using the first disposable mixer, the act of mixing further comprising connecting the second end of the disposable shaft to a driver that selectively raises and lowers the disposable shaft;

removing the mixed components from the compartment of the first disposable mixing bag;

disposing of the first disposable mixing bag and the first disposable mixer; and inserting a second disposable mixing bag within the chamber of the reusable tank, the second disposable mixing bag bounding a compartment, a second disposable mixer being disposed within the compartment of the second disposable mixing bag.

24. A method as recited in claim 23, further comprising removably connecting a first end of a reusable shaft to the first disposable mixer disposed within the compartment of the first disposable mixing bag such that a second end of the shaft is disposed exterior of the first disposable mixing bag.

25. A method as recited in claim 24, further comprising attaching the second end of the reusable shaft to a driver that selectively raises and lowers the reusable shaft so as to raise and lower the first disposable mixer, thereby mixing the components.

26. A method as recited in claim 23, wherein the act of feeding the at least two or more components comprises at least one of the components being a substantially dry material.

27. A method as recited in claim 23, wherein the act of feeding the at least two or more components comprises at least one of the components being a culture media, buffer, or reagent.

28. A method for mixing a solution, the method comprising:

positioning a first disposable mixing bag within a chamber of a substantially rigid reusable tank, the first disposable mixing bag bounding a compartment, a first disposable mixer being disposed within the compartment of the first disposable mixing bag;

removably connecting a first end of a reusable shaft to the first disposable mixer disposed within the compartment of the first disposable mixing bag such that a second end of the shaft is disposed exterior of the first disposable mixing bag;

attaching the second end of the reusable shaft to a driver feeding two or more components into the compartment of the first disposable mixing bag, at least one of the components being a liquid;

activating the driver so that the driver selectively raises and lowers the reusable shaft so as to raise and lower the first disposable mixer, thereby mixing the components within the compartment of the first disposable mixing bag using the first disposable mixer;

removing the mixed components from the compartment of the first disposable mixing bag;

disposing of the first disposable mixing bag and the first disposable mixer; and inserting a second disposable mixing bag within the chamber of the reusable tank, the second disposable mixing bag bounding a compartment, a second disposable mixer being disposed within the compartment of the second disposable mixing bag.

* * * * *